United States Patent
Ouzunova et al.

(10) Patent No.: US 10,897,862 B2
(45) Date of Patent: Jan. 26, 2021

(54) **PLANT RESISTANT TO *HELMINTHOSPORIUM TURCICUM***

(71) Applicants: KWS SAAT SE & CO. KGAA, Einbeck (DE); UNIVERSITÄT ZÜRICH, Zürich (CH)

(72) Inventors: Milena Ouzunova, Göttingen (DE); Daniela Scheuermann, Einbeck (DE); Beat Keller, Zürich (CH); Simon Krattinger, Bonstetten (CH); Thomas Wicker, Hüttwilen (CH); Gerhard Herren, Gossau (CH); Severine Hurni, Lucerne (CH); Bettina Kessel, Einbeck (DE); Thomas Presterl, Einbeck (DE); Carsten Knaak, Göttingen (DE)

(73) Assignees: KWS SAAT SE & CO. KGAA, Einbeck (DE); UNIVERSITÄT ZÜRICH, Zürich (CH)

( * ) Notice: Subject to any disclaimer, the term of this patent is extended or adjusted under 35 U.S.C. 154(b) by 77 days.

(21) Appl. No.: 14/916,671

(22) PCT Filed: Sep. 3, 2014

(86) PCT No.: PCT/EP2014/002386
§ 371 (c)(1),
(2) Date: Mar. 4, 2016

(87) PCT Pub. No.: WO2015/032494
PCT Pub. Date: Mar. 12, 2015

(65) Prior Publication Data
US 2016/0201080 A1  Jul. 14, 2016

(30) Foreign Application Priority Data

Sep. 4, 2013  (DE) .................. 10 2013 014 637
Apr. 24, 2014  (DE) .................. 10 2014 005 823

(51) Int. Cl.
| | |
|---|---|
| *A01H 1/04* | (2006.01) |
| *C12Q 1/68* | (2018.01) |
| *C12Q 1/6895* | (2018.01) |
| *C07K 14/415* | (2006.01) |
| *A01H 5/00* | (2018.01) |
| *C12N 15/82* | (2006.01) |

(52) U.S. Cl.
CPC .............. *A01H 1/04* (2013.01); *A01H 5/00* (2013.01); *C07K 14/415* (2013.01); *C12N 15/8282* (2013.01); *C12Q 1/6895* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS 9,040,772 B2 * 5/2015 Li .................. A01H 1/04
800/267

FOREIGN PATENT DOCUMENTS

| WO | 00/29592 A2 | 5/2000 |
| WO | 2007/147395 A2 | 12/2007 |
| WO | 2008/034648 A1 | 3/2008 |
| WO | 2010/079430 A1 | 7/2010 |
| WO | 2011/072246 A2 | 6/2011 |
| WO | 2011/163590 A1 | 12/2011 |

OTHER PUBLICATIONS

Fourgoux-Nicol et al (1999, Plant Molecular Biology 40: 857-872).*
Gevers, H O, "A New Major Gene for Resistance to Helminthosporium-turcicum Leaf Blight of Maize", Plant Disease Reporter, Washington, DC, US, 1975, vol. 59, No. 4, pp. 296-299.
Chia-Lin Chung, et al., "Analysis of qEt8.06. A Major QTL for Resistance to Northern Leaf Blight in Maize", Annual Research Meeting of Generation Challenge Program, Jan. 1, 2008 (Jan. 1, 2008), Bangkok, Thailand, Retrieved from the Internet: URL:http://www.plantpath.cornell.edu/labs/nelson r/Docs/OI CLC 08GCP 12Sep08 2.pdf [retrieved on Nov. 21, 2014].
Chia-Lin Chung, et al., "Characterization and fine-mapping of a resistance locus for northern leaf blight in maize bin 8.06", Theoretical and Applied Genetics, International Journal of Plant Breeding Research, Springer, Berlin, DE, 2010, vol. 121, No. 2, pp. 205-227.
PCT International Search Report and Written Opinion issued in corresponding PCT Application No. PCT/EP2014/002386.

(Continued)

*Primary Examiner* — Medina A Ibrahim
(74) *Attorney, Agent, or Firm* — Troutman Pepper Hamilton Sanders LLP

(57) ABSTRACT

The present invention provides an improved *Helminthosporium turcicum*-resistant plant, in particular a maize plant which comprises a polynucleotide with one or more resistance-conferring genes, for example on a truncated chromosome fragment from the accession Pepitilla, as well as a cell, a tissue, a part, grain and seeds thereof, an isolated polynucleotide which comprises one or more resistance-conferring genes against *Helminthosporium turcicum*, a vector, a transgenic plant cell and a transgenic plant containing this polynucleotide. Furthermore, the invention encompasses suitable markers and their use in introducing resistance or the transgene into a plant, as well as the identification of improved maize plants which comprise a truncated chromosome fragment.

7 Claims, 4 Drawing Sheets

Figure 1:
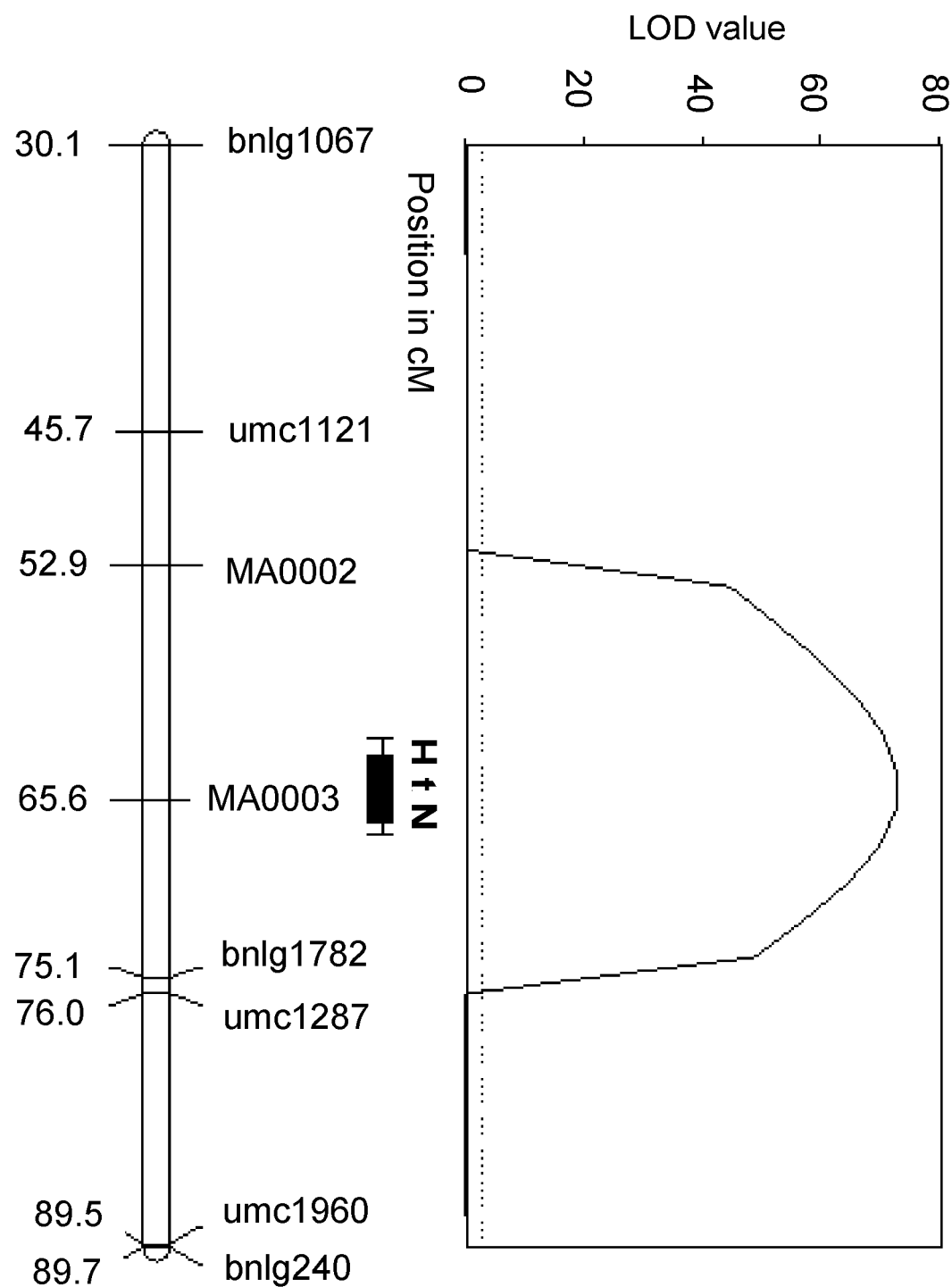

Specification includes a Sequence Listing.

(56) References Cited

OTHER PUBLICATIONS

Bar-Zur, et al., "Resistance to northern leaf blight in maize (Zea mays) conditioned by the HtN gene and the association with isoperoxidases", Canadian Journal of Plant Pathology 20(1): 28-34, 1998.
Brunner, et al., "Transgenic Pm3b wheat lines show resistance to powdery mildew in the field", Plant Biotechnology Journal 9: 897-910, 2011.
Carson, et al., "A New Gene in Maize Conferring the "Chlorotic Halo" Reaction to Infection by Exserohilum turcicum", Plant Disease 79: 717-720, 1995.
Chevalier, et al., "Design, Activity, and Structure of a Highly Specific Artificial Endonuclease", Molecular Cell. 10: 895-905, 2002.
Chung, et al., BMC Plant Biology 10: 103, 2010.
Chung, et al., "Characterization and fine-mapping of a resistance locus for northern leaf blight in maize bin 8.06", Theoretical and Applied Genetics 121(2): 205-227, 2010.
Coates, et al., "Inheritance of resistance to gray leaf spot in crosses involving selected resistant inbred lines of corn", Phytopathology 88(9): 972-982, 1998.
Depicker, et al., "Nopaline synthase: transcript mapping and DNA sequence", J. Mol. Appl. Genet. 1(6): 561-573, 1982.
Ferguson, et al., "Temporal Variation in Setosphaeria turcica Between 1974 and 1994 and Origin of Races, 1, 23, and 23N in the United States", Genetics and Resistance 97(11): 1501-1511, 2007.
Gaj, et al., "ZFN, TALEN, and CRISPR/Cas-based methods for genome engineering", Trends in Biotechnology, pp. 1-9, 2013.
Ganal, et al., "A large maize (Zea mays L.) SNP genotyping array: Development and germplasm genotyping, and genetic mapping to compare with the B73 reference genome" , PLoS ONE6 e28334, 2011.
Gianasi, et al., "Raçes fisiológocas de Exserohilum turcicum identificadas em regiões produtoras de milho no Brasil, Safra 93/94", [Physiological races of Exserohilum turcicum identified in maize-producing regions of Brazil, Safra 93/94] Summa Phytopathyol. 22: 214-217, 1996.
Griffiths, et al, "Mapping with Molecular Markers", Mapping Eukaryote Chromosomes by Recombination (Ch. 4), An Introduction to Genetic Analysis, 7th Ed., pp. 131-135, 2000.
Gupta, et al., Cereal Genomics II. Springer Science+Business Media Dordrecht, Netherlands; DOI: 10.1007/978-94-007-6401-9_1, 2013.
Hanekamp, et al., "Turcicum Blattdürre an Mais: Rassenbestimmung und regionales Auftreten von Exserohilum turcicum in Europa", [Turcicum leaf blight in maize: race determination and regional occurrence of Exserohilum turcicum in Europe], PG Krankheiten an Getreide, Vortrag: Blattdürre, 2013.
Jordan, et al., "Occurrence of Race 2 of Exserohilum turcicum on Corn in the Central and Eastern United States", Plant Disease 67(10): 1163-1165, 1983.
Li, et al., "TAL nucleases (TALNs): hybrid proteins composed of TAL effectors and FokI DNA-cleavage domain", Nucleic Acids Research 39(1): 359-372, 2011.
Lipps, et al., "Exserohilum turcicum Virulent on Corn with the Ht Resistance Gene in Ohio", Plant Disease 66(5): 397-398, 1982.
Lipps, et al., "Interaction of Ht and Partial Resistance to Exoserohilum turcicum in Maize", Plant Disease 81(3): 277-282, 1997.
Manoli, et al., "Evaluation of candidate reference genes for qPCR in maize", Journal of Plant Physiology 169(8): 807-815, 2012.
Margulies, et al., "Genome sequencing in microfabricated high-density picolitre reactors", Nature 437: 376-380, 2005.
Min, et al., "Pyramiding Resistance Genes to Northern Leaf Blight and Head Smut in Maize", Int. J. Agric. Biol. 14(3): 430-434, 2012.
Moghaddam, et al., "Reactions of Isolates from Matings of Races 1 and 23N of Exserohilum turcicum", Plant Disease 78(8): 767-771, 1994.
Odell, et al., "Identification of DNA sequences required for activity of the cauliflower mosaic virus 35S promotor", Nature 313: 810-812, 1985.
Pataky, et al., "Disease Severity and Yield of Sweet Corn Hybrids with Resistance to Northern Leaf Blight", Plant Disease 82(1): 57-63, 1998.
Perkins, et al., "Disease Development and Yield Losses Associated with Northern Leaf Blight on Corn", Plant Disease 71(10): 940-943, 1987.
Pratt, et al., "Breeding for resistance to maize foliar pathogens", Plant Breed Rev. 27: 119-173, 2006.
Puchta, et al., "Breaking news: Plants mutate right on target", PNAS 107(26): 11657-11658, 2010.
Raymundo, et al., "Effect of Gene HtN on the Development of Northern Corn Leaf Blight Epidemics", Plant Disease 65(4): 327-330, 1981.
Raymundo, et al., "Measuring the Relationship Between Northern Corn Leaf Blight and Yield Losses", Plant Disease 65(4): 325-327, 1981.
Risk, et al., "Functional varability of the Lr34 durable resistance gene in transgenic wheat", Plant Biotech. Journal 10: 477-487, 2012.
Rozen, et al., "Primer3 on the WWW for General Users and for Biologist Programmers", Methods in Molecular Biology, vol. 132: Bioinformatics Methods and Protocols, pp. 365-386, 2000.
Rushton, et al., "Interaction of elicitor-induced DNA-binding proteins with elicitor response elements in the promoters of parsley PR1 genes", the EMBO Journal 15(20): 5690-5700, 1996.
Shimoni, et al., "The association of peroxidase activity and resistance of maize to Exserohilum turcicum", Journal of Phytopathology 131(4): 315-321, 1991.
Silva, et al., "Meganucleases and Other Tools for Targeted Genome Engineering: Perspectives and Challenges for Gene Therapy", Current Gene Therapy 11(1): 11-27, 2011.
Simcox, et al., "The Use of Molecular Markers to Study Setosphaeria turcica Resistance in Maize", Molecular Plant Pathology 83(12): 1326-1330, 1993.
Stankovic, et al., "Genetic Variability of Maize Pathogens in Serbia", Genetika 39(2): 227-240, 2007.
Thakur, et al., "Effects of Temperature and Light on Virulence of Exserohilum turcicum on Corn", Phytopathology 79: 331-635, 1989.
Tzfira, et al., "Genome modifications in plant cells by custom-made restriction enzymes", Plant Biotechnology Journal 10(4): 373-389, 2012.
Ullstrup, et al., "The effects of some leaf blights on corn grain yield", Phytopathology 47: 331-336, 1957.
Walsh, et al., Poster presentation P192, 50th Maize Genetics Conference in Washington, D.C. 2008.
Welz, "Genetics and epidemiology of the pathosystem Zea mays / Setosphaeria turcica" Habilitationsschrift Institut for Pflanzenzüchtung, Saatgufforschung and Populationsgenetik, Universität Hohenheim, 1998.
Welz, et al., "Genes for resistance to northern corn leaf blight in diverse maize populations", Plant Breeding 119: 1-14, 2000.
Feb. 16, 2012, "Zea mays NLB18 cDNA (PH99N haplotype) SEQ:94," retrieved from EBI accession No. GSN: AZR18838 Database accession No. AZR18838 sequence & DATABASE Geneseq.
Feb. 16, 2012, "Zea mays NLB18 cDNA (PH99N haplotype) encoding protein SEQ:95," XP002732782, retrieved from EBI accession No. GSP:AZR18839 Database accession No. AZR18839 sequence & DATABASE Geneseq.
Feb. 16, 2012, "NLB18_E candidate gene DNA specific PCR forward primer SEQ:77," retrieved from EBI accession No. GSN:AZR18821 Database accession No. AZR18821 sequence.
Oct. 29, 2009, "Nucleotide sequence SEQ ID 190015," retrieved from EBI accession No. GSN:AWL16812 Databse accession No. AWL16812 sequence.
Jiao, Y. et al., "Improved maize reference genome with single-molecule technologies", Nature, Jun. 22, 2017, 546:524-529.

\* cited by examiner

PLANT RESISTANT TO *HELMINTHOSPORIUM TURCICUM*

CROSS-REFERENCE TO RELATED APPLICATIONS

This application is a US National Stage of International Application No. PCT/EP2014/002386 filed 3 Sep. 2014, which claims the benefit of German Patent Application Nos. 102013014637.2 filed 4 Sep. 2013 and 102014005823.9 filed 24 Apr. 2014, the entire contents of each of which applications are hereby incorporated by reference.

FIELD OF THE INVENTION

The present invention relates to the field of the modification of plants using molecular biological methods and marker technology, along with genetic engineering. It concerns a novel *Helminthosporium turcicum*-resistant plant, in particular a maize plant which comprises a polynucleotide with one or more resistance-conferring genes on a modified chromosome fragment from the accession Pepitilla, as well as a cell, a tissue, a portion, grain and seed thereof, an isolated polynucleotide which comprises one or more resistance-conferring genes against *Helminthosporium turcicum*, a vector, a transgenic plant cell and a transgenic plant containing this polynucleotide. The invention also encompasses suitable molecular markers and their use in introducing the resistance locus or the transgene into a plant, as well as the identification of improved maize plants which comprise a modified chromosome fragment.

BACKGROUND OF THE INVENTION

In maize (*Zea mays* L.), there are a large number of fungal pathogens which cause leaf diseases. The fungus which can cause by far the most damage under tropical and also under temperate climatic conditions, such as those in large parts of Europe and North America as well as in Africa and India, is known as *Helminthosporium turcicum* or synonymously as *Exserohilum turcicum* (Pass.) Leonard and Suggs (teleomorph: *Setosphaeria turcica* (Luttrell) Leonard & Suggs). *H. turcicum* is the cause of the leaf spot disease known as "Northern Corn Leaf Blight" (NCLB), which can occur in epidemic proportions during wet years, attacking vulnerable maize varieties and causing a great deal of damage and considerable losses of yield of 30% and more over wide areas (Perkins & Pedersen, 1987; Raymundo & Hooker, 1981a; Ullstrup & Miles, 1957). Since the 1970s, then, natural resistance in genetic material has been sought. Currently, quantitative and qualitative resistances are known. While the oligo- or polygenically inherited quantitative resistance appears incomplete and non-specific as regards race in the phenotype and is influenced by additional and partially dominant genes, qualitative resistance is typically race-specific and can be inherited through individual, mostly dominant genes such as Ht1, Ht2, Ht3, Htm1 or Htn1 (Lipps et al., 1997; Welz & Geiger, 2000). Backcrosses in many frequently used inbred maize lines such as W22, A619, B37 or B73 have successfully brought about introgression of the HT genes, where they exhibit a partial dominance and expression as a function of the respective genetic background (Welz, 1998).

Despite this complex genetic architecture of NCLB resistance in maize, until now principally the use of the Ht1 gene in maize together with a partial quantitative resistance has been sufficient to control helminthrosporiosis (Welz, 1998). The basis for this is that globally, race 0 of *H. turcicum* dominates as regards use (approximately 55%) (Lipps et al., 1997; Ferguson & Carson, 2007), while other races such as 2N and 23N are only rarely used and even then in a geographically restricted area (Moghaddam & Pataky, 1994; Jordan et al., 1983; Lipps & Hite, 1982; Thakur et al., 1989; Welz, 1998). This race 0 is avirulent having regard to a maize plant with Ht1, so that when provided with a suitable quantitative resistance, it exhibits a sufficient general resistance to NCLB. However, many studies have reported an increasing dissemination of the less common races (Jordan et al., 1983; Welz, 1998; Pratt & Gordon, 2006). The reasons for this are linked to the population dynamic of a pathogen which allows changes in pathogen virulence by new mutations on avirulence genes and new combinations of available virulence genes. Finally, this can lead to the occurrence of new, suitable, sometimes more aggressive pathogenic races. In Brazil, for example, the *H. turcicum* population already appears to be substantially more diverse having regard to the race composition than, for example, in North America. Gianasi et al. (1996) reported *H. turcicum* races which have already broken through the resistance conferred by the Ht1 gene. In addition, there is the instability of the resistance genes to certain environmental factors such as temperature and light intensity in some climate zones (Thakur et al., 1989). This development has the consequence that globally, the use of novel HT resistance genes or such to which, until now, little attention has been paid for the production of commercial maize plants is growing in importance in order to target a broader and more long-lasting resistance to *H. turcicum* in maize. Initial approaches in this regard were attempted as early as 1998 by Pataky et al. The NCLB resistance in sh2 elite maize was improved by using a combination of Ht1 and Htn1.

A source of monogenic Htn1 resistance is the Mexican landrace "Pepitilla" (Gevers, 1975). Htn1 introgression lines exhibit a gene mapping on the long arm of chromosome 8 approximately 10 cM distal from Ht2 and 0.8 cM distal from the RFLP marker umc117 (bin 8.06) (Simcox & Bennetzen, 1993). In contrast to the usual HT resistance genes, Htn1 confers resistance by delaying the onset of sporulation, and thus combats the development of lesions. As a result, fewer, smaller lesions as well as reduced sporulation zones are formed (Raymundo et al., 1981b, Simcox & Bennetzen, 1993). Chlorotic-necrotic lesions such as those which occur with Ht1, Ht2 or Ht3-conferred resistance, are not formed (Gevers, 1975). However, the resistance reaction in the heterozygous state of the Htn1 gene is significantly less effective than in the homozygous state (Raymundo et al., 1981b).

The development of additional specific markers which could further simplify genotype determination would improve the breeding manageability of the Htn1 gene. Marker assisted selection (MAS) technology thus makes efficient stacking or pyramiding of several resistance genes possible (Min et al., 2012). The introgression lines B37Htn1 or W22Htn1 were employed in many studies on mapping the resistance locus and identifying the resistance source (Raymundo et al., 1981a, b; Simcox & Bennetzen, 1993, Bar-Zur et al., 1998; Coates & White, 1998). Available information regarding markers which could be used for selection of the resistance locus for Htn1 from the accession Pepitilla, however, is still only limited (Simsox & Bennetzen, 1993). The known markers for Htn1 which are functional for and flank the resistance locus from the accession Pepitilla are still mapped at close to 22.2 cM apart, which in the best case scenario allows selection of a large chromosome fragment.

However, there is a frequent risk that within this fragment between the markers, a double genetic recombination occurs which could result in a false positive selection for the Htn1 resistance locus. In addition, in some cases the probability of unwanted genetic regions being taken into the introgression line rises with the size of the introgressed chromosome fragment and be transmitted over generations of elite lines. Such genetic regions, in particular when they are closely coupled with the Htn1 locus and lead to unequivocally negative effects on one or more agronomic features, are known as linkage drag. From known studies which investigated and used introgression lines with Htn1 from Pepitilla, however, such negative effects are unknown. Even the very comprehensive research work by Welz (1998) which, inter alia, was also carried out on B37Htn1, postulated that in view of, for example, yield and ripening, introgression of the Htn1 locus brought about no significant disadvantages. Thus, no serious efforts have been made in the prior art to deliberately shorten the large chromosome fragment.

In contrast, WO 2011/163590 discloses the genotype PH99N as an alternative source for NCLB resistance on chromosome 8 bin 5 which, however, does not correspond to the accession Pepitilla. Essentially, only resistance as regards *H. turcicum* races 0 and 1 have been identified in backcross populations from PH99N. Even the resistance phenotype was not clearly determined. Nevertheless, the authors concluded that the resistance was due to the Htn1 gene. But the resistance locus in PH99N was restricted to only a ~224 kb long chromosome fragment; a resistant maize plant with the 224 kb fragment and thus the assumed Htn1 was not disclosed, however. In addition, the genotype PH99N was not made available to the public by deposition.

An alternative approach to making the Htn1 gene useful is the identification and cloning of the resistance gene and using it in a transgenic strategy.

With the intention of identifying the resistance gene for NCLB, in 2010, Chung et al. 2010 published a study for fine mapping the bin 8.06 resistance locus. The chromosome fragment under investigation, however, was not derived from Pepitilla but from the maize hybrid DK888 which exhibits multiple disease resistance. Investigations on *Helminthosporium* race specificity initially made it clear that the resistance locus on DK888, designated qNLB8.06$_{DK888}$, was closely linked or functionally linked with the Ht2 and Htn1 genes, since *Helminthosporium* strains 23 and 23N were virulent (Chung et al., 2008). Positive detection of the presence of Htn1 was not accomplished, however, in the absence of a pure N isolate from *H. turcicum*. In addition, the resistance phenotype with qNLB8.06$_{DK888}$ also did not correspond to the expected phenotype having regard to the appearance of chlorotic lesions and the delay in lesion formation. Further detailed complementation studies in Chung et al. (2010) finally provided indications that qNLB8.06$_{DK888}$ was either identical to, allelic, closely linked or functionally linked with Ht2, but not with Htn1. The resistance locus qNLB8.06$_{DK888}$ could be assigned to a chromosome fragment of 0.46 Mb. Genome annotations of this chromosome fragment hinted at 12 putative open reading frames, of which three could respectively be a tandem protein kinase-like gene (GRMZM2G135202; GRMZM2G164612) or a protein phosphatase-like gene (GRMZM2G119720) and each equally constituted promising candidate genes for the resistance gene Ht2 (Chung et al., 2010). A functional verification was not described.

Furthermore, WO 2011/163590 A1 also annotated the presumed Htn1 gene in the resistance source PH99N as a tandem protein kinase-like gene (GRMZM2G451147) and disclosed its genetic sequence, but also did not determine its functionality, for example in a transgenic maize plant.

SUMMARY OF THE INVENTION

The present invention stems from the prior art described above; the object of the present invention is to provide a maize plant which exhibits resistance to the pathogen *Helminthosporium turcicum* from the donor Pepitilla and wherein the agronomic features of known maize plants can be overlaid with resistance from the donor Pepitilla.

The object is accomplished on the one hand by the provision of a maize plant into the genome of which a chromosome fragment from the donor Pepitilla has been integrated, wherein the chromosome fragment comprises an interval of the donor (hereinafter termed the first interval or interval 1) which exhibits donor alleles in accordance with the haplotype shown in Table 2 and a polynucleotide which confers resistance to *Helminthosporium turcicum* in the maize plant, and wherein the chromosome fragment does not contain a further interval of the donor (hereinafter termed the second interval or interval 2) between a marker in a first marker region (M1) which is flanked by the markers SYN14136 and PZE-108076510 and a marker in a second marker region (M2) which is flanked by the markers SYN24931 and PZE-108077560. These and alternative solutions to the problem, described below, may be based on a breeding programme for integration of the Htn1 locus from Pepitilla into maize lines. However, genetic engineering approaches may also be selected, by means of which plants in accordance with the present invention may be produced. Examples of genetic engineering strategies are described in more detail below. In order to produce the plants of the present invention, various genotypes from the prior art may be used. In particular, B37HTN1, which comprises the resistance locus for the landrace “Pepitilla”, was used as the original line. In addition to Pepitilla itself and B37HTN1 (also known in the prior art as B37HtN), almost any maize genotype may be called upon for integration of the Htn1 locus in order to produce a maize plant in accordance with the invention into the genome of which, in particular on chromosome 8 bin 5 or 6, an introgression of the Htn1 resistance locus from Pepitilla has been inserted. In this respect, many examples of genotypes are known in the prior art, for example: W22Htn (e.g. Bar-Zur et al., 1998); H6314Htn (e.g. Bar-Zur et al., 1998), B73HtN (e.g. Shimoni et al., Journal of Phytopathology 131:4 (1991), 315-321), B68HtN and A632HtN (e.g. Carson, Plant Disease 79 (1995), 717-720) and A619HtN (e.g. Stanković et al, Genetika 39:2 (2007), 227-240). In a maize plant in accordance with the invention, the chromosome fragment derives from the donor Pepitilla; in a preferred embodiment of the maize plant in accordance with the invention, the chromosome fragment derives from the donor B37HTN1 or from another maize genotype as cited above. As an example, B37HTN1 may be ordered from the Maize Genetics COOP Stock Center using the stock ID 65749.

The chromosome fragment integrated into the genome of the maize plant of the invention derives from the donor Pepitilla which, as is known, comprises the resistance locus HTN1. The introgression of this resistance locus is localized on the long arm of chromosome 8, bin 8.05-8.06. The integrated chromosome fragment comprises the first interval of the donor, which comprises a polynucleotide which confers resistance against *Helminthosporium turcicum* in the maize plant of the invention. In this regard, the polynucleotide comprises one or more resistance-conferring genes of the HTN1 locus from Pepitilla (Table 1) or gene alleles thereof. Under *H. turcicum* infestation conditions, the gene or gene allele may produce a resistance phenotype with features typical of HTN1. Preferably, the polynucleotide comprises one or more resistance-conferring genes of the HTN1 locus, preferably from Pepitilla, selected from RLK1 and EXT1 (see Table 1) or gene alleles thereof which produce a resistance phenotype with the typical features of HTN1 under *H. turcicum* infestation conditions. Particularly preferably, the polynucleotide comprises a nucleotide sequence which codes for a polypeptide in accordance with SEQ ID NO: 2 or SEQ ID NO: 6 or a homologue of a polypeptide in accordance with SEQ ID NO: 2 or SEQ ID NO: 6, which produce a resistance phenotype with the typical features of HTN1 under *H. turcicum* infestation conditions. Examples of these features typical of HTN1 are delayed onset of sporulation, reduced development of lesions, development of smaller lesions, reduced sporulation zones and/or no or only isolated chlorotic-necrotic lesions. Structurally, the polynucleotide is characterized in that it comprises a nucleic acid molecule which (a) comprises a nucleotide sequence in accordance with SEQ ID NO: 1, 3, 5, 7, 9, 11, 13 or 15, (b) comprises a nucleotide sequence with an identity of at least 80%, 85%, 90%, 91%, 92%, 93%, 94%, 95%, 96%, 97%, 98% or 99% with one of the nucleotide sequences in accordance with SEQ ID NO: 1, 3, 5, 7, 9, 11, 13 or 15, preferably over the entire length of the sequence, (c) which hybridizes with the complementary strand of a nucleic acid molecule in accordance with (a) or (b) under stringent conditions, (d) which codes for a polypeptide with an amino acid sequence in accordance with SEQ ID NO: 2, 4, 6, 8, 10, 12, 14 or 16, (e) which codes for a polypeptide with an amino acid sequence which has at least 80%, 85%, 90%, 91%, 92%, 93%, 94%, 95%, 96%, 97%, 98% or 99% identity with one of the amino acid sequences in accordance with (d), or (f) which comprises a part sequence of a nucleic acid in accordance with (a) to (e). In a preferred embodiment, the polynucleotide is characterized in that it comprises a nucleic acid molecule which (aa) comprises a nucleotide sequence in accordance with SEQ ID NO: 1 or 5, (bb) comprises a nucleotide sequence with an identity of at least 80%, 85%, 90%, 91%, 92%, 93%, 94%, 95%, 96%, 97%, 98% or 99% with one of the nucleotide sequences in accordance with SEQ ID NO: 1 or 5, preferably over the entire length of the sequence, (cc) which hybridizes with the complementary strand of a nucleic acid molecule in accordance with (aa) or (bb) under stringent conditions, (dd) which codes for a polypeptide with an amino acid sequence in accordance with SEQ ID NO: 2 or 6, (ee) which codes for a polypeptide with an amino acid sequence which has at least 80%, 85%, 90%, 91%, 92%, 93%, 94%, 95%, 96%, 97%, 98% or 99% A identity with one of the amino acid sequences in accordance with (dd), or (ff) which comprises a part sequence of a nucleic acid in accordance with (aa) to (ee). The expression "part sequence of a nucleic acid molecule" as used in the present invention may be at least 20, 30, 40, 50, 60, 70, 80, 90 or at least 100 successive nucleotides, furthermore at least 150, 200, 250, 300, 350, 400, 450, 500, 600, 700, 800, 900 or 1000 successive nucleotides. The polynucleotide may be in the heterozygous or homozygous state in the genome of the maize plant of the invention; preferably, the polynucleotide is in the homozygous state.

TABLE 1

Potential resistance-conferring genes of the HTN1 locus from *Pepitilla*; Gene name (column 1); reference to corresponding SEQ ID Nos in the genomic exon sequence (column 2); reference to corresponding SEQ ID Nos in the predicted amino acid/protein sequence (column 3); annotated homologous gene from the B73 reference genome (column 4).

| Gene name | cDNA SEQ ID NO: | Protein sequence SEQ ID NO: | Homologous B73 gene |
|---|---|---|---|
| RLK1 | 1 | 2 | GRMZM2G451147 |
| RLK4 | 3 | 4 | GRMZM2G144028 |
| EXT1 | 5 | 6 | GRMZM2G445338 |
| DUF1 | 7 | 8 | AC209075.3_FG007 |
| ZNF1 | 9 | 10 | GRMZM2G175661 |
| CYT1 | 11 | 12 | GRMZM2G092018 |
| RET1 | 13 | 14 | GRMZM2G091973 |
| HYD | 15 | 16 | GRMZM2G144021 |

Furthermore, the first interval in the chromosome fragment which exhibits donor alleles in accordance with the haplotype in Table 2 is characterized by the sequence of donor alleles in the haplotype of Table 2, but is not limited to this sequence of donor alleles in accordance with Table 2. This means that the first interval exhibits at least the donor allele which describes the resistance-conferring gene from Table 1, optionally with the donor allele of the marker MA0008. Furthermore, the first interval preferably exhibits at least the donor alleles in accordance with the haplotype of Table 2 from MA0021 to MA0022 (i.e. MA0021, MA0007, MA0008, MA0009, MA0010, MA0011, MA0012, MA0022) or from MA0005 to MA0022 (i.e. MA0005, MA0021, MA0007, MA0008, MA0009, MA0010, MA0011, MA0012 and MA0022) or from MA0005 to MA0013 (i.e. MA0005, MA0021, MA0007, MA0008, MA0009, MA0010, MA0011, MA0012, MA0022 and MA0013) or from MA0005 to MA0014 (i.e. MA0005, MA0021, MA0007, MA0008, MA0009, MA0010, MA0011, MA0012, MA0022, MA0013 and MA0014) or from MA0005 to MA0015 (i.e. MA0005, MA0021, MA0007, MA0008, MA0009, MA0010, MA0011, MA0012, MA0022, MA0013, MA0014 and MA0015) or from MA0005 to MA0016 (i.e. MA0005, MA0021, MA0007, MA0008, MA0009, MA0010, MA0011, MA0012, MA0022, MA0013, MA0014, MA0015 and MA0016), particularly preferably from MA0005 to MA0017 (i.e. MA0005, MA0021, MA0007, MA0008, MA0009, MA0010, MA0011, MA0012, MA0022, MA0013, MA0014, MA0015, MA0016 and MA0017), MA0005 to MA0018 (i.e. MA0005, MA0021, MA0007, MA0008, MA0009, MA0010, MA0011, MA0012, MA0022, MA0013, MA0014, MA0015, MA0016, MA0017 and MA0018), MA0005 to PZE-108095998 (i.e. MA0005, MA0021, MA0007, MA0008, MA0009, MA0010, MA0011, MA0012, MA0022, MA0013, MA0014, MA0015, MA0016, MA0017, MA0018 and PZE-108095998), MA0005 to PZE-108096011 (i.e. MA0005, MA0021, MA0007, MA0008, MA0009, MA0010, MA0011, MA0012, MA0022, MA0013, MA0014, MA0015, MA0016, MA0017, MA0018, PZE-108095998 and PZE-108096011) or MA0005 to MA0019 (i.e. MA0005, MA0021, MA0007, MA0008, MA0009, MA0010, MA0011, MA0012, MA0022, MA0013, MA0014, MA0015, MA0016, MA0017, MA0018, PZE-108095998, PZE-108096011 and MA0019), more particularly preferably from MA0005 to PZE-108096610 (i.e. MA0005, MA0021, MA0007, MA0008, MA0009, MA0010, MA0011, MA0012, MA0022, MA0013, MA0014, MA0015, MA0016, MA0017, MA0018, PZE-108095998, PZE-108096011, MA0019 and PZE-108096610), MA0005 to MA0020 (i.e. MA0005, MA0021, MA0007, MA0008, MA0009, MA0010, MA0011, MA0012, MA0022, MA0013, MA0014, MA0015, MA0016, MA0017, MA0018, PZE-108095998, PZE-108096011, MA0019, PZE-108096610 and MA0020), MA0005 to PZE-108096791 (i.e. MA0005, MA0021, MA0007, MA0008, MA0009, MA0010, MA0011, MA0012, MA0022, MA0013, MA0014, MA0015, MA0016, MA0017, MA0018, PZE-108095998, PZE-108096011, MA0019, PZE-108096610, MA0020 and PZE-108096791) or MA0005 to MA0006 (i.e. MA0005, MA0021, MA0007, MA0008, MA0009, MA0010, MA0011, MA0012, MA0022, MA0013, MA0014, MA0015, MA0016, MA0017, MA0018, PZE-108095998, PZE-108096011, MA0019, PZE-108096610, MA0020, PZE-108096791 and MA0006). This resistant haplotype unequivocally specifies and identifies the resistance source Pepitilla. In particular, the first interval is localized between the markers MA0004 and PZE-108097482, between the markers MA0004 and MA0022, between the markers MA0005 and PZE-108097482 or between the markers MA0005 and MA0022. Preferably, the first interval describes a segment of the chromosome fragment which can confer the resistance typical of HTN1. As such it is a carrier of the polynucleotide cited above.

TABLE 2

Resistant haplotype from B37HTN1;

| Position in bp on B73 AGPv02 | Allele donor B37HTN1 | Marker designation |
| --- | --- | --- |
| 151831049 | C | MA0005 |
| 151907173 | G | MA0021 |
| 152045106 | T | MA0007 |
| 152045141 | T | MA0008 |
| 152045402 | T | MA0009 |
| 152045516 | C | MA0010 |
| 152045912 | T | MA0011 |
| 152046502 | T | MA0012 |
| 152046529 | A | MA0022 |
| 152133057 | G | MA0013 |
| 152133380 | A | MA0014 |
| 152144310 | A | MA0015 |
| 152250992 | A | MA0016 |
| 152301656 | A | MA0017 |
| 152304127 | A | MA0018 |
| 152433358 | A | PZE-108095998 |
| 152435855 | A | PZE-108096011 |
| 152630794 | C | MA0019 |
| 152703579 | G | PZE-108096610 |
| 152753635 | A | MA0020 |
| 152887338 | G | PZE-108096791 |
| 152888374 | A | MA0006 |

Furthermore, every maize plant in accordance with the invention is a HT-resistant maize plant. The HT resistance conferred by integration of the chromosome fragment may be quantified by determining classification scores in phenotyping experiments in accordance with the scheme in Table 3 and Example 1.A); in this, the resistance level reduces from 1 to 9. HT-resistant maize plants in accordance with the invention exhibit an increased resistance to *H. turcicum* of at least 1 classification score, preferably at least 2 classification scores or at least 3 classification scores and particularly preferably at least 4 classification scores. Preferably, a maize plant in accordance with the invention exhibits resistance to at least one race of *Helminthosporium turcicum* which does not correspond to the known race specificity known in the prior art. In a particularly preferred embodiment, a maize plant in accordance with the invention is resistant to all known races of *Helminthosporium turcicum*, i.e. the conferred resistance is not race-specific and may be particularly advantageous in the formation of a broad resistance to *Helminthosporium turcicum*.

TABLE 3

Classification score scheme for phenotyping experiments in field trials at various locations with natural and artificial *H. turcicum* inoculation (from the Deutsche Maiskomitee (DMK, German maize committee); AG variety 27.02.02; (DMK J. Rath; RP Freiburg H. J. Imgraben)

| Classification score | Phenotype |
| --- | --- |
| 1 | Plants exhibit no symptoms of disease, 0% |
| 2 | Beginning of infestation, first small spots (less than 2 cm) visible. Less than 5% of leaf surface affected. |
| 3 | Some spots have developed on a leaf stage. Between 5-10% of leaf surface affected. |
| 4 | 10-20% of leaf surface affected. Clearly visible spots on several leaf stages. |
| 5 | 20-40% of leaf surface affected. Spots start to coalesce. |
| 6 | 40-60% of leaf surface affected. Systematic infestation visible on leaves. |
| 7 | 60-80% of leaf surface affected. Approximately half of leaves destroyed or dried out because of fungal infestation. |
| 8 | 80-90% of leaf surface affected. More than half of leaves destroyed or dried out because of fungal infestation. |
| 9 | 90-100% of leaf surface affected. The plants are almost completely dried out. |

The description discloses the genetic or molecular structure of the HTN1 locus by providing a haplotype, by mapping prominent markers and also by identifying candidate genes for conferring resistance to the pathogen *Helminthosporium turcicum*.

Surprisingly, the maize plants in accordance with the invention proved to be agronomic in phenotyping experiments carried out in the field and in the greenhouse. This is because, while other converted lines from a breeding programme for integration of the HTN1 locus from Pepitilla as well as from known prior art converted lines such as B37HTN1, in addition to the conferred HT resistance under non-infestation conditions with *H. turcicum* and under comparable environmental conditions (temperature, nutrient supply, location etc) exhibited a significant delay in the male and/or female flowering time compared with the corresponding line without introgression (for example isogenic lines or original lines), in the maize plant of the invention the flowering time corresponded to that of a comparative isogenic maize plant into the genome of which a chromosome fragment from the donor Pepitilla had not been integrated. The "flowering times" correspond when they differ from each other by less than 2 days. The magnitude of the observed delay in this case is strongly dependent on the species of maize or the maize genotype, the prevailing environmental conditions such as the soil condition, humidity, precipitation, temperature etc and/or biotic stress such as pathogen infestation other than with *H. turcicum*. The delay was at least 2 days, at least 3 days, at least 5 days or at least 7 days. This established difference in the flowering time is due to linkage drag as part of the introgression, which is particularly surprising since observations of this type are not known in the prior art. The flowering time is an important agronomic feature. It can directly and substantially influence the yield potential of a maize plant. A delayed flowering time usually results in a reduced yield.

Figure 3:
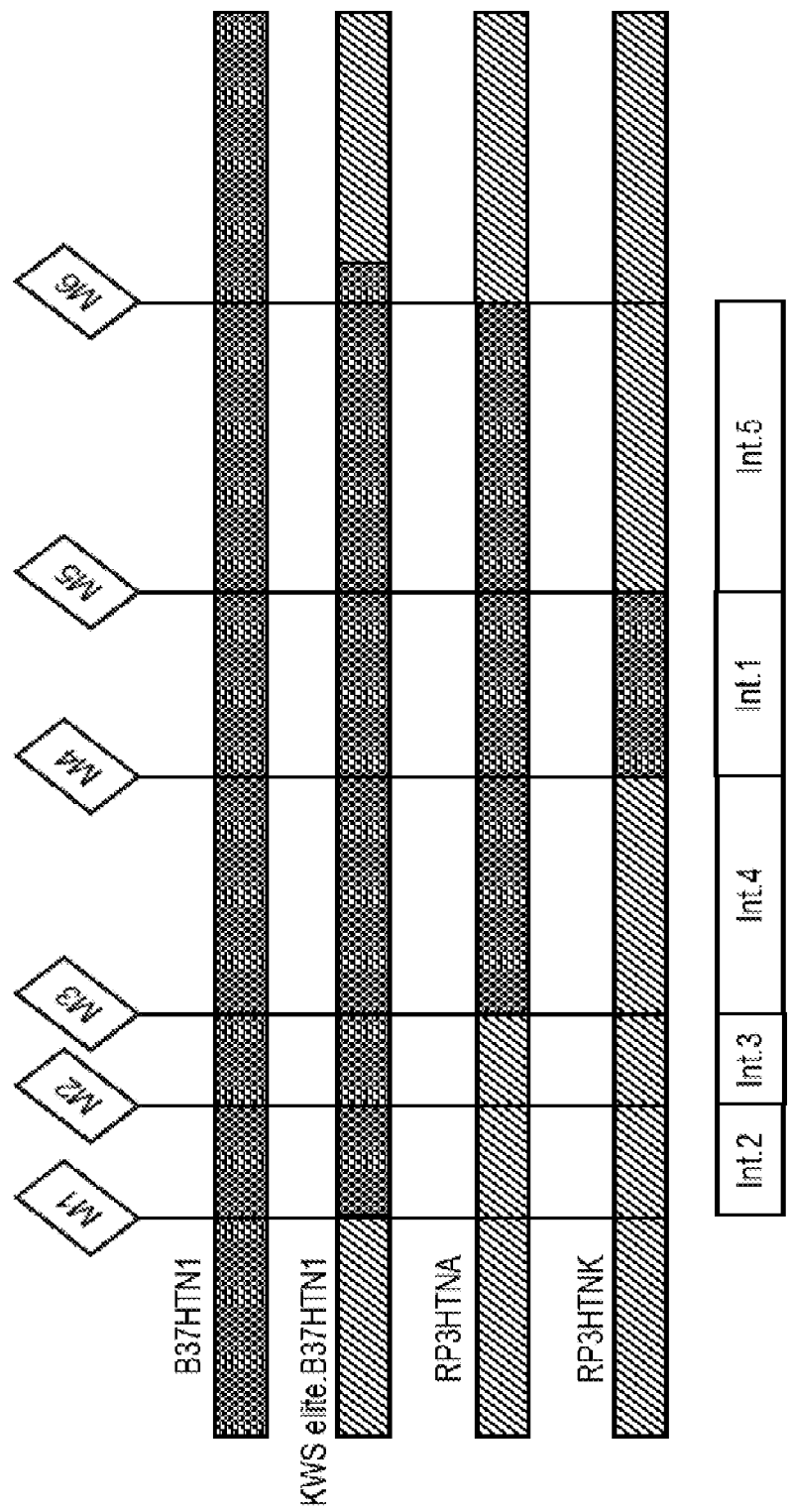

In order to elucidate the genetic cause of this disadvantage and to identify the linkage drag, extensive backcrossing programmes accompanied by genotyping and phenotyping were carried out, for example. The work was supported by intensive development of specific molecular markers on the chromosome fragment carrying the HTN1. The techniques of marker aided selection (MAS) and carrying out focused backcross programmes (for example "map based cloning") can be found in the prior art (Gupta & Varshney, 2013). The QTL with HTN1 resistance from the donor B37HTN1 or Pepitilla was localized with the aid of the SSR markers bnlg1067, umc1121, MA0002, MA0003, bnlg1782, umc1287, umc1960 and bnIg240 in the descendants on chromosome 8 (bin 8.06) between the markers MA0002 (Table 4) and umc1287 (Table 5) in a region of 23.1 cM (see FIG. 1). In maize plants with the delayed flowering time, the locus of the genomic donor sequence segment which is responsible for the identified linkage drag of the flowering time was successfully determined to be on a further second interval of the donor on the chromosome fragment (Example 3B; FIG. 3). In a maize plant in accordance with the invention, a chromosome fragment is integrated into it which does not contain the second interval of the donor. Here, the second interval stems, for example, from a recurrent parent which does not carry the linkage drag for flowering time or from an exogenically introduced homologous DNA fragment which is not a carrier of the linkage drag, on a suitable donor vector for targeted homologous recombination. The second interval is proximal and closely coupled to the resistance locus HTN1 or to the first interval. The second interval is an interval between a marker in a first marker region (M1) which is flanked by the markers SYN14136 and PZE-108076510 and a marker in a second marker region (M2) which is flanked by the markers SYN24931 and PZE-108077560. The flanking markers may be discerned from Table 4. The markers SYN14136, PZE-108076510, SYN24931 and PZE-108077560 are SNP markers for use in the KBioscience-KASP system (www.lgcgenomics.com). They clearly define the marker regions M1 and M2 either side of the sequence segment which in the donor B37HTN1 or Pepitilla carry the linkage drag for flowering time. Moreover, as the polymorphic marker, these are also capable of differentiating between Pepitilla donor alleles and, for example, the allele for the recurrent parent. All details regarding the use of these markers as a KASP marker can be obtained from Table 4. Suitable exemplary primer hybridization parameters for the PCR are provided in Example 2. A person skilled in the art is, moreover, also capable of determining other suitable hybridization parameters. Furthermore, it is routine for a person skilled in the art with a knowledge of the described marker regions in addition to the cited markers to develop other markers, in particular polymorphic markers, in M1 and/or M2. Using the markers cited here, namely SYN14136, PZE-108076510, SYN24931 and PZE-108077560 or self-developed markers in M1 and/or M2, the person skilled in the art will readily be able to establish whether in a maize plant into the genome of which a chromosome fragment with HTN1 resistance locus from the donor Pepitilla has been integrated, the second interval of the donor described above is contained therein or not contained therein. The person skilled in the art will also be aware that, for example, during the course of a breeding process or a genetic engineering strategy for targeted recombination, a chromosome interval can be removed from the donor which, for example, comprises genomic sequences which cause linkage drag, by genetic/homologous recombination of the integrated chromosome fragment. In this regard, the interval of the Pepitilla donor can be replaced by the corresponding interval of the recurrent parent genome or by an exogenically introduced homologous DNA fragment. Markers in general and the markers disclosed here in particular can in particular be used for selection in this regard. As an example, a possible use of markers for the detection of an allele will be given below: detecting an allele may, for example, be carried out by (a) isolating at least one nucleic acid molecule from a genome of a plant or a plant cell/maize plant or maize plant cell, and (b) examining the isolated nucleic acid molecule with at least one marker, as well as optionally (c) sequencing the allele in one and/or more genotypes, (d) detecting one and/or more polymorphisms and/or (e) restriction with a restriction endonuclease which can produce fragments of different sizes at a marker allele.

A preferred embodiment of the maize plant of the invention is a maize plant as described above, wherein the chromosome fragment does not contain the second interval of the donor which is flanked a) by the markers SYN14136 and PZE-108077560, b) by the markers PZE-108076510 and PZE-108077560, c) by the markers SYN14136 and SYN24931 or d) by the markers PZE-108076510 and SYN24931.

In a preferred embodiment, the maize plant of the invention exhibits a deviant male and/or female flowering time compared with the Pepitilla-converted line or Pepitilla-converted plant such as B37HTN1 which contains the interval 2 between a marker in a first marker region (M1) which is flanked by the markers SYN14136 and PZE-108076510, and by a marker in a second marker region (M2) which is flanked by the markers SYN24931 and PZE-108077560, wherein the term "deviant time" means that the converted line or converted plant exhibits a delay of at least 2 days, at least 3 days, at least 5 days or at least 7 days.

A further preferred embodiment of the maize plant of the invention is a maize plant as described above, wherein the chromosome fragment furthermore does not contain an interval of the donor (hereinafter termed the third interval or interval 3) between a marker in the second marker region M2 and a marker in a third marker region M3 which is flanked by the markers PZE-108093423 (Table 4) and PZE-108093748 (Table 4). The markers PZE-108093423 and PZE-108093748 are SNP markers for use in the KBioscience-KASP-System (www.lgcgenomics.com). They unequivocally define the marker region M3. As polymorphic markers, they are also suitable for distinguishing between donor alleles and, for example, the allele for the recurrent parent. All details regarding the use of these markers as KASP markers can be obtained from Table 4. Suitable exemplary primer hybridization parameters for PCR are provided in Example 2. A person skilled in the art is also able to determine other suitable hybridization parameters. Furthermore, it is a routine matter for a person skilled in the art with a knowledge of the described marker region to develop other markers, in particular polymorphic markers, in M3 in addition to the cited markers. Using the markers for M2 as cited above and the markers PZE-108093423 and PZE-108093748 noted herein or self-developed markers in M3, it would be a simple matter for a person skilled in the art to establish whether, in a maize plant into the genome of which a chromosome fragment with a HTN1 resistance locus from the donor Pepitilla has been integrated, contains or does not contain the third interval of the donor as described above.

A further preferred embodiment of the maize plant in accordance with the invention is provided by the maize plant as described above wherein the chromosome fragment does not contain a genetic segment which comprises the second interval and the third interval of the donor and is flanked a) by the markers SYN14136 and PZE-108093423, b) by the markers PZE-108076510 and PZE-108093423, c) by the markers SYN14136 and PZE-108093748 or d) by the markers PZE-108076510 and PZE-108093748.

In a further aspect, further genetic segments may be determined on the chromosome fragment which, under non infestation conditions with *H. turcicum*, could cause a significant negative influence on the yield potential of a maize plant into the genome of which a chromosome fragment with a HTN1 resistance locus from the donor Pepitilla has been integrated. Thus, independently of the delay to the flowering time described above, converted lines as well as known prior art converted lines such as B37HTN1, in addition to the conferred HT resistance, exhibit a substantially reduced yield, in particular a substantially reduced silage yield compared with the corresponding line without introgression (for example isogenic line or original line). This is the case even for lines into the genome of which a genetic segment of the donor consisting of interval 2 (between a marker from M1 and M2) or interval 2 and 3 (between a marker from M1 and M3) is no longer present. Observations of this type would not be expected by the person skilled in the art, since there would be no indication in the prior art of a linkage drag of this type in HTN1 introgression lines. In order to elucidate the genetic cause of this agronomic disadvantage, for example, extended backcrossing programmes accompanied by genotyping and phenotyping were carried out. This work was supported by an intensive development of more accurate and more specific molecular markers on the HTN1-carrying chromosome fragment. In maize plants with the reduced yield (silage yield), the position of the genomic sequence segment which is responsible for the linkage drag of the silage yield was successfully determined on two further intervals of the donor (hereinafter the fourth interval or interval 4 and the fifth interval or interval 5) on the Pepitilla chromosome fragment (Example 3C; FIG. 3). A maize plant in accordance with the invention which comprises a corresponding interval without linkage drag, for example from the recurrent parent, instead of the fourth and/or fifth interval of the donor carrying the linkage drag, exhibits no reduced silage yield, and thus a yield, in particular a silage yield, which is the same as or comparable to a line without introgression (for example isogenic line or original line). Compared with a comparable maize plant with linkage drag for the silage yield, the silage yield of a maize plant in accordance with the invention without fourth and/or fifth intervals of the donors, may be more than 2%, 3%, 4%, 5%, 6%, 7%, 8%, 9%, 10%, 15% or 20% higher. The fourth interval is proximally located and closely coupled to the resistance locus HTN1 or the first interval. The fifth interval is distally located and closely coupled with the resistance locus HTN1 or the first interval.

Thus, a particularly preferred embodiment of the maize plant of the invention is a maize plant as described above wherein the chromosome fragment furthermore does not contain i) the fourth interval of the donor between a marker in the third marker region M3 and a marker in a fourth marker region M4 which is flanked by the markers MA0004 and MA0005, or ii) a genetic segment with the fourth interval between a marker in the third marker region M3 and a marker in a seventh marker region M7 which is flanked by the markers MA0005 and MA0021, and/or wherein the chromosome fragment furthermore does not contain i) the fifth interval of the donor between a marker in a fifth marker region M5 which is flanked by the markers MA0006 and PZE-108097482 and a marker in a sixth marker region M6 which is flanked by the markers PZE-108107671 and SYN4196, or ii) a genetic segment with the fifth interval between a marker in an eighth marker region M8 which is flanked by the markers MA0022 and MA0013 and a marker in a sixth marker region M6 which is flanked by the markers PZE-108107671 and SYN4196. The flanking markers may be obtained from Table 4. The markers MA0004, MA0005, MA0006, MA0013, MA0021, MA0022, PZE-108097482, PZE-108107671 and SYN4196 are SNP markers for use in the KBioscience-KASP system (www.lgcgenomics.com). They unequivocally define the marker regions M4, M5, M6, M7 and M8 which, together with M3, establish the sequence segments which carry the linkage drag for silage yield in the donor B37HTN1 or Pepitilla. As polymorphic markers, they are also suitable for distinguishing between donor alleles and, for example, the allele for the recurrent parent. All details regarding the use of these markers as KASP markers can be obtained from Table 4. Suitable exemplary primer hybridization parameters for PCR are provided in Example 2. A person skilled in the art is also able to determine other suitable hybridization parameters. Furthermore, it is a routine matter for a person skilled in the art with a knowledge of the described marker region to develop other markers, in particular polymorphic markers, in M4, in M5, in M6, in M7 and/or in M8. Using the markers MA0004, MA0005, MA0006, MA0013, MA0021, MA0022, PZE-108097482, PZE-108107671 and SYN4196 described here or self-developed markers in M4, in M5, in M6, in M7 and/or M8 together with the markers in M3 described above, it would be a simple matter for a person skilled in the art to establish whether, in a maize plant into the genome of which a chromosome fragment with a HTN1 resistance locus from the donor Pepitilla has been integrated, contains or does not contain the fourth interval of the donor as described above.

A further particularly preferred embodiment of the maize plant of the invention is a maize plant as described above wherein the chromosome fragment i) does not contain a genetic segment which comprises the second interval, the third interval and the fourth interval of the donor and is flanked a) by the markers SYN14136 and MA0004, b) by the markers PZE-108076510 and MA0004, c) by the markers SYN14136 and MA0005 or d) by the markers PZE-108076510 and MA0005, or (ii) does not contain a genetic segment which comprises the second interval and the third interval of the donor and is flanked a) by the markers SYN14136 and PZE-108093423, b) by the markers PZE-108076510 and PZE-108093423, c) by the markers SYN14136 and PZE-108093748 or d) by the markers PZE-108076510 and PZE-108093748, and the fifth interval of the donor, or (iii) does not contain a genetic segment which comprises the second interval, the third interval and the fourth interval of the donor and is flanked a) by the markers SYN14136 and MA0004, b) by the markers PZE-108076510 and MA0004, c) by the markers SYN14136 and MA0005 or d) by the markers PZE-108076510 and MA0005, and the fifth interval of the donor.

A further particularly preferred embodiment of the maize plant in accordance with the invention is a maize plant as described above, wherein the chromosome fragment comprises (i) does not contain a genetic segment which comprises the second interval, the third interval and the fourth interval of the donor and is flanked a) by the markers SYN14136 and MA0021 or b) by the markers PZE-108076510 and MA0021, or (ii) does not contain a genetic segment which comprises the second interval, the third interval and the fourth interval of the donor and is flanked a) by the markers SYN14136 and MA0021 or b) by the markers PZE-108076510 and MA0021, and the fifth interval of the donor, or (iii) does not contain a genetic segment which comprises the second interval, the third interval and the fourth interval of the donor and is flanked a) by the markers SYN14136 and MA0021 or b) by the markers PZE-108076510 and MA0021, and a second genetic segment which comprises the fifth interval of the donor and is flanked a) by the markers MA0022 and PZE-108107671, b) by the markers MA0022 and SYN4196, c) by the markers MA0013 and PZE-108107671 or by the markers MA0013 and SYN4196, or (iv) does not contain a genetic segment which comprises the second interval and the third interval of the donor and is flanked a) by the markers SYN14136 and PZE-108093423, b) by the markers PZE-108076510 and PZE-108093423, c) by the markers SYN14136 and PZE-108093748 or d) by the markers PZE-108076510 and PZE-108093748, and a second genetic segment which comprises the fifth interval of the donor and is flanked a) by the markers MA0022 and PZE-108107671, b) by the markers MA0022 and SYN4196, c) by the markers MA0013 and PZE-108107671 or by the markers MA0013 and SYN4196, or (v) does not contain a genetic segment which comprises the second interval, the third interval and the fourth interval of the donor and is flanked a) by the markers SYN14136 and MA0021 or b) by the markers PZE-108076510 and MA0021, and a second genetic segment which comprises the fifth interval of the donor and is flanked a) by the markers MA0022 and PZE-108107671, b) by the markers MA0022 and SYN4196, c) by the markers MA0013 and PZE-108107671 or by the markers MA0013 and SYN4196.

The object forming the basis of the present invention is accomplished in an alternative manner by means of a maize plant into the genome of which a chromosome fragment from the donor Pepitilla has been integrated, wherein the chromosome fragment comprises the first interval of the donor which exhibits donor alleles in accordance with the haplotype of Table 2 and comprises the polynucleotide which confers resistance against *Helminthosporium turcicum*, and wherein the chromosome fragment does not contain i) the fourth interval of the donor between a marker in the third marker region which is flanked by the markers PZE-108093423 and PZE-108093748, and a marker in the fourth marker region which is flanked by the markers MA0004 and MA0005, or ii) a genetic segment with the fourth interval between a marker in the third marker region M3 and a marker in the seventh marker region M7 which is flanked by the markers MA0005 and MA0021. The above description, for example, as regards markers the polynucleotide or the phenotyping is also valid in this case and for every other alternative solution to the problem, as well as disclosed embodiments.

A preferred embodiment of this inventive maize plant is a maize plant as described above, wherein the chromosome fragment i) does not contain the fourth interval of the donor which is flanked a) by the markers PZE-108093423 and MA0004, b) by the markers PZE-108093748 and MA0004, c) by the markers PZE-108093423 and MA0005 or d) by the markers PZE-108093748 and MA0005, or ii) does not contain a genetic segment which comprises the fourth interval of the donor and is flanked a) by the markers PZE-108093423 and MA0021 or b) by the markers PZE-108093748 and MA0021.

A further preferred embodiment of the maize plant in accordance with the invention is a maize plant as hereinbefore described, wherein the chromosome fragment furthermore does not contain the third interval of the donor between a marker in the second marker region M2 and by a marker in the third marker region M3.

A further preferred embodiment of the maize plant in accordance with the invention is a maize plant as described above, wherein the chromosome fragment does not contain a genetic segment which comprises the third interval and the fourth interval of the donor and is flanked a) by the markers SYN24931 and MA0004, b) by the markers PZE-108077560 and MA0004, c) by the markers SYN24931 and MA0005, d) by the markers PZE-108077560 and MA0005, e) by the markers SYN24931 and MA0021 or f) by the markers PZE-108077560 and MA0021.

A further preferred embodiment of the maize plant in accordance with the invention is a maize plant as hereinbefore described, wherein the chromosome fragment i) furthermore does not contain the fifth interval of the donor between a marker in the fifth marker region M5 and a marker in the sixth marker region M6 or ii) does not contain a genetic segment with the fifth interval between a marker in the eighth marker region M8 and a marker in the sixth marker region M6.

A further particularly preferred embodiment of the maize plant in accordance with the invention is a maize plant as hereinbefore described, wherein the chromosome fragment i) does not contain a genetic segment which comprises the third interval and the fourth interval of the donor and is flanked a) by the markers SYN24931 and MA0004, b) by the markers PZE-108077560 and MA0004, c) by the markers SYN24931 and MA0005 or d) by the markers PZE-108077560 and MA0005, and the fifth interval, or ii) does not contain a genetic segment which comprises the third interval and the fourth interval of the donor and is flanked a) by the markers SYN24931 and MA0004, b) by the markers PZE-108077560 and MA0004, c) by the markers SYN24931 and MA0005 or d) by the markers PZE-108077560 and MA0005, and a second genetic segment which comprises the fifth interval and is flanked a) by the markers MA0022 and SYN4196, b) by the markers MA0022 and PZE-108107671, c) by the markers MA0013 and SYN4196 or by the markers MA0013 and PZE-108107671.

A further particularly preferred embodiment of the maize plant in accordance with the invention is a maize plant as hereinbefore described, wherein the chromosome fragment i) does not contain a genetic segment which comprises the third interval and the fourth interval of the donor and is flanked a) by the markers SYN24931 and MA00021 or b) by the markers PZE-108077560 and MA00021, and the fifth interval, or ii) does not contain a genetic segment which comprises the third interval and the fourth interval of the donor and is flanked a) by the markers SYN24931 and MA00021 or b) by the markers PZE-108077560 and MA00021, and a second genetic segment which comprises the fifth interval and is flanked a) by the markers MA0022 and PZE-108107671, b) by the markers MA0022 and SYN4196, c) by the markers MA0013 and PZE-108107671 or by the markers MA0013 and SYN4196.

Alternatively, the object of the present invention is further accomplished by means of a maize plant, into the genome of which has a chromosome fragment from the donor Pepitilla has been integrated, wherein the chromosome fragment comprises the first interval of the donor which exhibits donor alleles in accordance with the haplotype of Table 2 and which comprises the polynucleotide which confers resistance against *Helminthosporium turcicum* in the maize plant, and wherein the chromosome fragment does not contain i) the fifth interval of the donor between a marker in the fifth marker region which is flanked by the markers MA0006 and PZE-108097482, and a marker in the sixth marker region which is flanked by the markers PZE-108107671 and SYN4196, or ii) a genetic segment with the fifth interval between a marker in the eighth marker region M8 which is flanked by the markers MA0022 and MA0013, and by a marker in the sixth marker region M6 which is flanked by the markers PZE-108107671 and SYN4196.

A further preferred embodiment of the maize plant in accordance with the invention is a maize plant as hereinbefore described, wherein the chromosome fragment furthermore does not contain the third interval of the donor between a marker in the second marker region M2 and a marker in the third marker region M3.

A further particularly preferred embodiment of the maize plant in accordance with the inventions is a maize plant as described above, wherein the chromosome fragment is flanked a) by a marker in the second marker region M2 and by a marker in the sixth marker region M6, b) by a marker in the third marker region M3 and by a marker in the sixth marker region M6, c) by a marker in the fourth marker region M4 and by a marker in the sixth marker region M6, d) by a marker in the seventh marker region M7 and by a marker in the sixth marker region M6, e) by a marker in the marker region M1 and by a marker in the marker region M5, f) by a marker in the second marker region M2 and by a marker in the fifth marker region M5, g) by a marker in the third marker region M3 and by a marker in the fifth marker region M5, h) by a marker in the fourth marker region M4 and by a marker in the fifth marker region M5, i) by a marker in the seventh marker region M7 and by a marker in the fifth marker region M5, j) by a marker in the marker region M1 and by a marker in the marker region M8, k) by a marker in the second marker region M2 and by a marker in the eighth marker region M8, l) by a marker in the third marker region M3 and by a marker in the eighth marker region M8, m) by a marker in the fourth marker region M4 and by a marker in the eighth marker region M8, or n) by a marker in the seventh marker region M7 and by a marker in the eighth marker region M8.

A further particularly preferred embodiment of the maize plant in accordance with the invention is a maize plant as described above, wherein the chromosome fragment is flanked a) by the markers SYN24931 and SYN4196, b) by the markers PZE-108077560 and SYN4196, c) by the markers SYN24931 and PZE-108107671, d) by the markers PZE-108077560 and PZE-108107671, e) by the markers PZE-108093423 and SYN4196, f) by the markers PZE-108093748 and SYN4196, g) by the markers PZE-108093423 and PZE-108107671, h) by the markers PZE-108093748 and PZE-108107671, i) by the markers MA0004 and SYN4196, j) by the markers MA0005 and SYN4196, k) by the markers MA0004 and PZE-108107671, l) by the markers MA0005 and PZE-108107671, m) by the markers MA0021 and SYN4196, n) by the markers MA0021 and PZE-108107671, o) by the markers PZE-108076510 and MA0006, p) by the markers SYN14136 and MA0006, q) by the markers PZE-108076510 and PZE-108097482, r) by the markers SYN14136 and PZE-108097482, s) by the markers SYN24931 and PZE-108097482, t) by the markers PZE-108077560 and PZE-108097482, u) by the markers SYN24931 and MA0006, v) by the markers PZE-108077560 and MA0006, w) by the markers PZE-108093423 and PZE-108097482, x) by the markers PZE-108093748 and PZE-108097482, y) by the markers PZE-108093423 and MA0006, z) by the markers PZE-108093748 and MA0006, aa) by the markers MA0004 and PZE-108097482, ab) by the markers MA0005 and PZE-108097482, ac) by the markers MA0004 and MA0006, ad) by the markers MA0005 and MA0006, ae) by the markers MA0021 and PZE-108097482, af) by the markers MA0021 and MA0006, ag) by the markers PZE-108076510 and MA0013, ah) by the markers SYN14136 and MA0013, ai) by the markers PZE-108076510 and MA0022, aj) by the markers SYN14136 and MA0022, ak) by the markers SYN24931 and MA0013, al) by the markers PZE-108077560 and MA0013, am) by the markers SYN24931 and MA0022, an) by the markers PZE-108077560 and MA0022, ao) by the markers PZE-108093423 and MA0013, ap) by the markers PZE-108093748 and MA0013, aq) by the markers PZE-108093423 and MA0022, ar) by the markers PZE-108093748 and MA0022, as) by the markers MA0004 and MA0013, at) by the markers MA0005 and MA0013, au) by the markers MA0004 and MA0022, av) by the markers MA0005 and MA0022, aw) by the markers MA0021 and MA0013, ax) by the markers MA0021 and MA0022.

A further particularly preferred embodiment of the maize plant in accordance with the inventions is a maize plant as described above, wherein the chromosome fragment is localized a) between a marker in the second marker region M2 and a marker in the sixth marker region M6, b) between a marker in the third marker region M3 and a marker in the sixth marker region M6, c) between a marker in the fourth marker region M4 and a marker in the sixth marker region M6, d) between a marker in the seventh marker region M7 and a marker in the sixth marker region M6, e) between a marker in the first marker region M1 and a marker in the fifth marker region M5 f) between a marker in the second marker region M2 and a marker in the fifth marker region M5, g) between a marker in the third marker region M3 and a marker in the fifth marker region M5, h) between a marker in the fourth marker region M4 and a marker in the fifth marker region M5, i) between a marker in the seventh marker region M7 and a marker in the fifth marker region M5, j) between a marker in the marker region M1 and a marker in the marker region M8, k) between a marker in the second marker region M2 and a marker in the eighth marker region M8, l) between a marker in the third marker region M3 and a marker in the eighth marker region M8, m) between a marker in the fourth marker region M4 and a marker in the eighth marker region M8, or n) between a marker in the seventh marker region M7 and a marker in the eighth marker region M8.

TABLE 4

KASP marker primer sequences and assignment to B37HTN1 donor alleles derived from the landrace Pepitilla (allele X and allele Y: describe the biallelic values of the SNPs)

| SNP marker | Marker position AGPv02 [bp] | Primer alleles X(5'-3') [SEQ ID NO] | Primer alleles Y(5'-3') [SEQ ID NO] | Common primer (5'-3') [SEQ ID NO] | B37HTN1 donor alleles (SNP) | Marker region |
|---|---|---|---|---|---|---|
| SYN14136 | 131681497 | 17 | 18 | 19 | A | M1 |
| PZE-108076510 | 131905855 | 20 | 21 | 22 | G | M1 |

TABLE 4-continued

KASP marker primer sequences and assignment to B37HTN1 donor alleles derived from the
landrace Pepitilla (allele X and allele Y: describe the biallelic values of the SNPs)

| SNP marker | Marker position AGPv02 [bp] | Primer alleles X(5'-3') [SEQ ID NO] | Primer alleles Y(5'-3') [SEQ ID NO] | Common primer (5'-3') [SEQ ID NO] | B37HTN1 donor alleles (SNP) | Marker region |
|---|---|---|---|---|---|---|
| SYN24931 | 132877982 | 23 | 24 | 25 | A | M2 |
| PZE-108077560 | 133189880 | 26 | 27 | 28 | A | M2 |
| PZE-108093423 | 150279048 | 29 | 30 | 31 | A | M3 |
| PZE-108093748 | 150562764 | 32 | 33 | 34 | G | M3 |
| PZE-108107671 | 161543406 | 35 | 36 | 37 | C | M6 |
| SYN4196 | 161766769 | 38 | 39 | 40 | C | M6 |
| MA0004 | 151688652 | 41 | 42 | 43 | A | M4 |
| MA0005 | 151831049 | 44 | 45 | 46 | C | M4/M7 |
| MA0021 | 151907173 | 241 | 242 | 243 | G | M7 |
| MA0006 | 152888310 | 47 | 48 | 49 | A | M5 |
| PZE-108097482 | 153139646 | 50 | 51 | 52 | A | M5 |
| MA0002 | 147720853 | 53 | 54 | 55 | A | |
| MA0003 | 151346184 | 56 | 57 | 58 | C | |
| MA0007 | 152045106 | 59 | 60 | 61 | T | |
| MA0008 | 152045141 | 62 | 63 | 64 | T | |
| MA0009 | 152045402 | 65 | 66 | 67 | T | |
| MA0010 | 152045516 | 68 | 69 | 70 | C | |
| MA0011 | 152045912 | 71 | 72 | 73 | T | |
| MA0012 | 152046502 | 74 | 75 | 76 | A | |
| MA0022 | 152046529 | 244 | 245 | 246 | A | M8 |
| MA0013 | 152133057 | 77 | 78 | 79 | G | M8 |
| MA0014 | 152133380 | 80 | 81 | 82 | T | |
| MA0015 | 152144310 | 83 | 84 | 85 | A | |
| MA0016 | 152250992 | 86 | 87 | 88 | A | |
| MA0017 | 152301656 | 89 | 90 | 91 | A | |
| MA0018 | 152304127 | 92 | 93 | 94 | A | |
| MA0019 | 152630794 | 95 | 96 | 97 | C | |
| MA0020 | 152753635 | 98 | 99 | 100 | A | |
| PZE-108095998 | 152433358 | 101 | 102 | 103 | T | |
| PZE-108096011 | 152435855 | 104 | 105 | 106 | A | |
| PZE-108096610 | 152703579 | 107 | 108 | 109 | C | |
| PZE-108096791 | 152887338 | 110 | 111 | 112 | G | |

Furthermore, the present invention concerns a seed or grain, a tissue, an organ, a portion and a cell of the maize plants in accordance with the invention described above. In this regard, the seed or the grain is a seed or a grain into the genome of which the chromosome fragment of the embodiment of the invention described above has been integrated.

In a further aspect, the present invention concerns a method for identifying a H. turcicum-resistant maize plant into the genome of which a chromosome fragment from the donor Pepitilla has been integrated, comprising the descendants of at least two alleles in the genome of the plant, wherein at least one allele is localized in a genomic segment which is flanked by a marker in the first marker region M1, the second marker region M2, the third marker region M3, the fourth marker region M4 or the seventh marker region M7, and by the polynucleotide described above which confers resistance to H. turcicum in the maize plant, and wherein at least one allele is localized in a genomic segment which is flanked by a marker in the sixth marker region M6, the fifth marker region M5 or the eighth marker region M8. The marker regions and exemplary markers in these marker regions are described above. Preferably, the identified maize plant is a maize plant in accordance with the invention. Furthermore, the invention also concerns a maize plant which has been identified using the identification method which has been mentioned.

In a further aspect, the present invention concerns a method for increasing the yield of a H. turcicum-resistant maize plant, into the genome of which a chromosome fragment from the donor Pepitilla has been integrated, wherein the method comprises a step which removes the second interval of the donor, the fourth interval of the donor or the fifth interval of the donor and wherein the chromosome fragment comprises the first interval of the donor described above which comprises donor alleles in accordance with the haplotype of Table 2 and a polynucleotide which confers resistance to Helminthosporium turcicum in the maize plant. As an example, removal may be carried out by genetic recombination during a crossing process between two maize plants, wherein a parent maize plant carries the HTN1-resistance locus from Pepitilla. In addition to the use of conventional breeding techniques to produce a genetic recombination which has the result of replacing at least one of the donor intervals with linkage drag identified above with genomic sequences of the recurrent parent which are preferably free from unwanted genes, modern biotechnology offers the person skilled in the art many tools which can enable precise genetic engineering to be carried out. Examples of known tools are meganucleases (Silva et al., 2011), homing endonucleases (Chevalier 2002), zinc finger nucleases, TALE nucleases (WO 2010/079430; WO 2011/072246) or CRISPR (Gaj et al., 2013). These are artificial nuclease fusion proteins which are capable of cleaving double stranded nucleic acid molecules such as plant DNA and thus of producing double strand breaks at desired positions in the genome. By exploiting the cells own mechanisms for repairing induced double strand breaks, a homologous recombination or a "non-homologous end joining" can be carried out, which could lead to the removal of the intervals of the donor carrying linkage drag. Suitable target sequences in the genome for the recognition domain nucleases may be taken, for example, from the sequence information for the SNP markers (Table 4) or in their intervals. However, a person skilled in the art is also able to identify other sequences, preferably within or between the six marker regions described above, which are suitable as target sequences for the recognition domains of the nucleases.

In this regard we shall now describe two genetic engineering approaches in more detail, with the aid of which the elimination of linkage drag-carrying nucleotide sequences from a plant genome is supported or directly obtained. The following methods as well as the conventional breeding method may be employed for the production of the maize plants in accordance with the invention.

As already stated, current molecular tools are capable of inducing double strand breaks at defined locations in the genome of a plant DNA. In this regard the use of TALE nucleases (TALENs) or zinc finger nucleases (ZFNs) has proved to be particularly advantageous. The TALE or ZF recognition domain enables it to bind specifically to any location in the genome. Knowing the sequence in the target region, the TALE or ZF recognition domains can be tailored so that they exclusively bind to desired locations in the genome. If, for example, the recognition sequence is fused with a non-specific endonuclease such as FokI, a double strand break (DSB) can be induced at defined locations in the genome, enabling targeted genome engineering (Tzfira et al., 2012; Li et al., 2011; Puchta and Hohn 2010). The person skilled in the art will be familiar with handling FokI endonucleases and the provision of suitable TALENs and ZFNs from the prior art.

An induced double strand break may, for example, stimulate a homologous recombination between an endogenic target gene locus (for example one of the above marker regions) and an exogenically introduced homologous DNA fragment which, for example, is not a carrier of linkage drag (for example on a suitable donor vector). This so-called gene replacement or genome editing can be carried out in vitro and does not necessitate any crossing steps between two plants. To this end, the plants to be modified must on the one hand be transiently transformed with nucleic acids coding for the designated TALENs or ZFNs, and on the other hand with the exogenic DNA fragment. The DNA fragment in this regard may originate from a plant of the same species and, for example, corresponds to the chromosomal segment which is to be replaced, but without linkage drag. After completing the induced homologous recombination, cells with a modified genome can be regenerated into plants and then selected as to whether the linkage drag has been successfully removed and the previously transformed DNA elements are once again lost during the regenerative cell division. The markers described above may also be used for this purpose. Methods for the transformation and regeneration are known in the prior art and are also discussed further below.

Furthermore, the present TALENs and ZFNs may also be transgenically introduced during the process of meiosis, where double strand breaks are induced at predetermined locations in the genome and thus the probability for a recombination at these locations in the crossing over step is increased. In this manner, the elimination of linkage drag can be significantly encouraged. A person skilled in the art is aware that after completion of meiosis, linkage drag-free and TALENs or ZFNs-free plants are produced from the haploid cells. In a further aspect, the present invention concerns a method for the production of a maize plant in accordance with the invention, which comprises the following steps: (A) preparing a first maize plant into the genome of which a chromosome fragment from the donor Pepitilla has been integrated, wherein the chromosome fragment comprises a first interval of the donor which exhibits donor alleles in accordance with the haplotype of Table 2 and comprises a polynucleotide which confers resistance against *Helminthosporium turcicum* in the maize plant, and wherein the chromosome fragment contains a second interval of the donor and/or the fourth interval of the donor and/or the fifth interval of the donor, (B) providing a second maize plant, (C) crossing the maize plant from (A) with the maize plant from (B), and (D) selecting a maize plant in accordance with the invention, preferably using at least one of the markers described above. Alternatively, the present invention concerns a method for the production of a maize plant in accordance with the invention which comprises the following steps: (A) transiently transforming a maize plant cell with a first nucleotide sequence which codes for a first protein with endonuclease activity (for example a TALE or ZF endonuclease fusion protein) which is capable of inducing a double strand break of the DNA between the marker regions M2 and M4 in the maize plant cell, and with a second nucleotide sequence which codes for a second protein with endonuclease activity (for example a TALE or ZF endonuclease fusion protein) which is capable of inducing a double strand break of the DNA in the genome of the maize plant cell between marker regions M5 and M6, (B) transiently introducing a donor vector into the first maize plant cell which carries a chromosome fragment from the donor Pepitilla, wherein the chromosome fragment comprises a first interval of the donor which exhibits donor alleles in accordance with the haplotype of Table 2 and comprises a polynucleotide which confers resistance against *Helminthosporium turcicum* in the maize plant, and wherein the chromosome fragment furthermore comprises the chromosomal segments of the donor Pepitilla between the sites of the double strand break from (A) so that a homologous recombination takes place between the genome of the first maize plant cell and the chromosome fragment of the donor vector, (C) regeneration of a maize plant from the maize plant cell, (D) identification of a maize plant in accordance with the invention, preferably using at least one of the markers described above. Particularly preferably, transiently introduced first and second nucleic acid sequences and donor vectors are then lost. The person skilled in the art will know how to carry this out and detect it.

In a further aspect, the invention encompasses the markers described above as oligonucleotides, in particular primer oligonucleotides. Preferably, the oligonucleotides are isolated oligonucleotides. An oligonucleotide comprises a nucleic acid molecule with a nucleotide sequence selected from one of SEQ ID NOs: 41-49, 53-100 and 229-250. Furthermore, the present invention concerns the use of an oligonucleotide which comprises a nucleic acid molecule with a nucleotide sequence selected from one of the SEQ ID NOs: 17-250, for the identification of a *H. turcicum*-resistant maize plant. Preferably, the resistance derives from the donor Pepitilla and is HTN1.

Furthermore, the problem of the present invention is alternatively solved by means of a transgenic plant, in particular a transgenic maize plant, which comprises a transgenic plant cell as described below. Furthermore, the invention also concerns a portion of this plant in accordance with the invention, wherein a portion may be a cell, a tissue, an organ or a fusion of several cells, tissues or organs. An example of a fusion of several organs is a flower or a seed. In a particular embodiment, the invention concerns a seed from the transgenic plant, wherein the seed comprises the polynucleotide in accordance with the invention as the transgene, as described below. Preferably, a transgenic plant in accordance with the present invention, in particular a plant of the species *Zea mays*, exhibits a higher resistance to *H. turcicum* than a corresponding non-transformed plant (isogenic plant without the transgene). A transgenic HT-resistant plant in accordance with the invention exhibits an increased resistance to *H. turcicum* of at least one classification score, preferably at least 2 classification scores or at least 3 classification scores and particularly preferably at least 4 classification scores (see classification score scheme in Table 3).

Furthermore, the invention provides a method for the production of a transgenic plant which comprises a step for introducing the polynucleotide of the invention or the vector of the present invention described below into a plant cell, and optionally a step for selection of a transgenic plant cell. Furthermore, a method of this type for the production of a transgenic plant is characterized by a subsequent step which includes the regeneration of the transgenic plant from the transgenic plant cell produced in the first step. Methods for regeneration are known to the person skilled in the art from the prior art.

In an additional aspect, the present invention discloses the polynucleotide which contains one or more resistance-conferring genes of the HTN1 locus from Pepitilla (table 1) or selected from RLK1 and EXT1 (see Table 1) or gene alleles thereof. Genes or gene alleles may bring about a resistance phenotype with the features typical of HTN1 under infestation conditions with *H. turcicum*. Structurally, the polynucleotide is characterized in that it comprises a nucleic acid molecule that (a) comprises a nucleotide sequence in accordance with SEQ ID NO: 1, 3, 5, 7, 9, 11, 13 or 15, (b) comprises a nucleotide sequence with an identity of at least 80%, 85%, 90%, 91%, 92%, 93%, 94%, 95%, 96%, 97%, 98% or 99% with one of the nucleotide sequences in accordance with SEQ ID NO: 1, 3, 5, 7, 9, 11, 13 and 15, preferably over the entire length of the sequence, (c) which hybridizes with the complementary strand of a nucleic acid molecule in accordance with (a) or (b) under stringent conditions, (d) which codes for a polypeptide with an amino acid sequence in accordance with SEQ ID NO: 2, 4, 6, 8, 10, 12, 14 or 16, or (e) which codes for a polypeptide with an amino acid sequence which has at least 80%, 85%, 90%, 91%, 92%, 93%, 94%, 95%, 96%, 97%, 98% or 99% A identity with one of the amino acid sequences in accordance with (d). In a preferred embodiment, the polynucleotide is characterized in that it comprises a nucleic acid molecule which (aa) comprises a nucleotide sequence in accordance with SEQ ID NO: 1 or 5, (bb) comprises a nucleotide sequence with an identity of at least 80%, 85%, 90%, 91%, 92%, 93%, 94%, 95%, 96%, 97%, 98% or 99% A with one of the nucleotide sequences in accordance with SEQ ID NO: 1 or 5, preferably over the entire length of the sequence, (cc) which hybridizes with the complementary strand of a nucleic acid molecule in accordance with (aa) or (bb) under stringent conditions, (dd) which codes for a polypeptide with an amino acid sequence in accordance with SEQ ID NO: 2 or 6, or (ee) which codes for a polypeptide with an amino acid sequence which has at least 80%, 85%, 90%, 91%, 92%, 93%, 94%, 95%, 98%, 97%, 98% or 99% identity with one of the amino acid sequences in accordance with (dd). Preferably, the polynucleotide can be isolated and/or purified from its natural genetic environment or is present essentially in the pure or homogeneous form. Preferably, the polynucleotide is DNA, and particularly preferably cDNA, i.e. the polynucleotide comprises the cDNA from one or more resistance-conferring genes (Table 1). However, it may also be present as RNA. The person skilled in the art will know how to deduce the genomic DNA sequence from the sequence information disclosed herein. A polynucleotide in accordance with the invention codes for at least one polypeptide which is capable of conferring a resistance against the pathogen *Helminthosporium turcicum* in a plant in which the polypeptide is expressed. Preferably, the polypeptide which is coded by the polynucleotide of the invention or portions thereof, preferably confers resistance to the pathogen *Helminthosporium turcicum*, in particular in a plant of the genus *Zea* or in a plant of the species *Zea mays*.

Furthermore, the present invention also concerns a polypeptide which is capable of conferring resistance to *H. turcicum* in a plant in which the polypeptide is expressed and which is encoded by the polynucleotide of the invention or a portion thereof. Preferably, the polypeptide comprises an amino acid sequence in accordance with SEQ ID NO: 2, 4, 6, 8, 10, 12, 14 or 16 or, particularly preferably, an amino acid sequence in accordance with SEQ ID NO: 2 or 6. The polypeptide may be an isolated polypeptide.

In a further aspect, the present invention concerns a vector which comprises the polynucleotide in accordance with the invention. The vector may be a plasmid, a cosmid, a phage or an expression vector, a transformation vector, shuttle vector or cloning vector, it may be double or single stranded, linear or circular, or it may be a prokaryotic or eukaryotic host, either by integration into its genome or transforming extrachromosomally. Preferably, the polynucleotide of the invention is operatively linked in an expression vector with one or more regulatory sequences which allow transcription and optionally expression in a prokaryotic or eukaryotic host cell. As an example, the polynucleotide may be under the control of suitable promoters or a terminator. Suitable promoters may be promoters which are constitutively induced (example: 35S promoter from the "cauliflower mosaic virus" (Odell et al. 1985); particularly suitable promoters are those promoters which are pathogen-inducible (example: PR1 promoter from parsley (Rushton et al., 1996)). Particularly suitable pathogen-inducible promoters are synthetic or chimeric promoters which do not occur in nature, are composed of several elements and contain a minimum promoter as well as, upstream of the minimum promoter, at least one cis-regulatory element which act as the binding site for special transcription factors. Chimeric promoters are custom-designed and are induced by various factors or re-primed. Examples of such promoters can be found in WO 2000/29592 and WO 2007/147395. An example of a suitable terminator is the nos-terminator (Depicker et al., 1982).

In addition to the vectors described above, the present invention also provides a method which comprises introducing a vector as described into a host cell. The vector may, for example, be introduced by conjugation, mobilization, biolistic transformation, *agrobacterium*-conferred transformation, transfection, transduction, vacuum infiltration or electroporation. Methods of this type as well as methods for the preparation of the vectors described are familiar to the person skilled in the art (Sambrook et al. 2001).

In a further aspect, the present invention concerns a host cell which comprises the polynucleotide of the invention or a vector of the present invention. In the context of the invention, a host cell may be a prokaryotic cell (for example bacterial) or eukaryotic cell (for example a plant cell or a yeast cell). Preferably, the enzyme is an *agrobacterium* such as *Agrobacterium tumefaciens* or *Agrobacterium rhizogenes*, or a plant cell which comprises the polynucleotide of the invention or the vector of the present invention. The person skilled in the art will be familiar with the many methods such as conjugation or electroporation for introducing the polynucleotide of the invention or the vector of the present invention into an *agrobacterium*, and also methods such as various transformation methods (biolistic transformation, *agrobacterium*-conferred transformation) with which the polynucleotide of the invention or the vector of the present invention can be introduced into a plant cell (Sambrook et al. 2001).

In a further aspect, the present invention concerns a transgenic plant cell which comprises the polynucleotide in accordance with the invention as a transgene or the vector of the present invention. A transgenic plant cell of this type is, for example, a plant cell which is transformed with the polynucleotide in accordance with the invention or with the vector of the present invention, preferably in a stable manner. In a preferred embodiment of the transgenic plant cell, the polynucleotide is operatively linked with one or more regulatory sequences which allow transcription and optionally expression in the plant cell. The total construct of the polynucleotide in accordance with the invention and the regulatory sequence(s) may then constitute the transgene. Examples of regulatory sequences of this type are a promoter or a terminator. The person skilled in the art will be familiar with many functional promoters and terminators which can be used in plants. Preferably, a transgenic plant cell in accordance with the present invention, in particular a cell of a plant of the species *Zea mays*, exhibits a higher resistance to *H. turcicum* than a corresponding non-transformed plant cell (the (isogenic) plant cell without the transgene). Transgenic HT-resistant plant cells of the invention exhibit an increased resistance to *H. turcicum* by at least one classification score, preferably at least 2 classification scores or at least 3 classification scores and particularly preferably at least 4 classification scores (see the classification scheme in Table 3). Furthermore, the present invention also concerns a method for the production of a transgenic plant cell of the present invention, which comprises a step for introducing the polynucleotide in accordance with the invention or the vector of the present invention into a plant cell. As an example, the introduction may be carried out by transformation, preferably by stable transformation. Suitable techniques for introduction such as biolistic transformation, *agrobacterium*-conferred transformation or electroporation are known to the person skilled in the (Sambrook et al. 2001).

In a further aspect, the present invention also concerns a method for conferring or increasing a resistance to *H. turcicum* in a plant, preferably a plant of the species *Zea mays*, which comprises a step for transformation of a plant cell with a polynucleotide in accordance with the invention or with the vector of the present invention. Preferably, this method results in enhanced resistance to *H. turcicum* by at least 1 classification score, preferably at least 2 classification scores or at least 3 classification scores and particularly preferably at least 4 classification scores (see the classification scheme in Table 3).

In an additional aspect, the present invention also encompasses a method for modification of the resistance phenotype of a plant, in particular a maize plant, to the pathogen *Helminthosporium turcicum*, which comprises a step for mutation of the resistance-conferring gene of the HTN1 locus from Pepitilla or a gene allele comprised therein. Preferably, the resistance-conferring gene of the HTN1 locus from Pepitilla codes for a polypeptide in accordance with SEQ ID NO: 2 or a homologue of a polypeptide in accordance with SEQ ID NO: 2 which produces a resistance phenotype with the features typical of HTN1 under infestation conditions with *H. turcicum*. The resistance-conferring gene of the HTN1 locus from Pepitilla or a gene allele thereof can be transgenic or endogenic in the genome of the plant. Modification of the resistance phenotype can mean a change in the pathogen race specificity and/or a change in the resistance level, measured as the classification score based on the phenotypical characteristics such as the affected leaf surface (see Table 3) or measured as an AUDPC value (see Example 1.C). Preferably, the resistance level after modification of the resistance phenotype is between the resistance level of a plant which expresses the non-mutated resistance-conferring gene of the HTN1 locus from Pepitilla and the resistance level of an isogenic plant which does not express the resistance-conferring gene of the HTN1 locus from Pepitilla; however, it may also be above the resistance level of a plant which expresses the non-mutated resistance-conferring gene of the HTN1 locus from Pepitilla. Particularly preferably, the resistance level is between the resistance level of a plant which expresses the polypeptide in accordance with SEQ ID NO: 2 and the resistance level of an isogenic plant which does not express the polypeptide in accordance with SEQ ID NO: 2; it may also, however, be above the resistance level of a plant which expresses the polypeptide in accordance with SEQ ID NO: 2. The expression "mutate" as used herein may be a change carried out by man in the genetic sequence (mutation). Examples in this regard are that plants, plant cells or plant portions receiving a high dose of chemical, radiological or other mutating agents and then selecting for mutants. Alternatively, the mutation may also be carried out with, for example, the help of TILLING nucleases, TALE nucleases, zinc finger nucleases or a CRISPR/Cas system, or by fusion, insertion, deletion or exchange in the DNA sequence or the amino acid sequence. The person skilled in the art may receive sufficient technical instruction from the prior art regarding carrying out the mutation steps. Preferably, mutation of the resistance-conferring gene of the HTN1 locus from Pepitilla results in at least one amino acid exchange, at least two amino acid exchanges, at least three amino acid exchanges, or at least five or more amino acid exchanges. In the case of a plurality of amino acid exchanges, they may be carried out on different gene alleles for the resistance-conferring gene of the HTN1 locus from Pepitilla, i.e. the mutation may be heterozygous or it may also be homozygous.

In a preferred embodiment of the method for the modification of the resistance phenotype of a plant, mutation of the resistance-conferring gene of the HTN1 locus from Pepitilla results in a point mutation in the nucleotide sequence in accordance with SEQ ID NO: 1 at position 1365 with base exchange of a G for an A or at position 1490 with base exchange of a G for an A. Furthermore, this embodiment also concerns a mutation which leads to an amino acid exchange in the amino acid sequence in accordance with SEQ ID NO: 2 at position 455 from M (methionine) to I (isoleucine) or at position 497 from G (glycine) to E (glutamic acid). In a further preferred embodiment of the method, mutation of the resistance-conferring gene of the HTN1 locus from Pepitilla results in a point mutation, which results in an amino acid exchange in the nucleotide sequence in accordance with SEQ ID NO: 1 between position 1365 and position 1490, or the embodiment concerns the mutation which leads to an amino acid exchange in the amino acid sequence in accordance with SEQ ID NO: 2 between position 455 and position 497.

In a further aspect, the invention concerns a method for producing a plant, in particular a maize plant, having a modified resistance phenotype as regards the pathogen *Hel-*

*minthosporium turcicum*, which comprises a step for mutation of the resistance-conferring gene of the HTN1 locus from Pepitilla or a gene allele thereof in at least one cell of the plant or in at least one cell from which the plant is regenerated. Furthermore, the method can thus comprise a step for regeneration of at least one plant from at least one mutated cell and selection of the regenerated plants on the basis of the modified resistance phenotype as regards the pathogen *Helminthosporium turcicum*. Preferably, the resistance-conferring gene of the HTN1 locus from Pepitilla codes for a polypeptide in accordance with SEQ ID NO: 2 or a homologue of a polypeptide in accordance with SEQ ID NO: 2, which produces a resistance phenotype with the features typical of HTN1 under infestation conditions with *H. turcicum*. The resistance-conferring gene of the HTN1 locus from Pepitilla or a gene allele thereof may be present in the plant transgenically or endogenically. Modification of the resistance phenotype can mean a change in the pathogen race specificity and/or a change in the resistance level, measured as the classification score based on the phenotypical characteristics such as the affected leaf surface (see Table 3) or measured as an AUDPC value (see Example 1.C). Preferably, the resistance level of the modified resistance phenotype lies between the resistance level of a plant which expresses the non-mutated resistance conferred gene of the HTN1 locus from Pepitilla and the resistance level of an isogenic plant which does not express the resistance conferred gene of the HTN1 locus from Pepitilla; however, it may be above the resistance level of a plant which expresses the non-mutated resistance conferred gene of the HTN1 locus from Pepitilla. Particularly preferably, the resistance level is between the resistance level of a plant which expresses the polypeptide in accordance with SEQ ID NO: 2 and the resistance level of an isogenic plant which does not express the polypeptide in accordance with SEQ ID NO: 2; however, it can also be above the resistance level of a plant which expresses the polypeptide in accordance with SEQ ID NO: 2. The expression "mutation" herein may be understood to be a change in the genetic sequence (mutation) carried out by man. Examples in this regard are plants, plant cells or plant parts receiving a high dose of chemical, radiological or other mutagens and then being selected for mutants. Alternatively, mutation may also be carried out, for example, with the aid of TILLING nucleases, TALE nucleases, zinc finger nucleases or a CRISPR/Cas system or by fusion, insertion, deletion or exchanges in the DNA sequence or the amino acid sequence. The person skilled in the art may receive sufficient technical instruction from the prior art regarding carrying out the mutation steps. Preferably, mutation of the resistance-conferring gene of the HTN1 locus from Pepitilla results in at least one amino acid exchange, at least two amino acid exchanges, at least three amino acid exchanges, at least five or in more amino acid exchanges. In the case of a plurality of amino acid exchanges, these may also be present on different gene alleles of the resistance-conferring gene of the HTN1 locus from Pepitilla, i.e. the mutation may be heterozygous or even homozygous.

In a preferred embodiment of a method for the production of a plant having a modified resistance phenotype as regards the pathogen *Helminthosporium turcicum*, mutation of the resistance-conferring gene of the HTN1 locus from Pepitilla results in a point mutation in the nucleotide sequence in accordance with SEQ ID NO: 1 at position 1365 with base exchange of a G for an A or at position 1490 with base exchange of a G for an A. Furthermore, this embodiment also concerns a mutation which leads to an amino acid exchange in the amino acid sequence in accordance with SEQ ID NO: 2 at position 455 from M (methionine) to I (isoleucine) or at position 497 from G (glycine) to E (glutamic acid). In a further preferred embodiment of the method, mutation of the resistance-conferring gene of the HTN1 locus from Pepitilla results in a point mutation, which results in an amino acid exchange in the nucleotide sequence in accordance with SEQ ID NO: 1 between position 1365 and position 1490, or the embodiment concerns the mutation which leads to an amino acid exchange in the amino acid sequence in accordance with SEQ ID NO: 2 between position 455 and position 497.

The invention also concerns plants or parts thereof which may be produced by a method for the production of a plant with a modified resistance phenotype as regards the pathogen *Helminthosporium turcicum*.

Further, the invention encompasses a plant or a part thereof which comprises a mutation in the resistance-conferring gene of the HTN1 locus from Pepitilla or a gene allele thereof. Preferably, the mutation results in a modified resistance phenotype as described above. Preferably, the resistance-conferring gene of the HTN1 locus from Pepitilla codes for a polypeptide in accordance with SEQ ID NO: 2 or a homologue of a polypeptide in accordance with SEQ ID NO: 2, which produces a resistance phenotype with the features typical of HTN1 under infestation conditions with *H. turcicum*. The resistance-conferring gene of the HTN1 locus from Pepitilla or a gene allele thereof may be present in the plant transgenically or endogenically. In a preferred embodiment, of the plant or the part thereof, the mutation is a point mutation in the nucleotide sequence in accordance with SEQ ID NO: 1 at position 1365 with base exchange of a G for an A or at position 1490 with base exchange of a G for an A. Furthermore, this embodiment also concerns a mutation which leads to an amino acid exchange in the amino acid sequence in accordance with SEQ ID NO: 2 at position 455 from M (methionine) to I (isoleucine) or at position 497 from G (glycine) to E (glutamic acid). In a further preferred embodiment of the plant or the part thereof, the mutation of the resistance-conferring gene of the HTN1 locus from Pepitilla is a point mutation which results in an amino acid exchange in the nucleotide sequence in accordance with SEQ ID NO: 1 between the position 1365 and the position 1490, or the embodiment concerns a mutation which leads to an amino acid exchange in the amino acid sequence in accordance with SEQ ID NO: 2 between position 455 and position 497.

Some of the terms used in this application will now be explained in more detail:

The term "allele" refers to one or two or more nucleotide sequences at a specific locus in the genome. A first allele is on a chromosome, a second on a second chromosome at the same position. If the two alleles are different, they are heterozygous, and if they are the same, they are homozygous. Various alleles of a gene (gene alleles) differ in at least one SNP. Depending on the context of the description, an allele also means a single SNP which, for example, allows for a distinction between the donor of HTN1 (Pepitilla) and recurrent parent.

The expression "chromosome fragment" means a specific chromosomal DNA segment of a specific chromosome which comprises at least one gene. An integrated chromosome fragment derives from a donor source. In the context of the invention, the sequential succession of the genes within an integrated chromosome fragment corresponds to that sequence as it is present in the original chromosome fragment of the donor source. In this manner, the integrated chromosome fragment may be present over the whole length unchanged compared with the corresponding chromosome fragment in the donor source. A chromosome fragment or a part thereof may constitute a specific "haplotype", wherein the chromosome fragment may comprise specific SNPs through which the haplotype can also be unequivocally specified and identified.

The terms "distal" and "proximal" describe the position of a chromosomal interval or a genetic segment in relation to a specific reference point (for example a specific polynucleotide, another chromosomal interval or a gene) on a whole chromosome; "distal" means that the interval or the segment is localized on the side of the reference point distant from the chromosome centromere, and "proximal" means that the interval or the segment is localized on the side of the reference point close to the chromosome centromere.

"close coupled" or "closely linked" means two loci, two intervals, two genetic segments or two markers (marker loci) which are less than 15 cM, less than 12 cM, less than 10 cM, less than 8 cM, less than 7 cM, less than 6 cM, less than 5 cM, less than 4 cM, less than 3 cM, less than 2 cM, less than 1 cM, less than 0.5 cM, less than 0.2 cM, less than 0.1 cM distant from each other, established using the IBM2 neighbors 4 genetic map which is publicly available on the Maize GDB website.

The term "yield" as used in the context of the present invention refers to the productivity per unit area of a specific plant product with commercial value. As an example, the yield of maize is usually measured in metric tonnes of seed or grain per hectare (ha) and season or in metric tonnes of dry biomass per hectare (ha) and season. Unless otherwise specifically stated or specified, the yield may mean the absolute fresh or dry matter, the relative fresh or dry matter, the silage yield (also known as the silo maize yield or total dry matter yield) or the grain yield. The yield is influenced by genetic and environmental factors and in principle is a combination of many agronomic properties which are built up of features based on genetic elements of a plant and contribute to the final yield during the season. Examples of these individual agronomic properties are seed emergence, vegetative vitality, stress tolerance, disease resistance or tolerance, herbicide resistance, branching tendency, flowering time, seed clusters, seed density, stability and storeability, threshing capability (uniform ripening), etc.

The expression "genetic segment with" a more precisely specified interval should be understood to mean a genetic segment which encloses or comprises the more precisely specified interval, i.e. is not limited to the more precisely specified interval. As an example, a "genetic segment with the fifth interval between a marker in the eighth marker region M8 which is flanked by the markers MA0022 and MA0013, and a marker in the sixth marker region M6 which is flanked by the markers PZE-108107671 and SYN4196" means that the genetic segment comprises the fifth interval and the genetic segment are localized between a marker in the eighth marker region M8 which is flanked by the markers MA0022 and MA0013 and a marker in the sixth marker region M6 which is flanked by the markers PZE-108107671 and SYN4196.

The term "hybridize" or "hybridization" should be understood to mean a procedure in which a single stranded nucleic acid molecule agglomerates with a nucleic acid strand which is as complementary as possible, i.e. base-pairs with it. Examples of standard methods for hybridization have been described in 2001 by Sambrook et al. Preferably, this should be understood to mean that at least 60%, more preferably at least 65%, 70%, 75%, 80% or 85%, particularly preferably 90%, 91%, 92%, 93%, 94%, 95%, 96%, 97%, 98% or 99% of the bases of the nucleic acid molecule undergo base pairing with the nucleic acid strand which is as complementary as possible. The possibility of such agglomeration depends on the stringency of the hybridization conditions. The term "stringency" refers to the hybridization conditions. High stringency is when base pairing is more difficult, low stringency is when base pairing is easier. The stringency of the hybridization conditions depends, for example, on the salt concentration or ionic strength and the temperature. In general, the stringency can be increased by raising the temperature and/or by reducing the salt content. The term "stringent hybridization conditions" should be understood to mean those conditions under which a hybridization takes place primarily only between homologous nucleic acid molecules. The term "hybridization conditions" in this respect refers not only to the actual conditions prevailing during actual agglomeration of the nucleic acids, but also to the conditions prevailing during the subsequent washing steps. Examples of stringent hybridization conditions are conditions under which primarily only those nucleic acid molecules that have at least 70%, preferably at least 75%, at least 80%, at least 85%, at least 90% or at least 95% sequence identity undergo hybridization. Stringent hybridization conditions are, for example: 4×SSC at 65° C. and subsequent multiple washes in 0.1×SSC at 65° C. for approximately 1 hour. The term "stringent hybridization conditions" as used herein may also mean: hybridization at 68° C. in 0.25 M sodium phosphate, pH 7.2, 7% SDS, 1 mM EDTA and 1% BSA for 16 hours and subsequently washing twice with 2×SSC and 0.1% SDS at 68° C. Preferably, hybridization takes place under stringent conditions.

The term "interval" or "chromosomal interval" means a continuous linear segment on a genomic DNA which is present in an individual chromosome in a plant or on a chromosome fragment and which is usually defined through two markers which represent the end points of the interval on the distal and proximal side. In this regard, the markers which define the ends of the interval may themselves also be a part of the interval. Furthermore, two different intervals might overlap. In the description, an interval is specified by the statement "between marker A and marker B". An end marker of an interval may also be localized in a defined marker region to one side of the interval. A marker region is then defined by providing two flanking markers and constitutes a chromosomal segment on which more markers might be located, in addition to the flanking markers. Flanking markers determine the end points of a marker region and are themselves still a part of the marker region. If both end markers of an interval are markers in different marker regions on both sides of an interval, the description specifies an interval by stating "between a marker in a marker region X which is flanked by the markers C and D and a marker in a marker region Y which is flanked by markers E and F". A marker region may extend over up to 500 000 base pairs (bp), and can preferably be between 100000 and 400000 bp in size, or can particularly preferably be between 140000 and 315000 bp in size.

The term "introgression" as used in connection with the present invention means the transfer of at least one desired gene allele on a genetic locus of a genetic background into another. As an example, an introgression of a desired gene allele at a specific locus may be transferred to a descendant by sexual crossing between two parents of the same species. Alternatively, for example, the transfer of a gene allele may also occur by recombination between two donor genomes in a fused protoplast, wherein at least one donor protoplast carries the desired gene allele in its genome. In each case the descendants, which then comprise the desired gene allele, can then be backcrossed again with a line which comprises a preferred genetic background and can be selected for the desired gene allele. The result is fixing of the desired gene allele in a selected genetic background.

The term “isolated nucleic acid molecule” or “isolate polynucleotide” should be understood to mean a nucleic acid molecule or polynucleotide removed from its natural or original environment. The term also encompasses a synthetically produced nucleic acid molecule. An “isolated polypeptide” should be understood to mean a polypeptide which has been removed from its natural or original environment. The term also encompasses a synthetically produced polypeptide.

The term “pathogen infection” should be understood to mean the earliest time at which a pathogen interacts with a plant host tissue. Examples in fungi such as ascomycetes or oomycetes are the growth of hyphae or the formation of specific infection structures such as penetration hyphae and the appressorium. In detail, an infection with *Helminthosporium turcicum* may be investigated using various stain techniques (for example trypan blue) (Chung et al., *BMC Plant Biology* 10 (2010), 103; Walsh et al. (2008), Poster presentation P192, 50th Maize Genetics Conference in Washington D.C.).

“Donor Pepitilla”, “accession Pepitilla” or “Pepitilla” means, in addition to the landrace Pepitilla itself, other maize genotypes into the genome of which, in particular on chromosome 8 bin 5 or 6, an introgression of the HTN1 resistance locus, preferably from Pepitilla, has been inserted. Examples of these are W22Htn (e.g. Bar-Zur et al. 1998), H6314Htn (e.g. Bar-Zur et al. 1998), B73HtN (e.g. Shimoni et al., Journal of Phytopathology 131:4 (1991), 315-321), B68HtN and A632HtN (e.g. Carson, Plant Disease 79 (1995), 717-720) and A619HtN (e.g. Stanković et al, Genetika 39:2 (2007), 227-240). Furthermore, Pepitilla includes any source of resistance which confers the resistance phenotype with the features typical of HTN1 after introgression into a vulnerable maize line/maize plant. Examples of these HTN1-specific features are delayed onset of sporulation, reduced development of lesions, development of smaller lesions, reduced sporulation zones and/or no or only isolated chlorotic-necrotic lesions.

A “Locus” is a position on a chromosome where one or more genes are found which cause an agronomic feature or influence one. In particular, “locus” as used here means the HTN1-resistance locus which confers resistance against the pathogen *Helminthosporium turcicum* or at least against a race of *Helminthosporium turcicum*.

A “maize plant” should be understood to mean a plant from the species *Zea mays* as well as its subspecies such as, for example, *Zea mays* ssp. *mays, Zea mays* ssp. *mexicana* or *Zea mays* ssp. *parviglumis*.

A “marker” is a nucleotide sequence which is used as a reference or orientation point. A marker for recognizing a recombination event should be suitable for monitoring differences or polymorphisms in a plant population. For markers, these differences are on a DNA level and, for example, are polynucleotide sequence differences such as, for example, SSRs (simple sequence repeats), RFLPs (restriction fragment length polymorphisms), FLPs (fragment length polymorphisms) or SNPs (single nucleotide polymorphisms). The markers may be derived from genomic or expressed nucleic acids such as spliced RNA, cDNA or ESTs and may be based on nucleic acids which are used as probes or primer pairs and as such are suitable for amplifying a sequence fragment using PCR-based methods. Markers which concern genetic polymorphisms between parts of a population can be detected using established methods from the prior art (An Introduction to Genetic Analysis. 7th Edition, Griffiths, Miller, Suzuki et al., 2000). These include, for example: DNA sequencing, PCR-based, sequence-specific amplification, assaying of RFLPs, assaying of polynucleotide polymorphisms using allele-specific hybridization (ASH), detection of SSRs, SNPs or AFLPs. Methods for detecting ESTs (expressed sequence tags) and RAPD (randomly amplified polymorphic DNA) are also known. Depending on the context, the term “marker” in the description may also mean a specific chromosome position in the genome of a species where a specific marker (for example SNP) can be found. A marker position of this type can be used in order to monitor the presence of a coupled locus, for example a coupled locus which contributes to the expression of a specific phenotypical feature (e.g. HTN1 or linkage drag). As an example, the marker locus may also be used to observe the segregation of alleles at a locus (QTL or individual gene) which are genetically or physically closely coupled with the marker position.

“Operatively linked” means linked in a common nucleic acid molecule in a manner such that the linked elements are positioned and orientated with respect to each other such that transcription of the nucleic acid molecule can take place. A DNA which is operatively linked with a promoter is under the transcriptional control of this promoter.

Examples of plant “organs” are leaves, plant stems, stems, roots, vegetative buds, meristems, embryos, anthers, ovulae or fruit. Plant “parts” means a fusion of several organs, for example a flower or a seed or a part of an organ, for example a cross segment from the stem. Examples of plant “tissues” are callus tissue, soft tissue, meristem tissue, leaf tissue, bud tissue, root tissue, plant tumour tissue or reproductive tissue. The term “cells” should be understood to mean isolated plant cells with a cell wall or aggregates thereof or protoplasts, for example.

In the context of the invention, unless stated otherwise, a “plant” may be any species of dicotyledon, monocotyledon or gymnosperm plant. Preferably, the plants are monocotyledon plants and are of interest in agriculture or horticulture or for the production of bioenergy (bioethanol, biogas, etc). Examples are *Gossypium* sp., *Zea mays, Brachypodium distachyon, Triticum* sp., *Hordeum vulgare, Oryza sativa, Sorghum* sp., *Musa* sp., *Saccharum officinarum, Secale cereale, Avena* sp., turf grass and forage grass. A preferred plant in accordance with the invention is a plant from the genus *Zea*, in particular the species *Zea mays*, or *Sorghum*.

In connection with the present invention, the term “regulatory sequence” means a nucleotide sequence which influences the specificity and/or strength of expression, for example insofar as the regulatory sequence confers a specific tissue specificity. A regulatory sequence of this type may be localized upstream of the transcription initiation point of a minimum promoter, but also downstream thereof, for example in a transcribed but not translated leader sequence or within an intron.

The expression “resistance” or “resistant” as regards a pathogen should be understood to mean the ability of a plant or plant cell to resist the damaging effects of the pathogen and extends from a delay in the development of disease to complete suppression of the development of the disease. In connection with the present invention, a plant/plant cell is resistant or a plant/plant cell has a resistance to the pathogen *Helminthosporium turcicum* (*H. turcicum* or HT), i.e. to the leaf disease Northern Corn Leaf Blight (NCLB). The resistance is conferred by one or more proteins which are coded by a gene or by genes (resistance-conferring genes) from the accession Pepitilla. The resistance may be complete or partial and may be specific or non-specific to the pathogen race. In the event of a pathogen race-specific resistance, the virulent races of *Helminthosporium turcicum* may, for example, include N, 1N, 2N, 23N or 123N; the avirulent races may, for example, include 0, 1, 2, 3, 12, 23 or 123. A conferred resistance may be a newly inherited resistance or an increase in a partial resistance which is already extant.

A "transgenic plant" is a plant into the genome of which at least one polynucleotide, preferably a heterologous polynucleotide, has been integrated. Preferably, the polynucleotide has been integrated in a stable manner, which means that the integrated polynucleotide remains stable in the plant, is expressed and can also be stably inherited to descendants. The stable introduction of a polynucleotide into the genome of a plant also includes integration into the genome of a plant of the previous parental generation, whereby the polynucleotide can be further inherited in a stable manner. The term "heterologous" means that the introduced polynucleotide originates, for example, from a cell or an organism with another genetic background of the same species or from another species, or is homologous with the prokaryotic or eukaryotic host cell, but then is localized in a different genetic environment and thus is different from any possible corresponding naturally occurring polynucleotide. A heterologous polynucleotide can be present in addition to a corresponding endogenous gene.

Embodiments and variations of the present invention will now be described with reference to the accompanying figures and sequences in which:

FIG. 1: Calculated QTL region of 23.11 cM on chromosome 8 using 8 markers in 528 F2 individuals of the RP1×RP1 HTN1 cross. The black bars (HtN) show the confidence interval. Positions of the markers are in cM.

Figure 2:
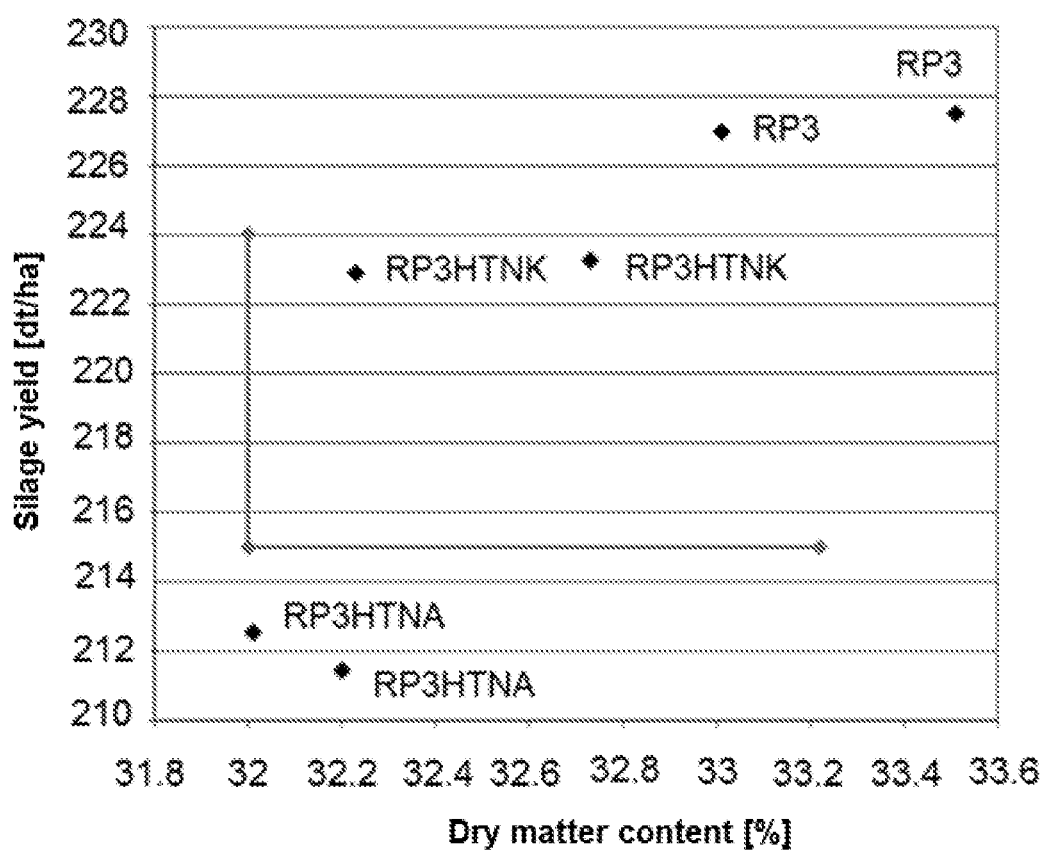

FIG. 2: Silage yield test on 5 locations in Germany and in two duplications, with the recurrent parent RP3 and the A version of the donor fragment from B37HTN1 (RP3HTNA) and the K version of the donor fragment from B37HTN1 (RP3HTNK). The bars show significant differences using the t-test, with p=0.05.

FIG. 3: Description of the marker regions M1 to M6 which define the chromosomal intervals (Int. 1 to Int. 5) which exhibit the resistance-conferring polynucleotide in the introgression lines and carry linkage drag in the chromosome fragment originating from the donor. Chromosomal segments of the donor (Pepitilla" are shown as dotted areas, those of the recurrent parent (without linkage drag) are shown as areas with diagonal stripes. Interval 1 (Int. 1) covers the resistance locus HTN1, interval 2 (Int. 2) covers sequence regions which are responsible in the donor for the linkage drag of the flowering time, intervals 4 and 5 (Int. 4 and Int. 5) cover sequence regions which are responsible for linkage drag of the silage yield in the donor.

Figure 4:
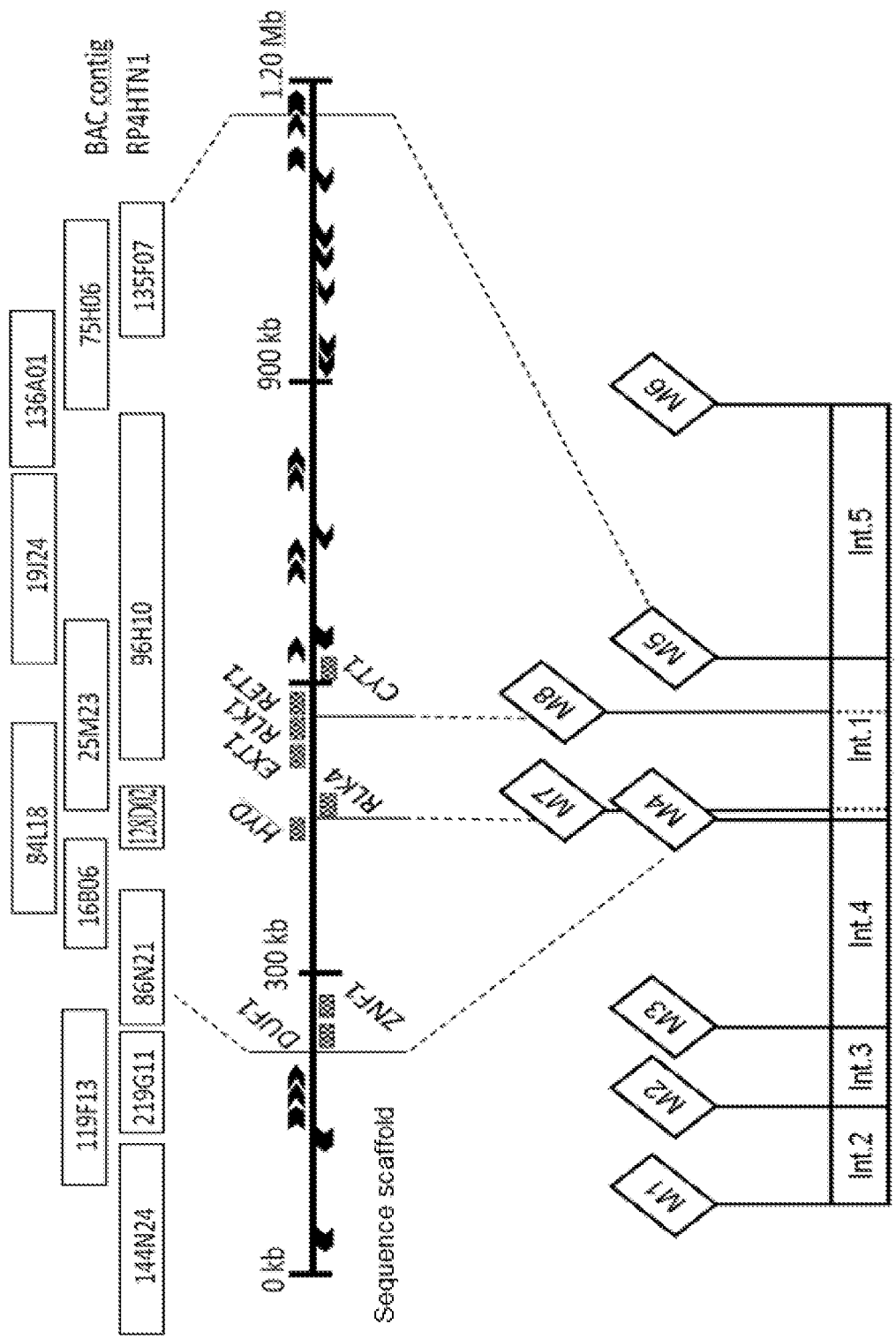

FIG. 4: BAC contig on its RP4HTN1 BAC bank with corresponding sequence scaffold and gene annotations. Candidate genes are shown in squared boxes. The black arrows represent further annotated genes which are not candidate genes for HTN resistance.

1. Phenotyping Experiments
A) Carrying out field trials to determine the HT resistance under natural and artificial inoculation/infection conditions and the flowering time:
At a location, at least 20 individuals per maize genotype to be investigated were planted out in a row. Inoculation was carried out naturally or artificially. Natural inoculation/infection was carried out using naturally occurring spores of *H. turcicum*. Artificial inoculation/infection was carried out using infected and ground leaf material which was administered to the plants to be tested. The latter type of inoculation allowed a comparable *H. turcicum* infestation to be simulated in different test years and at different locations independently of the prevailing natural infestation conditions there. A vulnerable parent and a parent with HTN1 introgression were cultivated from the donor B37HTN1 as control genotypes, depending on the test cross population. The classification score of the HT resistance feature was noted at least three times during the vegetative period. Only the classification score scheme shown in Table 3 was used.

The donor B37HTN1 as the source of HT resistance was crossed into various genetic backgrounds from elite lines with various levels of vulnerability to *H. turcicum* and near-isogenic lines were developed which were different from the vulnerable original lines essentially only by the introgression from B37HTN1. In phenotyping experiments, after artificial inoculation as described above, lines were selected which exhibited an improvement in the HT resistance by at least 2 to 3 classification scores, preferably 3 to 4 classification scores by introducing the resistance-conferring introgression from B37HTN1. The present invention will be described below in more detail by way of example using the two selected recurrent parents RP1 and RP3. The results for the phenotyping experiments described are summarized in Table 5. The recurrent parent RP1 without introgression exhibited average classification scores of 7 to 9, which were improved by 3 to 4 classification scores by the introgression from B37HTN1. The recurrent parent RP3 exhibited classification scores between 4 and 6 without introgression and an improvement of 2 to 3 classification scores by the introgression. The recurrent parent RP4 exhibited a classification score of 6 without introgression and an improvement of 2-3 classification scores by the introgression.

TABLE 5

Phenotyping data for HT resistance from genotypes RP1, RP3, and RP4 with and without resistance conferred introgression from B37HTN1 (classification scores were determined in accordance with the scheme in Table 3).

| Genotype | Average classification scores (n = 20) without introgression from B37HTN1 | Improvement in HT resistance with introgression from B37HTN1 |
| --- | --- | --- |
| RP1 | 7 to 9 | 3 to 4 |
| RP3 | 4 to 6 | 2 to 3 |
| RP4 | 6 | 2 to 3 |

In addition to the HT resistance, for each genotype the time of female and male flowering was determined as "days after sowing". The time for female flowering was determined by silk emergence; of male flowering by the appearance of panicles. The results are shown in more detail in Example 3.B).

B) Carrying out field trials to determine grain and silage yields:

In addition to the above data regarding HT resistance and flowering time, yield data for RP3 containing different lengths of resistance-conferring introgression fragments from B37HTN1 or Pepitilla and for a comparative elite line were determined. The lines RP3, RP3HTNA and RP3HTNK were dusted with a tester (flint maize, interpool single cross) of the complementary gene pool (flint maize) in order to produce seed stock for test hybrids. These test hybrids were each grown in duplicate in a field trial at five representative locations for maize crops in Germany. The test hybrids are well suited to these growing regions having regard to ripening. The field trial was carried out in two duplications in 4-row parcels 6 m in length and with a 0.75 m row separation. The density was 9 plants per m² in the first and 11 plants per m² in the second duplication. At the time of the silo maize harvest only the two central rows of each parcel were harvested in order to minimize competition effects. The weight per parcel and the water content were determined for the harvested material in order to calculate the silo maize yield (also known as the silage yield or the total dry matter yield) and the dry matter content (total dry matter content).

C) Carrying out greenhouse trials in order to determine the HT resistance:

20 individuals per genotype were grown in pots. The controls were genotypes of a vulnerable parent and a near-isogenic parent (NIL) with resistance-conferring introgression from B37HTN1, depending on the cross. 14 days after sowing, an artificial infection was carried out (see above). After a further 2 to 3 weeks, the first symptoms of disease developed. From the time of the appearance of the first symptoms, every other day the classification scores of the HT resistance feature as well as the number of plants with symptoms were determined. From this, the AUDPC (area under disease progress curve) was determined. The infestation frequency (as the %/time×period) was used to classify the plants under investigation; here, an AUDPC from 0-100 was resistant, 101-450 was heterozygous, and >450 was vulnerable.

2. Marker Development for the HTN1-Target-Region

In addition to the classification score tests, the target region around the HTN1 resistance locus on chromosome 8 (bin 8.06) in many genotypes was examined in more detail and mapped finely using novel and/or optimized molecular markers. The molecular markers used herein were developed on the basis of single nucleotide polymorphisms (SNP) or already publically available simple sequence repeat markers (SSR):

The DNA from the genotypes for use as markers was either isolated using the NucleoSpin 96 Plant II method following the manufacturer's instructions (MACHEREY-NAGEL GmbH & Co. KG, Germany) or using the Klear Gene DNA Extraction 384 method (LGC Genomics GmbH, Germany).

The primer sequences for the SSR markers were already known from the public database from the National Center for Biotechnology Information (NCBI); the primer sequences for the markers bnIg1782, umc1960, bnIg240, umc1121, bnIg1067 and umc1287, which were used to examine the target region, are summarized in Table 6, together with the modifications made.

TABLE 6

Primer sequences for the SSR marker (NED: 2'-chloro-5'-fluoro-7',8'-fused phenyl-1,4-dichloro-6-carboxyfluorescein; FAM: 6-carboxyfluorescein; M13: core sequence for phage M13)

| Marker | Forward primer sequence (5'-3') [SEQ ID NO] | Modification | Reverse primer sequence (5'-3') [SEQ ID NO] | Modification | Additional primer + Modification |
|---|---|---|---|---|---|
| bnlg1782 | 113 | NED | 114 | none | |
| umc1960 | 115 | NED | 116 | none | |
| bnlg240 | 117 | FAM | 118 | none | |
| umc1121 | 119 | FAM | 120 | none | |
| bnlg1067 | 121 | FAM | 122 | none | |
| umc1287 | 123 | none | 124 | none | M13 + FAM |

The volume of the PCR reaction mixture of bnlg1782, umc1960, bnlg240, umc1121 and bnlg1067 was 10 µl and consisted of a single concentration of the 4× buffer B (Solis BioDyne, Estonia), 0.5 pmol of the forward primer, 0.5 pmol of the reverse primer, 10-30 ng of DNA, 0.25 units of HotFirepol TAQ-Polymerase (Solis BioDyne, Estonia). The volume of the reaction mixture of umc1287 was 10 µl and consisted of a single concentration of the 4× bufferB (Solis BioDyne, Estonia), 0.5 pmol of the forward primer, 2.5 pmol of the reverse primer, 0.3 pmol of the additional primer M13, 10-30 ng of DNA, 0.25 units of HotFirepol TAQ-Polymerase (Solis BioDyne, Estonia).

The PCR reaction was carried out with an initial denaturing period of 900 seconds at 94° C., an amplification cycle of 25-40 cycles with 15 seconds at 94° C., 30 seconds at 50-55° C. and 120 seconds at 72° C., and a final step of 300 seconds at 72° C. Next, the PCR reaction was incubated for 2 h at 65° C. The PCR products were separated on an ABI3730xl (Life Technologies™, USA) following the manufacturer's instructions for the separation of 50-400 bp fragments.

The SNP markers were developed and used either (a) from publically available resources, (b) from a comparative amplicon sequencing or (c) from a sequence comparison of BAC sequences from RP4HTN1 (see Molecular Analysis segment) and B73 reference genome AGPv02 (www.maizesequence.org).

(a) SNPs were transformed into KASP markers (LGC Genomics GmbH, Germany) from the publically available SNP resource of the Maize Community 50K-Illiumina-Chip (Ganal et al., 2011). To this end, novel primers were developed which ensured the amplification of the decisive alleles in the KASP marker assay (see Table 4). The whole operation was carried out using Kraken™ Software (LGC Genomics GmbH, Germany). For a KASP marker assay, 5-20 ng DNA, 0.02 µl of an oligo assay mixture (12 µM primer allele 1 (forward); 12 µM of primer allele 2 (forward); 30 µM of reverse primer) and 1.5 µl of a 1×KASPar Reagent Kit for 1536 plates was used. A standard PCR setup consisted of 94° C. for 15 min, 10 cycles at 94° C. for 20 seconds, 61-55° C. touchdown for 1 minute, 26 cycles at 94° C. for 20 seconds and 55° C. for 1 minute. The evaluation of the alleles per genotype was carried out using Kraken™ software (LGC Genomics GmbH, Germany).

(b) The comparative amplicon sequencing was carried out using Sanger sequencing. The genotypes in the comparative sequences each comprised the donor B37HTN1 as well as B37, RP1, RP1 HTN1, RP3, RP3HTN1 (versions A, B, K), RP4, RP4HTN1. The DNA was isolated from ground grains using the CTAB method (Maniatis et al., 1982). The primer sequences for the amplicon sequencing are listed in Table 4. A standard PCR protocol for amplification of the corresponding regions consisted of denaturing at 94° C. for 5 minutes, 35 cycles each at 94° C. for 1 minute, 60° C. for 1 minute and 72° C. for 2 minutes and a subsequent step at 72° C. for 10 minutes. The PCR products were sequenced with the Sanger method (Sanger & Coulson, 1975). The sequence evaluation was carried out using DNAStar Lasergene software (DNASTAR Inc., USA). The detected polymorphisms were transformed into KASP markers as described in (a)

(c) The BAC sequence contigs were projected against the B73 reference genome AGPv02 using Blast algorithms in order to detect single nucleotide polymorphisms (SNP). The polymorphisms were detected using Lasergene software (DNASTAR Inc., USA) and are shown in Table 4 along with the flanking sequences. Primers were developed for the flanking sequences of an SNP and the identified SNPs were transformed into KASP markers as described in (a).

3. Localization of the HTN1 Resistance Locus on Chromosome 8 Using the SSR Marker A) Localization of the HTN1 resistance locus:

The HTN1 resistance locus from the B37HTN1 donors were crossed into elite lines as described in Example 1.A) and localized on chromosome 8 (bin 8.06) with the aid of the SSR and SNP markers from Example 2 (see FIG. 1). NILs from the crosses RP1×RP1 HTN1 and RP3×RP3HTN1 were phenotyped at two locations over several years with two duplications under natural infection conditions using the classification score scheme of Table 3. The NILs showed, on average, a resistance response which was improved by 4 classification scores compared with the original line. The development of local lesions on the leaves was shifted by approximately 2 weeks compared with the vulnerable genotype. QTL mapping was carried out with 528 F2 individuals (RP1× RP1 HTN1 cross) using the 8 markers (Tables 4 and 6 are from the QTL mapping markers of FIG. 1). The QTL region which covered the HTN1 resistance locus was localized on chromosome 8 between the markers MA0002 and umc1287, in a 23.1 cM region.

B) Crossing the B37HTN1 donor fragment into an elite maize line and identification and elimination of linkage drag for delayed flowering time:

The donor B37HTN1 was crossed with KWS.elite, an elite maize line from KWS SAAT AG (Germany) and then backcrossed over five generations with KWS.elite. In each backcross generation, molecular markers were used in order to select plants which were heterozygous for the HTN target region. Next, a selected plant from the fifth backcross generation was self-fertilized and homozygous plants for the HTN target region were identified with molecular markers.

These lines were tested in field trials at several locations. In this regard, for the genotypes B37HTN1, KWS.elite and KWS.elite.B37HTN1, the phenotypical data of HT resistance and the flowering times were determined as described in Example 1. The genotypes with HTN1 introgression exhibited the expected HT resistance with classification scores of 1 to 3, while the original line KWS.elite exhibited classification scores of 5-7. Unexpectedly, in addition, compared with the KWS.elite, the KWS.elite.B37HTN1 exhibited a flowering time both for the female and for the male flowers which was shifted by at least 2 days. These shifted flowering times constitute a negative agronomic feature for maize based on linkage drag which has not yet been described in this form following introgression of HT resistance from B37HTN1. Marker analyses found the localization of the linkage drag which is responsible for the delayed flowering time to be in a region between two marker regions on the introgression from B37HTN1, between M1 and M2. In this regard, the genotypes B37HTN1, KWS.elite and KWS.elite.B37HTN1 were, for example, analysed with the KASP markers SYN14136, PZE-108076510, SYN24931 and PZE-108077560 (see FIG. 3 and Table 4). SYN14136 and PZE-108076510 were used for the specific detection of the marker region M1, SYN24931 and PZE-108077560 for the specific detection of the region M2. According to this, the marker region M1 lies 5' from the locus of the linkage drag and the marker region M2 is 3' thereto. The marker analysis showed that B37HTN1 and KWS.elite.B37HTN1, both with a flowering delayed by two days, exhibited common alleles for the regions M1 and M2 as well as the interval between these regions, while KWS.elite has a normal flowering time and has other alleles for the regions M1 and M2 and the interval between them.

The donor B37HTN1 was crossed with RP3 and then backcrossed over three generations with RP3. Molecular markers were used in each backcross generation. Initially, plants which were heterozygous for the HTN1 target region were selected and then these plants were investigated with markers which were distributed uniformly over the genome in order to select against the donor genome. Next, a selected plant from the third backcross generation was self-fertilized and homozygous plants for the HTN1 target region were identified with molecular markers.

Furthermore, the donor B37HTN1 was also crossed with the recurrent parent RP3 and RP4 and a RP3HTNA and RP4HTNA line produced over several backcrossing steps. The phenotyping on HT resistance showed an improvement in the classification scores of 5 to 7 for the original line RP3 to 1 to 3 for RP3HTNA and an improvement in the classification scores from 6 for the original line RP4 to 2 to 3 for RP4HTNA. The phenotyping for flowering time exhibited comparable flowering times for RP3 and RP3HTNA and RP4 and RP4HTNA. Using the KASP markers SYN14136, PZE-108076510, SYN24931 and PZE-108077560 showed that RP3 and RP3HTNA carry common alleles for the regions M1 and M2. These did not correspond to the donor B37HTN1. As a result, then, the flowering time-delaying chromosomal segment of the introgression from B37HTN1 lies on a chromosomal interval between the marker regions M1 and M2. With the line RP3HTNA, then, this linkage drag was successfully removed. The KASP markers used, SYN14136, PZE-108076510, SYN24931 and PZE-108077560, proved to be effective tools for "assisted selection".

Phenotyping of RP3 and RP3HTNA also comprised recording the grain and silage yield. While the grain yield in the genotypes was not significantly different, the silage yield feature in RP3HTNA exhibited an unequivocal, statistically significant reduction of at least 14 decitonnes per hectare (dt/ha) over RP3, or a reduction of more than 5%.

With the aid of the designed KASP markers SYN14136, PZE-108076510, SYN24931 and PZE-108077560, a RP1HTN1 line could be selected from the cross of B37HTN1 and the recurrent parent RP1 which did not exhibit any more flowering time-delaying linkage drag, but rather a silage yield reduction, as was observed for RP3HTNA. For the purposes of more accurate molecular characterization, RP1HTN1 was developed further and a F2 population was set up with 724 individuals from the cross RP1×RP1 HTN1. Next, the F3 generation was self-fertilized and selected F4 plants were genotyped and phenotyped. Genotyping was carried out using markers from Table 6 in the detected QTL region of 23.1 cM. Phenotyping was carried out at several locations in two duplications (see Example 1). Recombinant plants for the QTL region were selected and correlated with the phenotype data. The selection comprised plants which covered different regions of the target region as well as heterozygous plants, with the aim of obtaining new recombinant plants. Each year, two backcrosses with RP1 were carried out and individual plants were selected, and thus new recombinants were produced. New recombinants were phenotyped in field and greenhouse tests (see under 1.) and genotyped for the development of novel molecular markers in accordance with 2.

The use of these novel markers on the RP3HTNA genotype allowed a marker region M3 to be identified which limited the introgression in the 5' region and can be described with the flanking markers PZE-108093423 and PZE-108093748. In this regard, PZE-108093423 should exhibit the alleles of the recurrent parent RP3 and PZE-108093748 should exhibit the alleles of the donor B37HTN1. In the 3' region, the introgression of RP3HTNA by the markers PZE-108107671 and SYN4196 in a further marker region M6 is described (see FIG. 3). In this regard, PZE-108107671 carries the alleles of the donor B37HTN1 and SYN4196 carries the alleles of the recurrent parent RP3. The introgression from RP3HTNA (hereinafter termed version A) corresponds, between the marker regions M3 and M6, to the donor B37HTN1, but outside this region it corresponds to the recurrent parent or another line which does not carry the alleles in the region of the donor B37HTN1 between M1 and M2. This version A was introduced into various other genetic backgrounds and fresh yield tests, resistance phenotyping and flowering time determinations were undertaken. The results were comparable with those described for RP3HTNA. Thus, the flowering time was not shifted compared with the corresponding line without introgression and the line exhibited an improved resistance to *Helminthosporium turcicum* compared with the original line, or at least the reduction of the silage yield.

C) Identification and elimination of linkage drag for reduced silage yield:

The donor used was the RP3HTNA line. This was crossed with RP3 and self-fertilized over six further generations. In each self-fertilization generation, molecular markers were used in the target region in order to reduce the donor fragment. Since all regions of the genome outside the target region had already been selected in the RP3HTNA line on the RP3 genome, only the region around the HTN target region was investigated with markers. In this regard, homozygous plants were identified for a reduced HTN target region. At the same time, intensive marker development was carried out in the target region. In addition to many others, a RP3HTNK line was identified which described the B37HTN1 donor fragment from a marker region M4 flanked by the markers MA0004 and MA0005, wherein MA0004 describes the alleles of the recurrent parent RP3 and MA0005 describes the alleles of the donor B37HTN1 in RP3HTNK, up to a marker region M5, flanked by the markers MA0006 and PZE-108097482, wherein MA0006 describes the alleles of the donor B37HTN1 and PZE-108097482 describes the alleles of the recurrent parent RP3. In RP3HTNK, the introgression from RP3HTNK (hereinafter termed version K) causes an improved HTN1 resistance of 3 to 4 classification scores compared with RP3, the same flowering time as its original line RP3 (no delay in flowering) and no further significant reduction in the silage yield (see FIG. 2). In addition, with the aid of the described markers, linkage drag-free lines could be produced from the original line RP1 by crossing, which lines exhibited version K of the introgression.

D) Resistance-conferring haplotype from B37HTN1 or from Pepitilla

Version K possesses a haplotype from B37HTN1 or from Pepitilla which carries the donor alleles described in Table 4 at the physical positions with respect to B73 AGPv02 in bp. As an example, the haplotype at marker MA0008 will be described: using the marker MA0008 and specifying the alleles for B37HTN1, RP3, RP3HTNA, RP3HTNK, then the allele "T" is for B37HTN1, RP3HTNA, RP3HTNK and the allele "C" is for RP3. For this locus, this marker also distinguishes the assumed HTN1 resistance source PH99N (WO 2011/163590), which also contains an allele "C" at this position, from the resistance source used here.

4. Molecular Analysis of the Fine-Mapped Region

Furthermore, the chromosome fragment which had been inserted and truncated by introgression was investigated on a molecular level. The resistance locus Htn1 from the accession Pepitilla was thus reduced to a distinct target region, a chromosome interval of 700 kb, and sequenced in the genotype RP4HTN1. As will be described in more detail below, BAC clones from RP4HTN1 were isolated, sequenced and assembled into a sequence scaffold. The sequence scaffold was annotated and the annotated genes in this interval were set against EST/cDNA sequence information. Differential expression studies were then carried out from a multiplicity of annotated genes to identify the candidate genes (see Table 1).

A) BAC bank and pool construction, BAC bank screening, BAC sequencing

A BAC bank was produced from the genotype RP4HTN1. This was followed by constructing the BAC bank and the 3D matrix pool from leaf material as well as by screening the 3D matrix pool. The primers for screening the 3D matrix pool were based on the B73 AGPv01 sequence from 149957158 bp to 152977351 bp on chromosome 8 (www.maizesequence.org) and the primer program 3. The parameters for the primer selection were a mean GC content of 50%, primer length of 20-25 bp, melting temperature between 70-90° C. and amplicon length between 70-80 bp. Using the primer pairs in Table 7, the 3D pools were screened using RT-PCR. The values of the two parameters, namely melting temperature and CP value, are given for the BAC clone. 26 BAC clones could be identified for the selected region. All BAC clones were isolated from the BAC bank and used as *E. coli* culture for DNA isolation and sequencing. Sequencing was carried out with a standard GS-FLX titanium kit (454 Life Sciences, USA). The sequence information obtained for the BAC clones 144N24, 119F13, 219G11, 86N21, 16606, 84L18, 128D02, 25M23, 96H10, 19J24, 136A01, 75H06, 135F07 is summarized in Table 8.

TABLE 7

Primer pairs for detection of BAC clones from the RP4HTN BAC bank

| BAC clone ID | Primer pair 1 Primer pair 2 | Sequence, primer pair 1 (5'-3') | Melting temp, ° C. (50% of amplicon is single stranded) in genotype RP4HTN1 | CP value (cycle when the exponential phase of the PCR begins) | Amplicon size (bp) |
|---|---|---|---|---|---|
| 58A14 | 579ZMPM0_2F; 579ZMPM0_2R | 125; 126 | 77.4 | 28.5 | 74 |
|  | 579ZMPM0_4F; 579ZMPM0_4R | 127; 128 | 80.96 | 26.52 | 77 |
| 144N24 | 579ZMPM0_5F; 579ZMPM0_5R | 129; 130 | 79.09 | 27.09 | 76 |
|  | 579ZMPM0_17F; 579ZMPM0_17R | 131; 132 | 83.06 | 25.53 | 78 |
| 219G11 | 579ZMPM0_16F; 579ZMPM0_16R | 133; 134 | 84.7 | 25.96 | 78 |
|  | 579ZMPM0_25F; 579ZMPM0_25R | 135; 136 | 78.95 | 26.09 | 80 |
| 119F13 | 579ZMPM0_22F; 579ZMPM0_22R | 137; 138 | 80.89 | 25.98 | 73 |
|  | 579ZMPM0_34F; 579ZMPM0_34R | 139; 140 | 80.1 | 24.43 | 76 |
| 86N21 | 579ZMPM0_35F; 579ZMPM0_35R | 141; 142 | 80.9 | 25.27 | 70 |
|  | 579ZMPM0_38F; 579ZMPM0_38R | 143; 144 | 83.86 | 26.01 | 71 |
| 16B6 | 579ZMPM0_37F; 579ZMPM0_37R | 145; 146 | 79.22 | 25.71 | 80 |
|  | 579ZMPM0_41F; 579ZMPM0_41R | 147; 148 | 75.93 | 26.6 | 74 |
| 84L18 | 579ZMPM0_41F; 579ZMPM0_41R | 149; 150 | 75.93 | 26.6 | 74 |
|  | 579ZMPM0_46F; 579ZMPM0_46R | 151; 152 | 80.54 | 25.68 | 78 |
| 128D2 | 579ZMPM0_180F; 579ZMPM0_180R2 | 153; 154 | 84.41 | 25.99 | 77 |
|  | 579ZMPM0_48F; 579ZMPM0_48R | 155; 156 | 83.96 | 25.33 | 77 |
| 25M23 | 579ZMPM0_48F; 579ZMPM0_48R | 157; 158 | 83.96 | 25.33 | 77 |
|  | 579ZMPM0_56F; 579ZMPM0_56R | 159; 160 | 77 | 29.12 | 79 |
| 19J24 | 579ZMPM0_51F; 579ZMPM0_51R | 161; 162 | 87.76 | 27.75 | 77 |
|  | 579ZMPM0_199F; 579ZMPM0_199R | 163; 164 | 82.49 | 26.56 | 79 |
| 96H10 | 579ZMPM0_63F; 579ZMPM0_63R | 165; 166 | 85.78 | 26.08 | 63 |
|  | 579ZMPM0_208F; 579ZMPM0_208R | 167; 168 | 79.87 | 26.84 | 79 |
| 136A1 | 579ZMPM0_206F; 579ZMPM0_206R | 169; 170 | 89.81 | 32.09 | 70 |
|  | 579ZMPM0_86F; 579ZMPM0_86R | 171; 172 | 81.81 | 30.07 | 71 |
| 135F7 | 579ZMPM0_79F; 579ZMPM0_79R | 173; 174 | 75.82 | 25.43 | 72 |
|  | 579ZMPM0_278F; 579ZMPM0_278R | 175; 176 | 78.13 | 22.69 | 78 |

TABLE 7-continued

Primer pairs for detection of BAC clones from the RP4HTN BAC bank

| BAC clone ID | Primer pair 1 Primer pair 2 | Sequence, primer pair 1 (5'-3') | Melting temp, °C. (50% of amplicon is single stranded) in genotype RP4HTN1 | CP value (cycle when the exponential phase of the PCR begins) | Amplicon size (bp) |
|---|---|---|---|---|---|
| 75H6 | 579ZMPM0_209F; 579ZMPM0_209R | 177; 178 | 75.41 | 24.93 | 77 |
|  | 579ZMPM0_86F; 579ZMPM0_86R | 179; 180 | 81.81 | 30.07 | 71 |
| 117O2 | 579ZMPM0_87F; 579ZMPM0_87R | 181; 182 | 81.89 | 27.7 | 76 |
|  | 579ZMPM0_91F; 579ZMPM0_91R | 183; 184 | 80.13 | 26.93 | 75 |
| 173H23 | 579ZMPM0_216F; 579ZMPM0_216R | 185; 186 | 82.3 | 25.76 | 80 |
|  | 579ZMPM0_95F; 579ZMPM0_95R | 187; 188 | 79.5 | 24.97 | 73 |
| 118N19 | 579ZMPM0_99F; 579ZMPM0_99R | 189; 190 | 76.84 | 24.69 | 80 |
|  | 579ZMPM0_244F; 579ZMPM0_244R | 191; 192 | 80.07 | 25.38 | 80 |
| 42L23 | 579ZMPM0_241F; 579ZMPM0_241R | 193; 194 | 81.16 | 25.79 | 79 |
|  | 579ZMPM0_109F; 579ZMPM0_109R | 195; 196 | 77.89 | 25.28 | 74 |
| 112N13 | 579ZMPM0_109F; 579ZMPM0_109R | 197; 198 | 77.89 | 25.28 | 74 |
|  | 579ZMPM0_247F; 579ZMPM0_247R | 199; 200 | 80.76 | 24.82 | 71 |
| 97K23 | 579ZMPM0_112F; 579ZMPM0_112R | 201; 202 | 79.22 | 25.2 | 77 |
|  | 579ZMPM0_125F; 579ZMPM0_125R | 203; 204 | 83.44 | 28.17 | 74 |
| 18J17 | 579ZMPM0_253F; 579ZMPM0_253R | 205; 206 | 77.5 | 32.34 | 71 |
|  | 579ZMPM0_125F; 579ZMPM0_125R | 207; 208 | 83.44 | 28.17 | 74 |
| 5M22 | 579ZMPM0_128F; 579ZMPM0_128R | 209; 210 | 77.99 | 24.05 | 77 |
|  | 579ZMPM0_136F; 579ZMPM0_136R | 211; 212 | 78.65 | 26.46 | 78 |
| 146I6 | 579ZMPM0_131F; 579ZMPM0_131R | 213; 214 | 76.58 | 26.54 | 78 |
|  | 579ZMPM0_137F; 579ZMPM0_137R | 215; 216 | 83.7 | 25.42 | 73 |
| 147O15 | 579ZMPM0_138F; 579ZMPM0_138R | 217; 218 | 79.38 | 24.8 | 79 |
|  | 579ZMPM0_147F; 579ZMPM0_147R | 219; 220 | 79.63 | 26.77 | 80 |
| 88K17 | 579ZMPM0_145F; 579ZMPM0_145R | 221; 222 | 81.51 | 27.61 | 76 |
|  | 579ZMPM0_262F; 579ZMPM0_262R | 223; 224 | 75.7 | 25.82 | 80 |
| 180G22 | 579ZMPM0_161F; 579ZMPM0_161R | 225; 226 | 80.21 | 25.16 | 73 |
|  | 579ZMPM0_265F; 579ZMPM0_265R | 227; 228 | 79.3 | 24.7 | 79 |

TABLE 8

Sequence content of the 13 analysed BAC clones

| BAC | # Reads | # Reads without E. coli | Sequence quantity in bp | Sequence quantity in bp without E. coli |
|---|---|---|---|---|
| 144N24 | 10967 | 10849 | 3646226 | 3591222 |
| 119F13 | 17987 | 17847 | 6033910 | 5957456 |
| 219G11 | 32904 | 32484 | 10553629 | 10381924 |
| 86N21 | 39606 | 39106 | 12991596 | 12750077 |
| 16B06 | 36198 | 35849 | 12523123 | 12357036 |
| 84L18 | 50537 | 34162 | 15991645 | 10776458 |
| 128D02 | 15998 | 15847 | 5138442 | 5064677 |
| 25M23 | 22551 | 22416 | 7864493 | 7786402 |
| 96H10 | 7723 | 7614 | 2569604 | 2525488 |
| 19J24 | 21953 | 21775 | 7327364 | 7234315 |

TABLE 8-continued

Sequence content of the 13 analysed BAC clones

| BAC | # Reads | # Reads without E. coli | Sequence quantity in bp | Sequence quantity in bp without E. coli |
|---|---|---|---|---|
| 136A01 | 31998 | 31724 | 10298869 | 10158900 |
| 75H06 | 24345 | 24121 | 8021727 | 7920125 |
| 135F07 | 29702 | 29484 | 9721708 | 9604010 |

B) BAC sequence assembly, annotation and candidate gene selection:

Production of a sequence scaffold: the BAC clones 144N24, 119F13, 219G11, 86N21, 16B06, 84L18, 128D02, 25M23, 19J24, 96H10, 136A01, 75H06, 137F07 were sequenced using the 454 technique (Margulies et al., 2005).

Automatic assembly of the raw sequences of the BAC clones was carried out with the "Newbler" software (454 runAssembly software, software release 2.3). The pro BAC sequence contigs produced in this manner were arranged correctly by manual analysis, in which the following techniques were applied:

1. Sequences of overlapping BACs could be roughly divided into overlapping and non-overlapping zones.
2. Sequence contigs from various overlapping BACs were compared in the overlapping zones. Approximately 20% of the sequence contigs could be arranged in this manner and gaps between them could be closed (for example when a contig of one BAC covered or connected to two contigs of the other BACs).
3. All sequence contigs were manually annotated. In this regard, initially only repetitive elements (transposons and retrotransposons, abbreviated to "TEs") were annotated. Since sequence gaps occur primarily in TEs, the TE annotation can help to correctly arrange sequence contigs. This means that when one end of a TE is on one sequence contig and the other end is on another, the two contigs can be ordered appropriately. In such cases, a sequence of 100 Ns is respectively inserted in order to fill the gaps between the sequence contigs. In addition, the information from TEs which are nested (i.e. TEs which have been inserted into other TEs) was used in order to arrange sequence contigs.
4. In some zones, neither information from overlapping BACs nor TE annotations could be used (this was the case, for example, in zones which were only covered by one BAC). Here, the sequence contigs were arbitrarily arranged and the gaps between them filled with sequences of 200 Ns.
5. Many of the TEs in the maize genome are "long terminal repeat" (LTR) retrotransposons which are flanked by long (1-2 kb) LTR sequences. These LTRs may be up to 100% identical. In some cases, then, raw sequences of the two LTRs were assembled into a consensus sequence (i.e. a copy of the LTR is not present in the assembly). In these cases, the sequence gaps were filled with the number of Ns which would correspond to the length of the second LTR.
6. Genes were manually annotated. To this end, the coding sequences (CDS) for the published B73 maize genome was used as the reference (www.maizegdb.org/gene_model.php). The CDS were aligned with the RP4HTN sequence using DotPlot (www.dotplot.org/) and so the positions of exons and introns were determined. Candidate genes were on the one hand determined by describing their function (if publically known). On the other hand, the CDS of the resistant RP4HTN was compared with the vulnerable B73 AGPv02. If differences occurred, the respective gene was placed in the list of candidates. The prepared sequence had a length of 1'328'253 bp. The list of candidate genes is given in Table 1.

5. Molecular Analysis of the Candidate Genes:

Expression analysis: the expression of the various candidate genes was tested on 21 day old (following sowing), uninfected plants (infection day=0 dpi) and also at 36 days old with plants which had been infected and also which had not been infected with *H. turcicum* (15 days after infection=15 dpi inf/ni).

RNA from the second leaf was extracted from the tested maize plants, reverse transcribed into cDNA and the expression was measured using qPCR. In each case the second leaf was harvested, frozen and the RNA was extracted, quantified and tested for quality and purity using the SV Total RNA Isolation System Kit (Z3100; Promega, Dübendorf, Switzerland), exactly as described (Brunner et al., 2011; Risk et al., 2012).

1 µg of RNA was reverse transcribed using the iScript RT Supermix (170-8841; Bio-Rad, Cressier, Switzerland) in a reaction volume of 20 µl, following the manufacturer's instructions. In order to exclude the possibility of contamination by genomic DNA (RT minus), at the same time, a reaction without adding the reverse transcriptase was incubated for each sample.

Quantitative Real Time PCR (RT-qPCR) was carried out in technical triplicate or duplicate in a reaction volume of 10 µl and with the addition of 4 µl of 1:10 diluted (10 mM Tris HCL pH8, 0.1 mM EDTA) cDNA, 5 µl of SsoFast EvaGreen® Supermix (172-5201; Bio-Rad, Switzerland) and a primer concentration of 400 nM on the C1000 Touch Cycler (Bio-Rad, Switzerland). For amplification, the following program was used: 95° C. for 30 seconds, followed by 40 cycles at 95° C. for 3 seconds, then 60-63° C. (see Table 2) for 5 seconds. To analyse the melting curve (exclusion of primer dimers), the PCR product was heated in 0.5° C. steps from 65° C. to 95° C. Amplification curves and melting curves were checked in the CFX Manager V 3.0 (Bio-Rad, Switzerland) program and the Cq values (quantification cycle) were exported into the qbasePLUS V 2.3 (Biogazelle, Zwijnaarde, Belgium) program to determine the relative expressions.

The primers for the candidate genes were determined with the aid of primer-BLAST (www.ncbi.nlm.nih.gov/tools/primer-blast/), in order, as far as possible, to exclude non-specific amplification on transcripts which were already known. In order to evaluate suitable amplicons, the PCR products were separated using agarose gel electrophoresis and their sizes were examined using isolated bands. Furthermore, amplicons from RP1 HtN and also NILHtN as set out in Table 1 were sequenced. In order to normalize the expression data, 1-3 reference genes (LUG, MEP, FPGS) were used (Manoli et al., 2012).

All of the candidate genes were expressed in the vulnerable genotype RP1 and in the resistant genotype RP1 HTN. A differential expression between RP1 and RP1 HTN could be demonstrated for RLK1. RLK1 in the vulnerable plants is expressed up to 4 times more strongly than in the resistant plants.

TABLE 9

Primer pairs for candidate genes, with their amplicon length in bp and the appropriate annealing temperature.

| Gene name | Primer name | SEQ ID No: | Primer sequences (F = Forward sequence; R = Reverse sequence) | Length (in bp) in RP1 | Length (in bp) in RP1HTN | Annealing temperature |
|---|---|---|---|---|---|---|
| ZNF1 | GH034 | 229 | F: TGGTTGGTGTCGAAGCTGAG | 130 | 130 | 60° C. |
|  | GH033 | 230 | R: ATTTATCCCGGCCTTTGCAT |  |  |  |
| HYD | GH039 | 231 | F: GATCTACAGGGAAGCCCACTGA | 74 | 74 | 60° C. |
|  | GH040 | 232 | R: TTTTTCCTTGAGGCAGTTATATGCT |  |  |  |
| RLK4 | GH220 | 233 | F: TTGTGCAGCGGAGGGAA | 91 | 85 | 63° C. |
|  | GH221 | 234 | R: CCAGGGCACCAGCAAGAAT |  |  |  |
| EXT1 | GH168 | 235 | F: CGACTACAAGACGCGTACC | 103 | 103 | 60° C. |
|  | GH170 | 236 | R: GGTGTCGATGGTGAGGTTC |  |  |  |
| RLK1 | GH138 | 237 | F: TATTGTTGGTGCTGTTGCCG | 121 | 121 | 60° C. |
|  | GH139 | 238 | R: GGACTCAATCCTTGTCCCTG |  |  |  |
| RET1 | GH055 | 239 | F: CGCTCGTTTGCCAGATAGCC | 165 | 165 | 60° C. |
|  | GH056 | 240 | R: CACGGTGTGTGCCAGTTTGT |  |  |  |

TILLING population screening and detection of mutants: For the candidate genes (Table 1), screening of a TILLING population of 10000 plants which carries the introgression from Pepitilla on chromosome 8 in the region from 15688552-153139596 bp compared to the B73 reference AGPv02 (www.maizesequence.org) (RP3HTN1) and which exhibits a resistance to Helminthosporium turcicum was carried out. The mutations could be either silent nucleotide exchanges, amino acid exchanges or stop codons and acted to detect the function of the candidate genes.

Transformation: Candidate genes could, for example, be introduced into the vulnerable genotype A188 by means of Agrobacterium tumefaciens-conferred transformation. This genotype is characterized by AUDPC values of 702 in the GWH-Test (n=18 plants), so that a transformation with the resistance gene produces a clear resistance response.

6. Determination of Race Specificity: Proof that HTN1 Also Confers Race-Non-Specific Resistance Screening of the genotypes with the HtN gene was carried out at many locations in all of the infestation regions of Europe. Until now, this resistance has not been broken, so that we started with the assumption that until now they were not race-specific until a race N was found. Race 1 predominates in Europe, but in some individual regions, races 2 or 3 or a combination thereof could be detected (Hanekamp et al., 2013).

7. Phenotype Test on Other Recombination Plants

New recombination plants were tested for the QTL region and correlated with the phenotype data. The selection comprised plants which covered different regions of the target region. Recombinant plants could be identified which exhibited an introgression of the donor B37HTN1 between the markers MA0005 and MA0021—marker region M7 and the markers MA0013 and MA0022—marker region M8, in the genetic background of RP1. FIG. 4 shows that this region only comprises the three genes RLK4, EXT1 and RLK1. These recombination plants, which comprise the region M7-M8, exhibit the resistance phenotype both in the field with artificial inoculation and also in the greenhouse test.

8. Identification of the Resistance-Conferring Candidate Gene

In order to identify the resistance-conferring gene, screening of the TILLING population of 10000 plants which exhibited the introgression from Pepitilla on chromosome 8 in the region from 15688552-153139596 bp compared with the B73 reference AGPv02 (www.genome.arizona.edu) (RP3HTN1) and a resistance to Helminthosporium turcicum was carried out.

Amplicons were developed for genes RLK4 and RLK1 (Table 10) and after amplification of the individual plant DNA of the TILLING population, these were sequenced by means of Sanger sequencing.

TABLE 10

Primer sequences for amplicons

| Gene name | Primer name | SEQ ID NO: | Primer Sequences F = Forward sequence; R = Reverse sequence | Length of amplicons (in bp) | Annealing temperature (° C.) |
|---|---|---|---|---|---|
| RLK4 | MA04916-6f | 247 | F: TGTTTCAGGAATCACGCAACTGGA | 399 | 60 |
|  | MA04916-6r | 248 | R: GCACCACGCCATGACCAACATC |  |  |

TABLE 10-continued

Primer sequences for amplicons

| Gene name | Primer name | SEQ ID NO: | Primer Sequences F = Forward sequence; R = Reverse sequence | Length of amplicons (in bp) | Annealing temperature (° C.) |
|---|---|---|---|---|---|
| RLK1 | TG10013-10.f | 249 | F: CTTCCTACAGAAGAA CGAGAGT | 804 | 60 |
|  | TG10013-11.r | 250 | R: TTCCTCACGAGCTCT GTGGTC |  |  |

The amplicon sequences were evaluated using DNAS-TAR Lasergene software and base mutations were identified. Table 11 lists a selection of the mutations found.

TABLE 11

Identified mutations for the genes RLK4 and RLK1

| Gene name | Mutation name | Position of the mutation in cDNA of RP3HTN1 (bp) | Base exchange | Position of mutation in protein sequence of RP3HTN1 (bp) | Amino acid exchange effect |
|---|---|---|---|---|---|
| RLK4 | RLK4d | 977 in SEQ ID NO: 3 | G > A | 326 in SEQ ID NO: 4 | G > D |
|  | RLK4f | 1169 in SEQ ID NO: 3 | C > T | 390 in SEQ ID NO: 4 | T > I |
| RLK1 | RLK1b | 1365 in SEQ ID NO: 1 | G > A | 455 in SEQ ID NO: 2 | M > I |
|  | RLK1d | 1490 in SEQ ID NO: 1 | G > A | 497 in SEQ ID NO: 2 | G > E |

The identified mutants were self-fertilized in the greenhouse and seed stock was harvested from the homozygous plants with the wild type allele and mutation allele per mutation event for a phenotype test.

15 homozygous individual plants with a wild type allele and mutation allele for the mutants RLK1 b, RLK1 d, RLK4d and RLK4f and the controls RP1 and RP1 HTN1 were inoculated with *H. turcicum* as described above, in a greenhouse. In the period from 11 to 25 days following inoculation, the infestation was determined every day. The AUDPC values for all of the test plants are summarized in Table 12. Changing the amino acid in the resistant parent of the RP3HTN1 TILLING population was expected to make the homozygous mutants vulnerable.

TABLE 12

AUDPC values for homozygous plants with wild type allele and mutation allele of the genes RLK1 and RLK4. In the phenotype column, 0-100 means resistant, 101-450 means heterozygous, and >450 means vulnerable.

| Mutant name | Alleles | AUDPC | Phenotype |
|---|---|---|---|
| RLK4d | Hom. Mutant | 33.3 | resistant |
|  | Hom. Wild type | 0.0 | resistant |
| RLK4f | Hom. Mutant | 46.7 | resistant |
|  | Hom. Wild type | 96.7 | resistant |
| RLK1b | Hom. Mutant | 346.7 | heterozygous |
|  | Hom. Wild type | 46.4 | resistant |
| RLK1d | Hom. Mutant | 406.7 | heterozygous |
|  | Hom. Wild type | 83.3 | resistant |
| RP1 |  | 1030.0 | vulnerable |
| RP1HTN1 |  | 0.0 | resistant |

REFERENCES

Bar-Zur, A, Tadmor, Y, Juvik, J A, Shimoni, M, & Reuveni, R (1998). "Resistance to northern leaf blight in maize (*Zea mays*) conditioned by the HtN gene and the association with isoperoxidases." *Canadian Journal of Plant Pathology* 20(1): 28-34.

Brunner, S., Hurni, S., Herren, G., Kalinina, O., from Burg, S., Zeller, S. L., Schmid, B., Winzeler, M. and Keller, B. (2011) Transgenic Pm3b wheat lines show resistance to powdery mildew in the field. *Plant Biotechnology Journal*, no-no.

Chevalier, B S, Kortemme, T, Chadsey, M S, Baker, D, Monnat, R J, Stoddard, B L (2002). "Design, activity, and structure of a highly specific artificial endonuclease". *Mol. Cell* 10 (4): 895-905. doi:10.1016/S1097-2765(02) 00690-1.

Carson, M L (1995) "A new gene in maize conferring the chlorotic halo reaction to infection by *Exserohilum turcicum*. *Plant Disease* 79: 717-720.

Chung, C-L, Poland, J, Wisser, R, Kolkman, J, and Nelson, R (2008). "Analysis of qEt8.06, a Major QTL for Resistance to Northern Leaf Blight in Maize" Poster, Annual Research Meeting of Generation Challenge Programme, Bangkok, Thailand. www.plantpath.cornell.edu/labs/nelson_r/Docs/01_CLC_08 GCP_12 Sep08_2.pdf Chung, C-L, Jamann, T, Longfellow, J and Nelson, R (2010). "Characterization and fine-mapping of a resistance locus for northern leaf blight in maize bin 8.06" *Theoretical and Applied Genetics* 121(2): 205-227.

Coates, S T and White D G (1998). "Inheritance of resistance to gray leaf spot in crosses involving selected resistant inbred lines of corn." *Phytopathology* 88(9): 972-982.

Depicker A, Stachel S, Dhaese P, Zambryski P, Goodman H M (1982) Nopaline synthase: transcript mapping and DNA sequence. J Mol Appl Genet. 1(6): 561-73.

Ferguson, L M and Carson M L (2007). "Temporal Variation in *Setosphaeria turcica* Between 1974 and 1994 and Origin of Races 1, 23, and 23N in the United States." *Phytopathology* 97: 1501-1511.

Gevers, H O (1975). "A new major gene for resistance to *Helminthosporium turcicum* leaf blight of maize." *Plant Dis Rep* 59: 296-300.

Gaj, T, Gersbach, C A and Barbas III, C F (2013). ZFN, TALEN, and CRISPR/Cas-based methods for genome engineering. *Trends in biotechnology*.

Ganal M W, Durstewitz G, Polley A, Bérard A, Buckler E S, Charcosset A, Clarke J D, Graner E-M, et al. (2011) "A large maize (*Zea mays* L.) SNP genotyping array: Development and germplasm genotyping, and genetic mapping to compare with the B73 reference genome." *PLoS ONE* 6 e28334.

Gianasi, L, de Castro, H A and da Silva, H P (1996). "Raças fisiológocas de *Exserohilum turcicum* identificadas em regiões produtoras de milho no Brasil, Safra 93/94." [Physiological races of *Exserohilum turcicum* identified in maize-producing regions of Brazil, Safra 93/94] *Summa Phytopathol.* 22: 214-217.

Griffiths, A J F, Miller, J H, Suzuki, D T, Lewontin, R C and Gelbart, W M (2000) An Introduction to Genetic Analysis, 7th edition, New York: W. H. Freeman; ISBN-10: 0-7167-3520-2

Gupta, P K and Varshney, R (2013) Cereal Genomics II. Springer Science+Business Media Dordrecht, Netherlands; DOI: 10.1007/978-94-007-6401-9_1.

Hanekamp H., Kessel B., Koopmann B., von Thiedemann A.: Turcicum Blattdürre an Mais: Rassenbestimmung and regionales Auftreten von *Exserohilum turcicum* in Europa [*Turcicum* leaf blight in maize: race determination and regional occurrence of *Exserohilum turcicum* in Europe]; 28 Jan. 2013, PG Krankheiten an Getreide, Vortrag; Blattdürre.

Jordan, E G, Perkins, J M, Schall, R A and Pedersen, W L (1983). "Occurrence of race 2 of *Exserohilum turcicum* on corn in the central and eastern United States." *Plant Disease* 67: 1163-1165.

Li, T., Huang, S., Jiang, W. Z., Wright, D., Spalding, M. H., Weeks, D. P., & Yang, B. (2011). TAL nucleases (TALNs): hybrid proteins composed of TAL effectors and FokI DNA-cleavage domain. *Nucleic acids research*, 39(1), 359-372.

Lipps, P E, and Hite, R E (1982). "*Exserohilum turcicum* virulent on corn with the HT resistance gene in Ohio." *Plant Disease* 66: 397-398.

Lipps, P E, Pratt, R A and Hakiza, J J (1997). "Interaction of H T and partial resistance to *Exserohilum turcicum* in maize." *Plant Disease* 81: 277-282.

Maniatis, T, Fritsch, E F, Sambrook, J (1982) Molecular cloning. Cold Spring Harbor Laboratory, Cold Spring Harbor, N.Y.

Manoli A., Sturaro A., Trevisan S., Quaggiotti S., Nonis A. (2012) Evaluation of candidate reference genes for qPCR in maize, *Journal of Plant Physiology*, Volume 169, Issue 8, 15 May 2012, Pages 807-815.

Margulies, M, Egholm, M, Altman, W E, Attiya, S, Bader, J S, Bemben, L A et al. and Volkmer, G A (2005) "Genome sequencing in microfabricated high-density picolitre reactors." *Nature*, 437(7057), 376-380.

Moghaddam, F P and Pataky, J K (1994). "Reactions for isolates from mating of races 1 and 23N of *Exserohilum turcicum.*" *Plant Disease* 78: 767-771.

Min, J, Chunyu, Z, Khalid, H, Nan, L., Quan, S, Qing, M, Suwen, W and Feng, L (2012). "Pyramiding resistance genes to Northern Leaf Blight and Head Smut in maize." *Int. J. Agric. Biol.* 14(3): 430-434.

Odell J T, Nagy F, Chua N-H (1985) Identification of DNA sequences required for activity of the cauliflower mosaic virus 35S promoter. *Nature* 313, 810-812

Pataky, J K, Raid, R N, du Toit, L J and Schueneman, T J (1998). "Disease severity and yield of sweet corn hybrids with resistance to Northern Leaf Blight." *Plant Disease* 82(1): 57-63.

Perkins, J M and Pedersen, W L (1987). "Disease development and yield losses associated with northern leaf blight on corn." *Plant Disease* 71: 940-943.

Pratt, R and Gordon, S (2006). "Breeding for resistance to maize foliar pathogens." *Plant Breed Rev.* 27: 119-173.

Puchta, H and Hohn, B (2010). Breaking news: Plants mutate right on target. *Proceedings of the National Academy of Sciences,* 107(26), 11657-11658.

Raymundo, A D and Hooker, A L (1981a). "Measuring the relationship between northern corn leaf blight and yield losses." *Plant Disease* 65: 325-327.

Raymundo, A D, Hooker, A L and Perkins, J M (1981 b). "Effect of Gene HtN on the Development of Northern Corn Leaf Blight Epidemics." *Plant Disease* 65(4): 327-329.

Risk, J. M., Selter, L. L., Krattinger, S. G., Viccars, L. A., Richardson, T. M., Buesing, G., Herren, G., Lagudah, E. S. and Keller, B. (2012) Functional variability of the Lr34 durable resistance gene in transgenic wheat. *Plant Biotechnology Journal,* 10, 477-487.

Rozen, S and Skaletsky, H J (2000) primer3 on the WWW for general users and for biologist programmers. In: Krawetz S, Misener S (eds) *Bioinformatics Methods and Protocols: Methods in Molecular Biology*. Humana Press, Totowa, N.J., pp 365-386

Rushton, P J, Torres, J T, Parniske, M, Wernert, P, Hahlbrock, K and Somssich, I E (1996) Interaction of elicitor-induced DNA-binding proteins with elicitor response elements in the promoters of parsley PR1 genes. EMBO J. 15(20): 5690-5700.

Sambrook J, Russell D W (2001) Molecular Cloning. A laboratory manual, Cold Spring Harbor Laboratory Press, 3. Aufl. 2001. Sanger, F and Coulson, A R. (1975) *J. molec. Biol.* 94, 414-418.

Silva, G, Poirot, L, Galetto, R, Smith, J, Montoya, G, Duchateau, P, & Pâques, F (2011) Meganucleases and other tools for targeted genome engineering: perspectives and challenges for gene therapy. *Current gene therapy,* 11(1), 11.

Simcox, K D, and Bennetzen, J L (1993). "The use of molecular markers to study *Setospaeria turcica* resistance in maize." *Phytopathology* 83: 1326-1330.

Shimoni, M, Bar-Zur, A, & Reuveni, R (1991). The association of peroxidase activity and resistance of maize to *Exserohilum turcicum. Journal of phytopathology,* 131 (4), 315-321.

Stanković, S, Lević, J, & Ivanović, D (2007). Genetic variability of maize pathogens in Serbia. *Genetika,* 39(2), 227-240.

Thakur, R P, Leonard, K J and Leath, S (1989). "Effects of temperature and light on virulence of *Exserohilum turcicum* on corn." *Phytopathology* 1989, 79: 631-635.

Tzfira, T, Weinthal, D, Marton, I, Zeevi, V, Zuker, A, & Vainstein, A (2012). Genome modifications in plant cells by custom-made restriction enzymes. *Plant biotechnology journal*, 10(4), 373-389.

Ullstrup, A J and Miles, S R (1957). "The effects of some leaf blights on corn grain yield." *Phytopathology* 47:331-336.

Walsh et al. (2008), Poster presentation P192, 50th Maize Genetics Conference in Washington D.C.

Welz, H G (1998). "Genetics and epidemiology of the pathosystem *Zea mays/Setosphaeria turcica*." Habilitationsschrift Institut for Pflanzenzüchtung, Saatgutforschung and Populationsgenetik, Universität Hohenheim.

Welz, H G and Geiger, H H (2000). "Genes for resistance to northern corn leaf blight in diverse maize populations." *Plant Breeding* 119: 1-14.

WO/2000/29592 (Max-Planck-Gesellschaft zur Förderung der Wissenschaften e.V.). Chimeric promoters capable of conferring gene expression in plants upon pathogen infection and uses thereof.

WO/2007/147395 (KWS SAAT AG). Pathogen induzierbarer synthetischer Promotor [Pathogen-inducible synthetid promoter].

WO/2010/079430 (Bonas et al.) Modular DNA-binding domains and methods of use

WO/2011/072246 (Regents of the University of Minnesota) TAL effector-conferred DNA modification.

WO/2011/163590 (Du Pont) Compositions and methods for enhancing resistance to Northern Leaf Blight in maize.

The invention claimed is:

1. A maize plant into the genome of which a chromosome fragment from a donor Pepitilla has been integrated,
   wherein the chromosome fragment comprises an interval of the donor which exhibits at least the donor allele of the marker MA0008 and comprises a polynucleotide which confers resistance to *Helminthosporium turcicum* in the maize plant; and
   wherein the chromosome fragment:
   a) does not comprise an interval of the donor defined by the marker SYN14136 and the marker SYN24931;
   b) does not comprise an interval of the donor defined by the marker PZE-108093748 and the marker MA0005; and
   c) does not comprise an interval of the donor defined by the marker MA0006 and the marker PZE-108107671,
   wherein the polynucleotide which confers resistance to *Helminthosporium turcicum* comprises:
   (a) a nucleotide sequence with the cDNA of SEQ ID NO: 1;
   (b) a nucleotide sequence which is at least 99% identical to the nucleotide sequence with the cDNA of SEQ ID NO: 1; or
   (c) a nucleotide sequence coding for a polypeptide with the amino acid sequence of SEQ ID NO: 2; and wherein the donor allele of the marker MA0008 at position 152045141 as projected to B73 reference genome AGPv02 is a thymine (T).

2. The maize plant as claimed in claim 1, wherein a flowering time for the maize plant and/or a silage yield of the maize plant corresponds to that of a comparative maize plant into the genome of which the chromosome fragment from the donor Pepitilla has not been integrated.

3. A cell, a tissue, or a part of the maize plant as claimed in claim 1, the cell, tissue, or part comprising the chromosome fragment comprising the interval of the donor which exhibits at least the donor allele of the marker MA0008 and comprising the polynucleotide which confers resistance to *Helminthosporium turcicum* in the maize plant.

4. A grain or a seed from the maize plant as claimed in claim 1, the grain or seed comprising the chromosome fragment comprising the interval of the donor which exhibits at least the donor allele of the marker MA0008 and comprising the polynucleotide which confers resistance to *Helminthosporium turcicum* in the maize plant.

5. The maize plant as claimed in claim 1, wherein the chromosome fragment does not comprise an interval of the donor defined by and including the marker SYN14136 and the marker SYN24931, and wherein the markers SYN14136 and SYN24931 are part of the interval.

6. The maize plant as claimed in claim 1, wherein the chromosome fragment does not comprise an interval of the donor defined by and including the marker PZE-108093748 and the marker MA0005, and wherein the markers PZE-108093748 and MA0005 are part of the interval.

7. The maize plant as claimed in claim 1, wherein the chromosome fragment does not comprise an interval of the donor defined by and including the marker MA0006 and the marker PZE-108107671, and wherein the markers MA0006 and PZE-108107671 are part of the interval.

\* \* \* \* \*

SEQUENCE LISTING

```
<160> NUMBER OF SEQ ID NOS: 250

<210> SEQ ID NO 1
<211> LENGTH: 2004
<212> TYPE: DNA
<213> ORGANISM: Zea mays

<400> SEQUENCE: 1
atggctgctc accagcctca cctctccgtc ctcctcctcg tcctcctcgc tgcccatgtc    60
gtctccacct ccgcccatgg cgagcctcct cttccgagcc cttacaacac ctccgcccat   120
ggcgagcctc ctcttccgag cacttacaac gcctccatgt gctcgtcgtt ctggtgtggc   180
ggcgtcgaga tccgctaccc gttctatctt gccaacgcaa tcgccgacta cagcgggagc   240
tactactcct gcggctacac cgacttgagc gtttcctgcg aactcgaggt cgaggggtcg   300
ccgacgacct ggacccctac catccgtctc ggcggcggcg actacaccgt caagaacatc   360
tcctacctct acgaccagca gaccatctca ctggcggaca gagatgtgct cggaggcggc   420
ggctgccccg tcgtccgcca caacgtcagc ttcgacgaga cgtggctgca cctgcacaac   480
gccagcgcct tcgacaacct caccttcttc ttcggatgcc actgggggcc acggaataca   540
ccgcctgaat ttgccgacta caacatcagc tgcgccgggt tcaatactcc aactatcagc   600
ggtggaaggt ccttcgtgtt caagactgga gatcttgacg aacaagagga gcaggagttg   660
gctttacact gcgacgaggt tttctccgtg ccagtgagaa gagatgctct gcaggcgatc   720
gtcagcaact tcagcctcac acgggacggg tacggcgagg tgcttaggca ggggttcgag   780
ttggaatgga atcggacatc ggaggatcag tgtggccggt gcgagggatc gggctccggc   840
ggatggtgcg cctacagcca aagagagaa ttcctgggct gcttgtgcag cggagggaag   900
gtgggcagcc cgttctgcaa accatcgaga tcaaaaagga aagaaggacc tattgttggt   960
gctgttgccg ttgcattcct gtgtctagtc attctcacat gcttcttggc ttgtagacat  1020
ggttcgctgc ccttcaaatc ggagaacaaa ccagggacaa ggattgagtc cttcctacag  1080
aagaacgaga gtatacatcc gaaaagatac acctacgcgg acgtgaaaag aatgacaaaa  1140
tccttcgctg tgaagctagg ccaaggtggg tttggtgctg tatacaaagg cagcctccac  1200
gatggccgac aggtagcagt caagatgctg aaggacaccc aaggtgacgg cgaggaattc  1260
atgaacgagg tggctagcat cagcaggact tctcatgtca acgtcgtgac acttctaggg  1320
ttttgcttgc aagggtcgaa aagagcactg atctacgagt acatgcccaa tggttcgctc  1380
gaaaggtatg ccttcaccgg tgacatgaac agtgagaatt tgctaacctg ggaaaggcta  1440
```

-continued

```
tttgacatag caattggcac ggccagaggg ctcgaatacc tacaccgggg atgcaacact    1500
cggatcgtgc attttgacat caagccacac aacatcctgt tagaccagga tttctgtcct    1560
aagatctctg actttggact ggccaagcta tgtctgaaca agagagcgc tatctccatt     1620 gctggcgcaa agggacgat agggtatatc gccccggagg tctactcaaa gcaatttgga    1680
ataataagca gcaagtctga tgtctatagc tatgggatga tggtccttga gatggttgga    1740
gcaagggaca ggaatacaag cgcagatagt gaccatagca gccaatattt ccctcagtgg    1800
ctttatgaac atttggacga ctattgtgtt ggtgcttccg agattaatgg tgagaccaca    1860
gagctcgtga ggaagatgat agttgtaggt ctgtggtgca tacaagtgat tccgactgat    1920
cgaccaacaa tgacgagagt cgtcgagatg ttggaaggga gcacaagtaa tctagagttg    1980
ccacccagag ttctcttgag ctga                                         2004
```

<210> SEQ ID NO 2
<211> LENGTH: 667
<212> TYPE: PRT
<213> ORGANISM: Zea mays

<400> SEQUENCE: 2

```
Met Ala Ala His Gln Pro His Leu Ser Val Leu Leu Val Leu Leu
1               5                   10                  15

Ala Ala His Val Val Ser Thr Ser Ala His Gly Glu Pro Pro Leu Pro
            20                  25                  30

Ser Pro Tyr Asn Thr Ser Ala His Gly Glu Pro Pro Leu Pro Ser Thr
        35                  40                  45

Tyr Asn Ala Ser Met Cys Ser Ser Phe Trp Cys Gly Gly Val Glu Ile
    50                  55                  60

Arg Tyr Pro Phe Tyr Leu Ala Asn Ala Ile Ala Asp Tyr Ser Gly Ser
65                  70                  75                  80

Tyr Tyr Ser Cys Gly Tyr Thr Asp Leu Ser Val Ser Cys Glu Leu Glu
                85                  90                  95

Val Glu Gly Ser Pro Thr Thr Trp Thr Pro Thr Ile Arg Leu Gly Gly
            100                 105                 110

Gly Asp Tyr Thr Val Lys Asn Ile Ser Tyr Leu Tyr Asp Gln Gln Thr
        115                 120                 125

Ile Ser Leu Ala Asp Arg Asp Val Leu Gly Gly Gly Cys Pro Val
    130                 135                 140

Val Arg His Asn Val Ser Phe Asp Glu Thr Trp Leu His Leu His Asn
145                 150                 155                 160

Ala Ser Ala Phe Asp Asn Leu Thr Phe Phe Gly Cys His Trp Gly
                165                 170                 175

Pro Arg Asn Thr Pro Pro Glu Phe Ala Asp Tyr Asn Ile Ser Cys Ala
            180                 185                 190

Gly Phe Asn Thr Pro Thr Ile Ser Gly Gly Arg Ser Phe Val Phe Lys
        195                 200                 205

Thr Gly Asp Leu Asp Glu Gln Glu Gln Glu Leu Ala Leu His Cys
    210                 215                 220

Asp Glu Val Phe Ser Val Pro Val Arg Arg Asp Ala Leu Gln Ala Ile
225                 230                 235                 240

Val Ser Asn Phe Ser Leu Thr Arg Asp Gly Tyr Gly Glu Val Leu Arg
                245                 250                 255

Gln Gly Phe Glu Leu Glu Trp Asn Arg Thr Ser Glu Asp Gln Cys Gly
            260                 265                 270
```

```
Arg Cys Glu Gly Ser Gly Ser Gly Gly Trp Cys Ala Tyr Ser Gln Lys
            275                 280                 285

Arg Glu Phe Leu Gly Cys Leu Cys Ser Gly Gly Lys Val Gly Ser Pro
            290                 295                 300

Phe Cys Lys Pro Ser Arg Ser Lys Arg Lys Glu Gly Pro Ile Val Gly
305                 310                 315                 320

Ala Val Ala Val Ala Phe Leu Cys Leu Val Ile Leu Thr Cys Phe Leu
                325                 330                 335

Ala Cys Arg His Gly Ser Leu Pro Phe Lys Ser Glu Asn Lys Pro Gly
            340                 345                 350

Thr Arg Ile Glu Ser Phe Leu Gln Lys Asn Glu Ser Ile His Pro Lys
            355                 360                 365

Arg Tyr Thr Tyr Ala Asp Val Lys Arg Met Thr Lys Ser Phe Ala Val
            370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
            420                 425                 430

Val Asn Val Val Thr Leu Leu Gly Phe Cys Leu Gln Gly Ser Lys Arg
            435                 440                 445

Ala Leu Ile Tyr Glu Tyr Met Pro Asn Gly Ser Leu Glu Arg Tyr Ala
            450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
            515                 520                 525

Lys Leu Cys Leu Asn Lys Glu Ser Ala Ile Ser Ile Ala Gly Ala Arg
            530                 535                 540

Gly Thr Ile Gly Tyr Ile Ala Pro Glu Val Tyr Ser Lys Gln Phe Gly
545                 550                 555                 560

Ile Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
            595                 600                 605

Cys Val Gly Ala Ser Glu Ile Asn Gly Glu Thr Thr Glu Leu Val Arg
610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665

<210> SEQ ID NO 3
<211> LENGTH: 2133
<212> TYPE: DNA
```

<213> ORGANISM: Zea mays

<400> SEQUENCE: 3

```
atggctgctc acctaccacg cctccccgtc ctcctcctcg tcctcctcgc tgcccatgtc      60
gtctccacct ccgcccatgg cgagcctcct cttccgagca cttacaacac ctccgcccat     120
ggcgagcctc ttcttccgag cacttacaac gcctccatgt gctcggaatc gttctggtgt     180
ggcggcgtcg agatccgcta cccgttcaat cttgccaacg caaccgccga ctacagcggg     240
aactactact cctgcggcta caccgacttg agcgtttcct gcgaactcga ggtcgaaggg     300
tcgccgacga cctggacccc taccatccgt ctcggcggcg acatctacac cgtcaagaac     360
atctcctacg actatcatac catctcactg gcggacaacg atgtgctcgg aggcggcgag     420
tgccccgtcg tccgccacaa cgtcagcttc aacgagacgt ggctgcacaa cgccagcgcc     480
ttcgacaacc tcaccttctt cttcggatgc cactgggggc cacggaatac accgcctgaa     540
tttgccgact acaacatcag ctgcgccggg ttcaatcctc aactatcag cggtggagac      600
tccttcgtgt tcaagcctga atatcttgac gaacaagagg agcaggagtt ggcttcacac     660
tgcgacgagg ttttctccgt gccagtcaga agcgatgctc tgcgggcgac cttcagcctc     720
acagggtacg ggtacggcga gctgcttagg caggggttcg ggttggaatg gaatcggaca     780
tcggaggatc agtgtggcca gtgcgaggga tcgggctccg gcggatggtg cgcctacagc     840
cagaagagag aattcctggg ctgcttgtgc agcggaggga aggtgggcaa cccgttctgc     900
aaaccatcga agtcaacaag gaaaccaaga attcttgctg gtgccctggg tggtggtgct     960
gctgcgctgc ttgttggtgc tgccatattt ttgttcgtca tcatgcgcaa gaggaagcag    1020
aagaagaaag tgaccaactc gtcttcgaag ctcctcaagt acagcggctc tggtgggacc    1080
ccgcgttcgc gggttggtga catggagtcc ggcagcatcg aggacccgcc aacgcaccac    1140
ttcgcctacg aggagctcga ggaggcgacc aaccgcttcg acgaaagcag agaactcggc    1200
gatggcgggct tcggcaccgt ctacaaaggg tacctcaggg acgggcgcgt ggtggcggtg    1260
aagcggctgt acaacaacgg gtaccggcgc gtggagcagt tccagaacga ggcggccatc    1320
ctgtcggggc tgcgccaccc aaacctcgtc atgttctacg gctgcacgtc cagccacagc    1380
cgcgagctcc tgctggtgta cgagttcgtg gccaacggca cggtcgccga ccacctgcac    1440
gggcagcggg ccccgagcg cgccctctcg tggccgctcc gctcagcgt cgccgtggag     1500
tccgccgcgg cgctcaccta cctgcacgcc atcgagccgc cgtcgtgca ccgcgacgtc     1560
aagaccacca acatcctcct ggacgccgac taccacgtca aggtcgccga cttcggcctc    1620
tcccgcctct cccccctcga cgtcacgcac gtctccaccg ctccgcaggg cacgccaggg    1680
tatgttgatc cagagtacca ccagtgctac cagctgacgg acaagagcga cgtgtacagc    1740
ttcggggtgg tcctggtgga gctcatctcg tccaagccgg ccgtcgacat caccccggcac    1800
cgcagcgaga tcaacctggc cagcatggcc atcagcaaga tccagaagtg ccagctggag    1860
gagctcgtcg acctcggcct gggctacgac accgacccgg ccaccaggaa gatgatgacg    1920
atggtcgcgg agctggcctt ccgctgcctg cagcagaacg gcgagatgcg cccgccgatc    1980
aaggaggtgc tcgaggtgct caggaacatc cagggcgagt gtctgacgtc ggggaaggat    2040
ggggacaaga gcaaggacgg gccctttctct cccaccacgg ttcacgctcc gtgggacagc    2100
aggtccacga cgcccaacac cagcagggac tag                                2133
```

<210> SEQ ID NO 4
<211> LENGTH: 710

<212> TYPE: PRT
<213> ORGANISM: Zea mays

<400> SEQUENCE: 4

```
Met Ala Ala His Leu Pro Arg Leu Pro Val Leu Leu Val Leu Leu
1               5                   10                  15

Ala Ala His Val Val Ser Thr Ser Ala His Gly Glu Pro Leu Pro
            20                  25                  30

Ser Thr Tyr Asn Thr Ser Ala His Gly Glu Pro Leu Leu Pro Ser Thr
        35                  40                  45

Tyr Asn Ala Ser Met Cys Ser Glu Ser Phe Trp Cys Gly Gly Val Glu
50                  55                  60

Ile Arg Tyr Pro Phe Asn Leu Ala Asn Ala Thr Ala Asp Tyr Ser Gly
65                  70                  75                  80

Asn Tyr Tyr Ser Cys Gly Tyr Thr Asp Leu Ser Val Ser Cys Glu Leu
                85                  90                  95

Glu Val Glu Gly Ser Pro Thr Thr Trp Thr Pro Thr Ile Arg Leu Gly
            100                 105                 110

Gly Asp Ile Tyr Thr Val Lys Asn Ile Ser Tyr Asp Tyr His Thr Ile
        115                 120                 125

Ser Leu Ala Asp Asn Asp Val Leu Gly Gly Glu Cys Pro Val Val
130                 135                 140

Arg His Asn Val Ser Phe Asn Glu Thr Trp Leu His Asn Ala Ser Ala
145                 150                 155                 160

Phe Asp Asn Leu Thr Phe Phe Gly Cys His Trp Gly Pro Arg Asn
                165                 170                 175

Thr Pro Pro Glu Phe Ala Asp Tyr Asn Ile Ser Cys Ala Gly Phe Asn
            180                 185                 190

Pro Pro Thr Ile Ser Gly Gly Asp Ser Phe Val Phe Lys Pro Glu Tyr
        195                 200                 205

Leu Asp Glu Gln Glu Gln Glu Leu Ala Ser His Cys Asp Glu Val
210                 215                 220

Phe Ser Val Pro Val Arg Ser Asp Ala Leu Arg Ala Thr Phe Ser Leu
225                 230                 235                 240

Thr Gly Tyr Gly Tyr Gly Leu Leu Arg Gln Gly Phe Gly Leu Glu
                245                 250                 255

Trp Asn Arg Thr Ser Glu Asp Gln Cys Gly Gln Cys Glu Gly Ser Gly
            260                 265                 270

Ser Gly Gly Trp Cys Ala Tyr Ser Gln Lys Arg Glu Phe Leu Gly Cys
        275                 280                 285

Leu Cys Ser Gly Gly Lys Val Gly Asn Pro Phe Cys Lys Pro Ser Lys
290                 295                 300

Ser Thr Arg Lys Pro Arg Ile Leu Ala Gly Leu Gly Gly Gly Ala
305                 310                 315                 320

Ala Ala Leu Leu Val Gly Ala Ala Ile Phe Leu Phe Val Ile Met Arg
                325                 330                 335

Lys Arg Lys Gln Lys Lys Val Thr Asn Ser Ser Lys Leu Leu
            340                 345                 350

Lys Tyr Ser Gly Ser Gly Thr Pro Arg Ser Arg Val Gly Asp Met
        355                 360                 365

Glu Ser Gly Ser Ile Glu Asp Pro Pro Thr His His Phe Ala Tyr Glu
370                 375                 380

Glu Leu Glu Glu Ala Thr Asn Arg Phe Asp Ser Arg Glu Leu Gly
385                 390                 395                 400
```

Asp Gly Gly Phe Gly Thr Val Tyr Lys Gly Tyr Leu Arg Asp Gly Arg
            405                 410                 415

Val Val Ala Val Lys Arg Leu Tyr Asn Asn Gly Tyr Arg Arg Val Glu
            420                 425                 430

Gln Phe Gln Asn Glu Ala Ala Ile Leu Ser Gly Leu Arg His Pro Asn
            435                 440                 445

Leu Val Met Phe Tyr Gly Cys Thr Ser Ser His Ser Arg Glu Leu Leu
            450                 455                 460

Leu Val Tyr Glu Phe Val Ala Asn Gly Thr Val Ala Asp His Leu His
465                 470                 475                 480

Gly Gln Arg Ala Pro Glu Arg Ala Leu Ser Trp Pro Leu Arg Leu Ser
            485                 490                 495

Val Ala Val Glu Ser Ala Ala Leu Thr Tyr Leu His Ala Ile Glu
            500                 505                 510

Pro Pro Val Val His Arg Asp Val Lys Thr Thr Asn Ile Leu Leu Asp
            515                 520                 525

Ala Asp Tyr His Val Lys Val Ala Asp Phe Gly Leu Ser Arg Leu Phe
530                 535                 540

Pro Leu Asp Val Thr His Val Ser Thr Ala Pro Gln Gly Thr Pro Gly
545                 550                 555                 560

Tyr Val Asp Pro Glu Tyr His Gln Cys Tyr Gln Leu Thr Asp Lys Ser
            565                 570                 575

Asp Val Tyr Ser Phe Gly Val Val Leu Val Glu Leu Ile Ser Ser Lys
            580                 585                 590

Pro Ala Val Asp Ile Thr Arg His Arg Ser Glu Ile Asn Leu Ala Ser
            595                 600                 605

Met Ala Ile Ser Lys Ile Gln Lys Cys Gln Leu Glu Glu Leu Val Asp
            610                 615                 620

Leu Gly Leu Gly Tyr Asp Thr Asp Pro Ala Thr Arg Lys Met Met Thr
625                 630                 635                 640

Met Val Ala Glu Leu Ala Phe Arg Cys Leu Gln Gln Asn Gly Glu Met
            645                 650                 655

Arg Pro Pro Ile Lys Glu Val Leu Glu Val Leu Arg Asn Ile Gln Gly
            660                 665                 670

Glu Cys Leu Thr Ser Gly Lys Asp Gly Asp Lys Ser Lys Asp Gly Pro
            675                 680                 685

Phe Ser Pro Thr Thr Val His Ala Pro Trp Asp Ser Arg Ser Thr Thr
            690                 695                 700

Pro Asn Thr Ser Arg Asp
705                 710

<210> SEQ ID NO 5
<211> LENGTH: 879
<212> TYPE: DNA
<213> ORGANISM: Zea mays

<400> SEQUENCE: 5
atggctcctc tgctcctgct cctgctcctc ttccccgtcc agttccagct cctgctcctc      60
ctagccgtag ccgacgctgt ccccggtctc tgcgccagag ccacatgcgc cggccatgtc     120
atccagtacc cgttctggct caactcctcg gcgcccgact gcggccgccg ccacgggatc     180
ggccttgtct gcgagggcaa ctcgacgctg accctcccct acatgtccca gatacgtca     240 gtgtccagca tcgactacaa gacgcgtacc gtgctggtct cggacgccga catcggcgac     300

```
gagtacgacg cggccggctg cccgcgcgtc cgcgtgaacc tcaccatcga caccgcctgg    360
ctgcggcccg cggcctccga cgccaacatc accttcctct acgactgcaa gaagagcatc    420
accctgccct ccgccgtgga actgagtggg tgccattgcc accagcagca gcagcagcag    480
caacaggatt attgccgtag gtcgtacgtg ctgccggacg gcgggatcac gggcgccgag    540
gcgcaccagt acgggtgcga ggacgtggtg gtggcgccgg tgctggacgc gcacaggagg    600
gagatcctgg gcgcgcctcc ggcgaacgga tccctccgcc gggtgctgca gggcgggttc    660
gagctgaact acgacaccca ctctgagctg tgcgaccggt gcgaggcctc cggcgggtgg    720
tgcggctacc ggcgcggcga ggcgcccgcc accggcgccg gcggcgggct gacgttcgcc    780
tgcttctgcg acggcggccc gacgacgacg ggcctgtgcg gtgccggtac gtacctcctc    840
ttcattcccc cagcgttaca atttattata tgtttgtaa                          879
```

<210> SEQ ID NO 6
<211> LENGTH: 292
<212> TYPE: PRT
<213> ORGANISM: Zea mays

<400> SEQUENCE: 6

```
Met Ala Pro Leu Leu Leu Leu Leu Leu Phe Pro Val Gln Phe Gln
1               5                   10                  15

Leu Leu Leu Leu Leu Ala Val Ala Asp Ala Val Pro Gly Leu Cys Ala
                20                  25                  30

Arg Ala Thr Cys Ala Gly His Val Ile Gln Tyr Pro Phe Trp Leu Asn
            35                  40                  45

Ser Ser Ala Pro Asp Cys Gly Arg His Gly Ile Gly Leu Val Cys
    50                  55                  60

Glu Gly Asn Ser Thr Leu Thr Leu Pro Tyr Met Ser His Arg Tyr Val
65                  70                  75                  80

Val Ser Ser Ile Asp Tyr Lys Thr Arg Thr Val Leu Val Ser Asp Ala
                85                  90                  95

Asp Ile Gly Asp Glu Tyr Asp Ala Ala Gly Cys Pro Arg Val Arg Val
            100                 105                 110

Asn Leu Thr Ile Asp Thr Ala Trp Leu Arg Pro Ala Ala Ser Asp Ala
        115                 120                 125

Asn Ile Thr Phe Leu Tyr Asp Cys Lys Lys Ser Ile Thr Leu Pro Ser
    130                 135                 140

Ala Val Glu Leu Ser Gly Cys His Cys His Gln Gln Gln Gln Gln
145                 150                 155                 160

Gln Gln Asp Tyr Cys Arg Arg Ser Tyr Val Leu Pro Asp Gly Gly Ile
                165                 170                 175

Thr Gly Ala Glu Ala His Gln Tyr Gly Cys Glu Asp Val Val Val Ala
            180                 185                 190

Pro Val Leu Asp Ala His Arg Arg Glu Ile Leu Gly Ala Pro Pro Ala
        195                 200                 205

Asn Gly Ser Leu Arg Arg Val Leu Gln Gly Gly Phe Glu Leu Asn Tyr
    210                 215                 220

Asp Thr His Ser Glu Leu Cys Asp Arg Cys Glu Ala Ser Gly Gly Trp
225                 230                 235                 240

Cys Gly Tyr Arg Arg Gly Glu Ala Pro Ala Thr Gly Ala Gly Gly
                245                 250                 255

Leu Thr Phe Ala Cys Phe Cys Asp Gly Gly Pro Thr Thr Thr Gly Leu
            260                 265                 270
```

```
Cys Gly Ala Gly Thr Tyr Leu Leu Phe Ile Pro Pro Ala Leu Gln Phe
            275                 280                 285

Ile Ile Cys Leu
    290

<210> SEQ ID NO 7
<211> LENGTH: 588
<212> TYPE: DNA
<213> ORGANISM: Zea mays

<400> SEQUENCE: 7
atggggtgca cgacctccca cgacgccgtc gccgctgctg tcacctcctc cagttcccgg    60
ccccgtgcgc gccgctcgtc cgcgtccgac ccctcaccac ggcgcggaga ccccgccgcg   120
ctgtgccgcg agcgcgtggc gctcatccac gccgcgaccg accgccggta cgcgctcgcc   180
accgcgcacg ctgcctactt ccgctcgctc gccgccgtcg gtgacgcgct gcggcgcttc   240
gtggcgtccg cgctcgcgcc cgccacgcct gggtcctcgc tggtgctcac gctcccgcct   300
tcccccgcca gctggtcgc tgccgcgtcc gccagcctcc cgacgtggcc gttgtccacc   360
gtctcgtcgc tctcgcactc cctcgcagag aagcggcgga tctttaggga ggcggcgttg   420
aagggaagcg cgcgagagag gacacagtca cggactcagg ccaccgttgc tcacagctgc   480
attagaatcc gatttcgggt ccacgctcac acgtgtcaac gccggatacg ggatgctaac   540
gtgaagtgcg gacgaggctt caaaagggggt gaggttttaa taacttag                588

<210> SEQ ID NO 8
<211> LENGTH: 195
<212> TYPE: PRT
<213> ORGANISM: Zea mays

<400> SEQUENCE: 8

Met Gly Cys Thr Thr Ser His Asp Ala Val Ala Ala Val Thr Ser
  1               5                  10                  15

Ser Ser Ser Arg Pro Arg Ala Arg Arg Ser Ser Ala Ser Asp Pro Ser
                 20                  25                  30

Pro Arg Arg Gly Asp Pro Ala Ala Leu Cys Arg Glu Arg Val Ala Leu
             35                  40                  45

Ile His Ala Ala Thr Asp Arg Arg Tyr Ala Leu Ala Thr Ala His Ala
         50                  55                  60

Ala Tyr Phe Arg Ser Leu Ala Ala Val Gly Asp Ala Leu Arg Arg Phe
 65                  70                  75                  80

Val Ala Ser Ala Leu Ala Pro Ala Thr Pro Gly Ser Ser Leu Val Leu
                 85                  90                  95

Thr Leu Pro Pro Ser Pro Ala Lys Leu Val Ala Ala Ser Ala Ser
                100                 105                 110

Leu Pro Thr Trp Pro Leu Ser Thr Val Ser Ser Leu Ser His Ser Leu
            115                 120                 125

Ala Glu Lys Arg Arg Ile Phe Arg Glu Ala Ala Leu Lys Gly Ser Ala
        130                 135                 140

Arg Glu Arg Thr Gln Ser Arg Thr Gln Ala Thr Val Ala His Ser Cys
145                 150                 155                 160

Ile Arg Ile Arg Phe Arg Val His Ala His Thr Cys Gln Arg Arg Ile
                165                 170                 175

Arg Asp Ala Asn Val Lys Cys Gly Arg Gly Phe Lys Arg Gly Glu Val
            180                 185                 190

Leu Ile Thr
```

195

<210> SEQ ID NO 9
<211> LENGTH: 3699
<212> TYPE: DNA
<213> ORGANISM: Zea mays

<400> SEQUENCE: 9

| | | | | | | |
|---|---|---|---|---|---|---|
| atggcgacgc | cgacgcccat | gcctggaggc | gagggacgc | tcgcagcggt | gatgccgcgg | 60 |
| tccccgtctc | cgacgccggc | ggaggcgggg | acctcggcga | ccgagacgcc | cgtgctgata | 120 |
| ttcctttact | tcacaaggc | gatccgcgcg | gagctcgagg | cgctgcacgg | cgccgccgtg | 180 |
| ctcctggcca | ccgagcgcac | cggcgatgta | gagatgctcg | ccaagcgctg | ccgcttcttc | 240 |
| ttcaacattt | acaaacacca | ctgcgacgcc | gaggatgcgg | tcattttcc | agcactcgat | 300 |
| atccgagtaa | agaatgttgc | agggacctat | tccttagagc | ataaaggaga | aagcgatctt | 360 |
| tttagccagt | tatttgatct | cctgcaattg | gacatacata | atgatgatgg | tcttcgtagg | 420 |
| gagcttgcgt | catgcacagg | cgcgatacag | acatgtctca | gccaacatat | gtccaaggag | 480 |
| gaagaacagg | tctttccatt | gcttacaaag | aaattttcgt | gtgaagaaca | agctgattta | 540 |
| gtgtggcaat | tcctatgcaa | cattcctgtc | aatatggtgg | cagagttcct | tccatggctt | 600 |
| tcaacttctg | tcacatctga | tgagcaccaa | gatatccgta | actgcttatg | caaagtagtt | 660 |
| cctgatgaga | aacttctcca | acaggttgta | ttcacatgga | tggaagggaa | agcaacaaga | 720 |
| gaagtggcag | agagcattgc | tgctggtatt | tcagcaagaa | atcatagtgt | tgaggatgtc | 780 |
| ccagaccaag | ggaagattca | tatttgttta | catcacaatt | ctaaacttgg | gagtaaaaac | 840 |
| tgtggagaat | ctaatggtcc | tcaggctgac | aagcatccta | tagatgatat | tttatactgg | 900 |
| cacaatgcta | ttcgtatgga | gttacgtgat | ataaagagg | agacaagaag | ggtgcagcaa | 960 |
| tctggggatt | tttctgatat | atcagccttc | aatgagaggc | ttcagttcat | tgcagatgta | 1020 |
| tgcatctacc | acagtatcgc | tgaggatcag | gttgttttc | ctgcagtcga | tagtgagctg | 1080 |
| tcctttgtgc | aggagcatgc | tgaagaagaa | tgcaggttta | acaattttag | gtgtttaatt | 1140 |
| cagcaaatcc | aaatagcagg | agccgaatca | actgcattgg | acttctactc | aaaactgtgt | 1200 |
| tcacatgctg | ataaaatatt | ggaggcaatc | gaaaaacact | tctgcaatga | agaaaccaag | 1260 |
| gtgcttcctc | aagctaggat | gctcttctct | cttgagaagc | aaaggggaact | ttcatacaaa | 1320 |
| agtttgtgtg | ttatgccatt | gaaattattg | gaacgtgttt | tgccgtggtt | ggtgtcgaag | 1380 |
| ctgagtgatg | ttcaggcaac | ttcatttctt | cagaatatac | gcttggcagc | atcaccatct | 1440 |
| gaaactgcac | tggtcactct | tatctctggt | tgggcatgca | aaggccggga | taaatccaaa | 1500 |
| gatggagaat | atttatgctt | aacatcaggt | gcggcgagat | gtctatcaga | tgatgtagat | 1560 |
| gatctgggaa | aatgccgatc | attctgtcca | tgtgcttcac | ccaacagctc | agatctttct | 1620 |
| ctgcagctac | atactgagaa | tgattctagg | ccaggcaagc | gaggaaaaga | tgcagtatct | 1680 |
| ttttctcata | ctaatggaat | ctactgctct | caaactgctg | acattgaagc | aattccatgt | 1740 |
| agcaaaaaac | catgttgtat | tcctggtttg | agagtagaga | gtagcaatct | tggtattggt | 1800 |
| tccttggctt | ctgcaaagtc | ttttcactct | ttatcataca | attcaactgc | tccttcacta | 1860 |
| tattcgagcc | tcttttcatg | ggagacagat | acatcattgt | cttgttcgga | cagcatttca | 1920 |
| aggccaatcg | atacaatatt | caaatttcat | aaggcaattc | gcaaggattt | agaatactta | 1980 |
| gatgttgaat | ctggcaagct | cattgatggc | aacgagtcct | gccttcgcca | attcattgga | 2040 |
| aggttccgtt | tgttatgggg | tctttacagg | gctcacagca | atgctgagga | tgaaattgtg | 2100 |

```
tttccagcat tggaatccag agaaacatta cacaatgtga gccattcata tactcttgac    2160
cacaagcagg aagaacagtt gtttgaagat atctcaaatg ttctctttca actttcacaa    2220
ctacatgata gccagggcca tgcccagact gaagttaatg aagtaaagaa aagctgtttc    2280
cattcatcta atgatgtcga ttttgctaga agtataatga aacttgccac aaaacttcag    2340
ggcatgtgca agtctatccg ggtcgccttg actaatcatg tccatagaga gaacttgaa     2400 ttatggccgt tgtttgataa acattttcct gtggaggagc aagataaact tgtaggtcgt    2460
ataattggtt caacaggtgc tgaggttctc caatctatgt taccctgggt tacatcagtt    2520
ctcactcaag aggagcagaa caaaatgctt gatatgtgga agcaagctac aaaaaataca    2580
atgtttgggg aatggctaaa cgagtggtgg aagggagctg aacagcatc tgattcttca     2640 gcagaggcgt cctctgctcc agaagatagt catttacaag ataagcttga acaaaatgac    2700
cagatgttca agcctggctg aaggacata tttcgaatga atcagagtga acttgaggct     2760
gaggtgcgaa aggtttcacg agattctaca cttgacccaa gcggaaggc gtatctaatt     2820 caaaatctca tgacaagccg ctggatagct gcacagcaga agttaccaga accaaattct    2880
gaagaatgta atcacgatgc cagtatacct ggatgtgcac cttcataccg agaccaggag    2940
aaacaaattt atggttgtga acactacaaa cggaactgca aacttgttgc tgcatgctgc    3000
aacaagctct tcacatgcag gttctgccat gataaagtta gtgaccatac gatggaaagg    3060
aaagcaacac aggagatgat gtgcatggta tgcctaaaga ttcaacctgt tggttcgttc    3120
tgccaaaccc catcttgcaa cagactatcg atggcaaagt actactgtaa catctgtaaa    3180
ttttttgatg atgaaaggac tgtgtaccac tgtccgtttt gtaatttgtg tcgtcttggg    3240
aaaggtcttg gtgttgattt cttccattgc atgaaatgca actgctgcct tggaatgaaa    3300
ttaactgagc acaaatgtcg ggaaaaaggg ctagagacaa attgtccaat atgctgtgac    3360 ttcctatttta catcaagtgc cgcagtcaga gccctccctt gtggccactt catgcattca    3420
gcttgctttc aggcatacac ttgtagtcac tacacttgcc ctatctgctg caaatccttg    3480
ggagatatgg cggtttattt tggcatgctt gatgccttgt tggcggctga agagcttccg    3540
gaggaatacc gtgatcggtg tcaggatata ctttgcaatg actgtgagag gaaaggtaga    3600
tgtcgatttc attggttata ccacaaatgc ggctcctgtg ggtcgtacaa cacccgagtt    3660
atcaagactg ccacagcaga ttgctctaca ccaaactag                          3699
```

<210> SEQ ID NO 10
<211> LENGTH: 1232
<212> TYPE: PRT
<213> ORGANISM: Zea mays

<400> SEQUENCE: 10

```
Met Ala Thr Pro Thr Pro Met Pro Gly Gly Glu Gly Thr Leu Ala Ala
1               5                   10                  15

Val Met Pro Arg Ser Pro Ser Pro Thr Pro Ala Glu Ala Gly Thr Ser
            20                  25                  30

Ala Thr Glu Thr Pro Val Leu Ile Phe Leu Tyr Phe His Lys Ala Ile
        35                  40                  45

Arg Ala Glu Leu Glu Ala Leu His Gly Ala Ala Val Leu Leu Ala Thr
    50                  55                  60

Glu Arg Thr Gly Asp Val Glu Met Leu Ala Lys Arg Cys Arg Phe Phe
65                  70                  75                  80

Phe Asn Ile Tyr Lys His His Cys Asp Ala Glu Asp Ala Val Ile Phe
```

```
                        85                  90                  95
Pro Ala Leu Asp Ile Arg Val Lys Asn Val Ala Gly Thr Tyr Ser Leu
                100                 105                 110

Glu His Lys Gly Glu Ser Asp Leu Phe Ser Gln Leu Phe Asp Leu Leu
                115                 120                 125

Gln Leu Asp Ile His Asn Asp Gly Leu Arg Arg Glu Leu Ala Ser
    130                 135                 140

Cys Thr Gly Ala Ile Gln Thr Cys Leu Ser Gln His Met Ser Lys Glu
145                 150                 155                 160

Glu Glu Gln Val Phe Pro Leu Leu Thr Lys Lys Phe Ser Cys Glu Glu
                165                 170                 175

Gln Ala Asp Leu Val Trp Gln Phe Leu Cys Asn Ile Pro Val Asn Met
                180                 185                 190

Val Ala Glu Phe Leu Pro Trp Leu Ser Thr Ser Val Thr Ser Asp Glu
                195                 200                 205

His Gln Asp Ile Arg Asn Cys Leu Cys Lys Val Pro Asp Glu Lys
    210                 215                 220

Leu Leu Gln Gln Val Val Phe Thr Trp Met Glu Gly Lys Ala Thr Arg
225                 230                 235                 240

Glu Val Ala Glu Ser Ile Ala Ala Gly Ile Ser Ala Arg Asn His Ser
                245                 250                 255

Val Glu Asp Val Pro Asp Gln Gly Lys Ile His Ile Cys Leu His His
                260                 265                 270

Asn Ser Lys Leu Gly Ser Lys Asn Cys Gly Glu Ser Asn Gly Pro Gln
    275                 280                 285

Ala Asp Lys His Pro Ile Asp Asp Ile Leu Tyr Trp His Asn Ala Ile
290                 295                 300

Arg Met Glu Leu Arg Asp Ile Lys Glu Glu Thr Arg Arg Val Gln Gln
305                 310                 315                 320

Ser Gly Asp Phe Ser Asp Ile Ser Ala Phe Asn Glu Arg Leu Gln Phe
                325                 330                 335

Ile Ala Asp Val Cys Ile Tyr His Ser Ile Ala Glu Asp Gln Val Val
                340                 345                 350

Phe Pro Ala Val Asp Ser Glu Leu Ser Phe Val Gln Glu His Ala Glu
                355                 360                 365

Glu Glu Cys Arg Phe Asn Asn Phe Arg Cys Leu Ile Gln Gln Ile Gln
                370                 375                 380

Ile Ala Gly Ala Glu Ser Thr Ala Leu Asp Phe Tyr Ser Lys Leu Cys
385                 390                 395                 400

Ser His Ala Asp Lys Ile Leu Glu Ala Ile Glu Lys His Phe Cys Asn
                405                 410                 415

Glu Glu Thr Lys Val Leu Pro Gln Ala Arg Met Leu Phe Ser Leu Glu
                420                 425                 430

Lys Gln Arg Glu Leu Ser Tyr Lys Ser Leu Cys Val Met Pro Leu Lys
                435                 440                 445

Leu Leu Glu Arg Val Leu Pro Trp Leu Val Ser Lys Leu Ser Asp Val
                450                 455                 460

Gln Ala Thr Ser Phe Leu Gln Asn Ile Arg Leu Ala Ala Ser Pro Ser
465                 470                 475                 480

Glu Thr Ala Leu Val Thr Leu Ile Ser Gly Trp Ala Cys Lys Gly Arg
                485                 490                 495

Asp Lys Ser Lys Asp Gly Glu Tyr Leu Cys Leu Thr Ser Gly Ala Ala
                500                 505                 510
```

```
Arg Cys Leu Ser Asp Asp Val Asp Asp Leu Gly Lys Cys Arg Ser Phe
        515                 520                 525

Cys Pro Cys Ala Ser Pro Asn Ser Ser Asp Leu Ser Leu Gln Leu His
        530                 535                 540

Thr Glu Asn Asp Ser Arg Pro Gly Lys Arg Gly Lys Asp Ala Val Ser
545                 550                 555                 560

Phe Ser His Thr Asn Gly Ile Tyr Cys Ser Gln Thr Ala Asp Ile Glu
                565                 570                 575

Ala Ile Pro Cys Ser Lys Lys Pro Cys Cys Ile Pro Gly Leu Arg Val
            580                 585                 590

Glu Ser Ser Asn Leu Gly Ile Gly Ser Leu Ala Ser Ala Lys Ser Phe
        595                 600                 605

His Ser Leu Ser Tyr Asn Ser Thr Ala Pro Ser Leu Tyr Ser Ser Leu
    610                 615                 620

Phe Ser Trp Glu Thr Asp Thr Ser Leu Ser Cys Ser Asp Ser Ile Ser
625                 630                 635                 640

Arg Pro Ile Asp Thr Ile Phe Lys Phe His Lys Ala Ile Arg Lys Asp
                645                 650                 655

Leu Glu Tyr Leu Asp Val Glu Ser Gly Lys Leu Ile Asp Gly Asn Glu
            660                 665                 670

Ser Cys Leu Arg Gln Phe Ile Gly Arg Phe Arg Leu Leu Trp Gly Leu
        675                 680                 685

Tyr Arg Ala His Ser Asn Ala Glu Asp Glu Ile Val Phe Pro Ala Leu
    690                 695                 700

Glu Ser Arg Glu Thr Leu His Asn Val Ser His Ser Tyr Thr Leu Asp
705                 710                 715                 720

His Lys Gln Glu Glu Gln Leu Phe Glu Asp Ile Ser Asn Val Leu Phe
                725                 730                 735

Gln Leu Ser Gln Leu His Asp Ser Gln Gly His Ala Gln Thr Glu Val
            740                 745                 750

Asn Glu Val Lys Lys Ser Cys Phe His Ser Asn Asp Val Asp Phe
        755                 760                 765

Ala Arg Lys Tyr Asn Glu Leu Ala Thr Lys Leu Gln Gly Met Cys Lys
    770                 775                 780

Ser Ile Arg Val Ala Leu Thr Asn His Val His Arg Glu Glu Leu Glu
785                 790                 795                 800

Leu Trp Pro Leu Phe Asp Lys His Phe Ser Val Glu Glu Gln Asp Lys
                805                 810                 815

Leu Val Gly Arg Ile Ile Gly Ser Thr Gly Ala Glu Val Leu Gln Ser
            820                 825                 830

Met Leu Pro Trp Val Thr Ser Val Leu Thr Gln Glu Gln Asn Lys
        835                 840                 845

Met Leu Asp Met Trp Lys Gln Ala Thr Lys Asn Thr Met Phe Gly Glu
850                 855                 860

Trp Leu Asn Glu Trp Trp Lys Gly Ala Gly Thr Ala Ser Asp Ser Ser
865                 870                 875                 880

Ala Glu Ala Ser Ser Ala Pro Glu Asp Ser His Leu Gln Asp Lys Leu
                885                 890                 895

Glu Gln Asn Asp Gln Met Phe Lys Pro Gly Trp Lys Asp Ile Phe Arg
            900                 905                 910

Met Asn Gln Ser Glu Leu Glu Ala Glu Val Arg Lys Val Ser Arg Asp
        915                 920                 925
```

| | | | | | | | | | | | | | |
|---|---|---|---|---|---|---|---|---|---|---|---|---|---|
| Ser | Thr | Leu | Asp | Pro | Arg | Arg | Lys | Ala | Tyr | Leu | Ile | Gln | Asn | Leu | Met |
| 930 | | | | | 935 | | | | | 940 | | | |

Ser Thr Leu Asp Pro Arg Arg Lys Ala Tyr Leu Ile Gln Asn Leu Met
930                 935                 940

Thr Ser Arg Trp Ile Ala Ala Gln Gln Lys Leu Pro Glu Pro Asn Ser
945                 950                 955                 960

Glu Glu Cys Asn His Asp Ala Ser Ile Pro Gly Cys Ala Pro Ser Tyr
            965                 970                 975

Arg Asp Gln Glu Lys Gln Ile Tyr Gly Cys Glu His Tyr Lys Arg Asn
            980                 985                 990

Cys Lys Leu Val Ala Ala Cys Cys Asn Lys Leu Phe Thr Cys Arg Phe
            995                 1000                1005

Cys His Asp Lys Val Ser Asp His Thr Met Glu Arg Lys Ala Thr
    1010                1015                1020

Gln Glu Met Met Cys Met Val Cys Leu Lys Ile Gln Pro Val Gly
    1025                1030                1035

Ser Phe Cys Gln Thr Pro Ser Cys Asn Arg Leu Ser Met Ala Lys
    1040                1045                1050

Tyr Tyr Cys Asn Ile Cys Lys Phe Phe Asp Asp Glu Arg Thr Val
    1055                1060                1065

Tyr His Cys Pro Phe Cys Asn Leu Cys Arg Leu Gly Lys Gly Leu
    1070                1075                1080

Gly Val Asp Phe Phe His Cys Met Lys Cys Asn Cys Cys Leu Gly
    1085                1090                1095

Met Lys Leu Thr Glu His Lys Cys Arg Glu Lys Gly Leu Glu Thr
    1100                1105                1110

Asn Cys Pro Ile Cys Cys Asp Phe Leu Phe Thr Ser Ser Ala Ala
    1115                1120                1125

Val Arg Ala Leu Pro Cys Gly His Phe Met His Ser Ala Cys Phe
    1130                1135                1140

Gln Ala Tyr Thr Cys Ser His Tyr Thr Cys Pro Ile Cys Cys Lys
    1145                1150                1155

Ser Leu Gly Asp Met Ala Val Tyr Phe Gly Met Leu Asp Ala Leu
    1160                1165                1170

Leu Ala Ala Glu Glu Leu Pro Glu Glu Tyr Arg Asp Arg Cys Gln
    1175                1180                1185

Asp Ile Leu Cys Asn Asp Cys Glu Arg Lys Gly Arg Cys Arg Phe
    1190                1195                1200

His Trp Leu Tyr His Lys Cys Gly Ser Cys Gly Ser Tyr Asn Thr
    1205                1210                1215

Arg Val Ile Lys Thr Ala Thr Ala Asp Cys Ser Thr Pro Asn
    1220                1225                1230

<210> SEQ ID NO 11
<211> LENGTH: 1152
<212> TYPE: DNA
<213> ORGANISM: Zea mays

<400> SEQUENCE: 11
atggagagct gggtccgcgc ggtggtggag gccatccact cctctcgctc ccagacagtc    60
atctacctcg ccggcggtgc atcccaggcg ctcggttggc tcctctccgt gcccggcgct   120
tcgggcaccg tcctcgaggt cgtcgtgccc tactctaggg cctccatggc gcagctcctt   180
ggcaagatgc ccctgcaatt cactagcaag caggctgcag aggacatggc actggccgca   240
tacaatcgag cactcaagct ttctggacca ggtctgcaag ttatgggtgt tggatttact   300
gggtcactgg cgagctcacg tccaaaacat ggtgaccaca ggttttatgt gtcaacatgg   360

```
acacataatt gtctcaggac atcacatgtt accttgtcga agggtttacg gagtagggag    420
gaagaagaca aggtttcaag ctactttttg cttaaggcaa tagcagatac ctgcagagtt    480
tctgcaacca ttcagccaga cattcacaaa tctgaaattc agaagaaat catggaacaa     540
tttgatgaag atcaagaact ccagcaagtt attaatgggc aagtttgcat gaaagtatat    600
aattttgctg ctccggcgga aagtaacttg aacagaaaaa taattctgcc tggttcgttc    660
aaccccttgc acgatggtca ccttagattg ctagaagctg cagtaagcat gtgtgatgat    720
gggcttccat tctttgagat atcagcaatt aatgctgata aacctccact atctattgca    780
gaaattaaga ggcgtgttga gcaatttaga aaagcaggga agaatgtgat tatatctaac    840
cagccatact tctataagaa agcagaactt ttcccaggaa gcgcttttat aattggtgca    900
gacactgcag caaggcttgt taaccctaag tactatggag gagattacaa cagaatgctg    960
gagatacttc tcgaatgtaa gagcataggg actacttttc ttgttggtgg tcgaaagatt   1020
gaaggagatt tcaaggtcct tgagaactta gacattccag aagagctgag agaaatgttc   1080
atttctattc cggaggaaaa gtttcgcata gatatttcat ctactgaaat aagaaagagc   1140
caagggctct ga                                                      1152
```

<210> SEQ ID NO 12
<211> LENGTH: 383
<212> TYPE: PRT
<213> ORGANISM: Zea mays

<400> SEQUENCE: 12

```
Met Glu Ser Trp Val Arg Ala Val Val Glu Ala Ile His Ser Ser Arg
 1               5                   10                  15

Ser Gln Thr Val Ile Tyr Leu Ala Gly Gly Ala Ser Gln Ala Leu Gly
             20                  25                  30

Trp Leu Leu Ser Val Pro Gly Ala Ser Gly Thr Val Leu Glu Val Val
         35                  40                  45

Val Pro Tyr Ser Arg Ala Ser Met Ala Gln Leu Leu Gly Lys Met Pro
     50                  55                  60

Leu Gln Phe Thr Ser Lys Gln Ala Ala Glu Asp Met Ala Leu Ala Ala
 65                  70                  75                  80

Tyr Asn Arg Ala Leu Lys Leu Ser Gly Pro Gly Leu Gln Val Met Gly
                 85                  90                  95

Val Gly Phe Thr Gly Ser Leu Ala Ser Ser Arg Pro Lys His Gly Asp
            100                 105                 110

His Arg Phe Tyr Val Ser Thr Trp Thr His Asn Cys Leu Arg Thr Ser
        115                 120                 125

His Val Thr Leu Ser Lys Gly Leu Arg Ser Arg Glu Glu Glu Asp Lys
    130                 135                 140

Val Ser Ser Tyr Phe Leu Leu Lys Ala Ile Ala Asp Thr Cys Arg Val
145                 150                 155                 160

Ser Ala Thr Ile Gln Pro Asp Ile His Lys Ser Glu Ile Pro Glu Glu
                165                 170                 175

Ile Met Glu Gln Phe Asp Glu Asp Gln Glu Leu Gln Gln Val Ile Asn
            180                 185                 190

Gly Gln Val Cys Met Lys Val Tyr Asn Phe Ala Ala Pro Ala Glu Ser
        195                 200                 205

Asn Leu Asn Arg Lys Ile Ile Leu Pro Gly Ser Phe Asn Pro Leu His
    210                 215                 220
```

```
Asp Gly His Leu Arg Leu Leu Glu Ala Ala Val Ser Met Cys Asp Asp
225                 230                 235                 240

Gly Leu Pro Phe Phe Glu Ile Ser Ala Ile Asn Ala Asp Lys Pro Pro
            245                 250                 255

Leu Ser Ile Ala Glu Ile Lys Arg Arg Val Glu Gln Phe Arg Lys Ala
        260                 265                 270

Gly Lys Asn Val Ile Ile Ser Asn Gln Pro Tyr Phe Tyr Lys Lys Ala
    275                 280                 285

Glu Leu Phe Pro Gly Ser Ala Phe Ile Ile Gly Ala Asp Thr Ala Ala
290                 295                 300

Arg Leu Val Asn Pro Lys Tyr Tyr Gly Gly Asp Tyr Asn Arg Met Leu
305                 310                 315                 320

Glu Ile Leu Leu Glu Cys Lys Ser Ile Gly Thr Thr Phe Leu Val Gly
                325                 330                 335

Gly Arg Lys Ile Glu Gly Asp Phe Lys Val Leu Glu Asn Leu Asp Ile
            340                 345                 350

Pro Glu Glu Leu Arg Glu Met Phe Ile Ser Ile Pro Glu Glu Lys Phe
        355                 360                 365

Arg Ile Asp Ile Ser Ser Thr Glu Ile Arg Lys Ser Gln Gly Leu
    370                 375                 380

<210> SEQ ID NO 13
<211> LENGTH: 666
<212> TYPE: DNA
<213> ORGANISM: Zea mays

<400> SEQUENCE: 13
atgcacccta attttccaag cgatcatggc aacggacgag gggtgggcgg cggcggcggc        60
catagcaggc gcaagccgat tcatcagctt ctcggtggag ggcgagccgc ggacatcttg       120
ctgtggaagg acaggaattt gtctgcaggc ctgctcgctg gggccacgct ggtatggtac       180
ctgttcgagg ttgttgagta cagcattgta ccgctcgttt gccagatagc catcctggcc       240
atgctcgtcg tcttcatctg gtcgaatgct gcgcccctct gaacatagcc cctccaagg       300 atcccagaag tgatcatctc tgagcatgcc ttccgacaaa tagcacagat cgtccattac       360
aaactggcac acaccgtgtc tgctctttat gacattgcat gcgggaagga tctgaagaaa       420
ttcctcctgg tggtcttatc actgctaata gtgtcagagg ttggaagttc ttacagcttc       480
acaagtcttc tatatcttgg atttctttgc gcccacactt tgccagcgtt gtaccaagaa       540
tatgagacag aggttgacca ccttgccgca aggggtagtg aagacatcaa gaggttctac       600
aagaggattg attccaattt gctgaacaaa ataccaaggg gcccagtcaa gacaaaagtt       660
aaataa                                                                  666

<210> SEQ ID NO 14
<211> LENGTH: 221
<212> TYPE: PRT
<213> ORGANISM: Zea mays

<400> SEQUENCE: 14

Met His Pro Asn Phe Pro Ser Asp His Gly Asn Gly Arg Gly Val Gly
1               5                   10                  15

Gly Gly Gly Gly His Ser Arg Arg Lys Pro Ile His Gln Leu Leu Gly
            20                  25                  30

Gly Gly Arg Ala Ala Asp Ile Leu Leu Trp Lys Asp Arg Asn Leu Ser
        35                  40                  45
```

Ala Gly Leu Leu Ala Gly Ala Thr Leu Val Trp Tyr Leu Phe Glu Val
 50                  55                  60

Val Glu Tyr Ser Ile Val Pro Leu Val Cys Gln Ile Ala Ile Leu Ala
 65                  70                  75                  80

Met Leu Val Val Phe Ile Trp Ser Asn Ala Ala Pro Leu Leu Asn Ile
                 85                  90                  95

Ala Pro Pro Arg Ile Pro Glu Val Ile Ser Glu His Ala Phe Arg
            100                 105                 110

Gln Ile Ala Gln Ile Val His Tyr Lys Leu Ala His Thr Val Ser Ala
            115                 120                 125

Leu Tyr Asp Ile Ala Cys Gly Lys Asp Leu Lys Phe Leu Leu Val
    130                 135                 140

Val Leu Ser Leu Leu Ile Val Ser Glu Val Gly Ser Ser Tyr Ser Phe
145                 150                 155                 160

Thr Ser Leu Leu Tyr Leu Gly Phe Leu Cys Ala His Thr Leu Pro Ala
                165                 170                 175

Leu Tyr Gln Arg Tyr Glu Thr Glu Val Asp His Leu Ala Ala Arg Gly
            180                 185                 190

Ser Glu Asp Ile Lys Arg Phe Tyr Lys Arg Ile Asp Ser Asn Leu Leu
    195                 200                 205

Asn Lys Ile Pro Arg Gly Pro Val Lys Thr Lys Val Lys
    210                 215                 220

<210> SEQ ID NO 15
<211> LENGTH: 1113
<212> TYPE: DNA
<213> ORGANISM: Zea mays

<400> SEQUENCE: 15

```
atgggcggcg tcacgtccac catcgccgcg cgcttcgcct tcttcccgcc gacgccgccg      60
tcctacaccg tcgtcgtcgc cgacgccgcc accggtcgcc tcgccatccc ggagatctcc     120
cgggcaccct cgcgccgtcg gaggcgggac ggcgccggcg ccggggggctc ctcctcggcc    180 tcctccgtcg tcgcggccgc cgaggaggag gacggcgcgg aggtggtgcg cctccggacc     240
cgccgcggga acgagatcgt gggggtctac gtgcgccacg cgcgggcctc cgccaccgtg     300
ctctactccc acggcaacgc cgccgacctc ggccagatgt acgggctctt cgtcgagctc     360
agccgccgcc tccgcgtcaa cctctttggg tatgattatt ctggttatgg agatctaca     420 gggaagccca ctgagtgtaa tacatatgca gacattgaag cagcatataa ctgcctcaag     480
gaaaaatatg gtgtagcaga tgaggatata atcttatatg gtcagtctgt ggaagtggt     540 ccaaccattg atcttgcttc gcggttgcca gacttgcgag ctgtggtttt gcatagtcct     600
attttatctg gactaagagt aatatatcca gtcaagcgga cgttttggtt tgacatttac     660
aagaacatcg ataaaattgg cttggtaaat tgtccggtgc ttgtcattca tggtacatca     720
gatgacgtgg ttgactgctc ccacggaaaa cagctatggg agcactgcaa agtaaaatat     780
tctccactgt ggttaagtgg tggtggccac tgcaatctcg agctatatcc agattacatt     840
aagcacttga aaagtttgt gtcaagcgtt agcaaaaaag catcatcgaa acctgaccca     900
aaagaaacaa cgacaaagga tgacactacc agtaaagaaa cagaggaagc gtacccggag     960
aaacctcaag aggccaagaa gtgcccgcag atctcgcgaa agagcctgga cagccgattc    1020
gggaaatcca aacagtgga tgttcctgat aaaccacgga tgagctcgga cgacatcgac    1080
aagttccgga ggagcagatg cttggtctgg tga                                 1113
```

```
<210> SEQ ID NO 16
<211> LENGTH: 370
<212> TYPE: PRT
<213> ORGANISM: Zea mays

<400> SEQUENCE: 16

Met Gly Gly Val Thr Ser Thr Ile Ala Ala Arg Phe Ala Phe Phe Pro
1               5                   10                  15

Pro Thr Pro Pro Ser Tyr Thr Val Val Val Ala Asp Ala Ala Thr Gly
            20                  25                  30

Arg Leu Ala Ile Pro Glu Ile Ser Arg Ala Pro Ser Arg Arg Arg Arg
        35                  40                  45

Arg Asp Gly Ala Gly Ala Gly Gly Ser Ser Ser Ala Ser Ser Val Val
    50                  55                  60

Ala Ala Ala Glu Glu Asp Gly Ala Glu Val Val Arg Leu Arg Thr
65                  70                  75                  80

Arg Arg Gly Asn Glu Ile Val Gly Val Tyr Val Arg His Ala Arg Ala
                85                  90                  95

Ser Ala Thr Val Leu Tyr Ser His Gly Asn Ala Ala Asp Leu Gly Gln
            100                 105                 110

Met Tyr Gly Leu Phe Val Glu Leu Ser Arg Arg Leu Arg Val Asn Leu
        115                 120                 125

Phe Gly Tyr Asp Tyr Ser Gly Tyr Gly Arg Ser Thr Gly Lys Pro Thr
    130                 135                 140

Glu Cys Asn Thr Tyr Ala Asp Ile Glu Ala Ala Tyr Asn Cys Leu Lys
145                 150                 155                 160

Glu Lys Tyr Gly Val Ala Asp Glu Asp Ile Ile Leu Tyr Gly Gln Ser
                165                 170                 175

Val Gly Ser Gly Pro Thr Ile Asp Leu Ala Ser Arg Leu Pro Asp Leu
            180                 185                 190

Arg Ala Val Val Leu His Ser Pro Ile Leu Ser Gly Leu Arg Val Ile
        195                 200                 205

Tyr Pro Val Lys Arg Thr Phe Trp Phe Asp Ile Tyr Lys Asn Ile Asp
    210                 215                 220

Lys Ile Gly Leu Val Asn Cys Pro Val Leu Val Ile His Gly Thr Ser
225                 230                 235                 240

Asp Asp Val Val Asp Cys Ser His Gly Lys Gln Leu Trp Glu His Cys
                245                 250                 255

Lys Val Lys Tyr Ser Pro Leu Trp Leu Ser Gly Gly His Cys Asn
            260                 265                 270

Leu Glu Leu Tyr Pro Asp Tyr Ile Lys His Leu Lys Lys Phe Val Ser
        275                 280                 285

Ser Val Ser Lys Lys Ala Ser Ser Lys Pro Asp Pro Lys Glu Thr Thr
    290                 295                 300

Thr Lys Asp Asp Thr Thr Ser Lys Glu Thr Glu Glu Ala Tyr Pro Glu
305                 310                 315                 320

Lys Pro Gln Glu Ala Lys Lys Cys Pro Gln Ile Ser Arg Lys Ser Leu
                325                 330                 335

Asp Ser Arg Phe Gly Lys Ser Lys Thr Val Asp Val Pro Asp Lys Pro
            340                 345                 350

Arg Met Ser Ser Asp Asp Ile Asp Lys Phe Arg Arg Ser Arg Cys Leu
        355                 360                 365

Val Trp
    370
```

<210> SEQ ID NO 17
<211> LENGTH: 47
<212> TYPE: DNA
<213> ORGANISM: Artificial Sequence
<220> FEATURE:
<223> OTHER INFORMATION: SYN14136 Primer Allel X

<400> SEQUENCE: 17
gaaggtgacc aagttcatgc tcatcttgtt cggccttttc tacacta          47

<210> SEQ ID NO 18
<211> LENGTH: 46
<212> TYPE: DNA
<213> ORGANISM: Artificial Sequence
<220> FEATURE:
<223> OTHER INFORMATION: SYN14136 Primer Allel Y

<400> SEQUENCE: 18
gaaggtcgga gtcaacggat tatcttgttc ggccttttct acactc           46

<210> SEQ ID NO 19
<211> LENGTH: 28
<212> TYPE: DNA
<213> ORGANISM: Artificial Sequence
<220> FEATURE:
<223> OTHER INFORMATION: SYN14136 gemeinsamer Primer

<400> SEQUENCE: 19
agaaccaaaa attcaccagc tgtgagaa                               28

<210> SEQ ID NO 20
<211> LENGTH: 44
<212> TYPE: DNA
<213> ORGANISM: Artificial Sequence
<220> FEATURE:
<223> OTHER INFORMATION: PZE-108076510 Primer Allel X

<400> SEQUENCE: 20
gaaggtgacc aagttcatgc tagcggcggg ctttcataca attt             44

<210> SEQ ID NO 21
<211> LENGTH: 43
<212> TYPE: DNA
<213> ORGANISM: Artificial Sequence
<220> FEATURE:
<223> OTHER INFORMATION: PZE-108076510 Primer Allel Y

<400> SEQUENCE: 21
gaaggtcgga gtcaacggat tgcggcgggc tttcatacaa ttc              43

<210> SEQ ID NO 22
<211> LENGTH: 24
<212> TYPE: DNA
<213> ORGANISM: Artificial Sequence
<220> FEATURE:
<223> OTHER INFORMATION: PZE-108076510 gemeinsamer Primer

<400> SEQUENCE: 22
cttgtgatca cgtgaggggc tcaa                                   24

<210> SEQ ID NO 23
<211> LENGTH: 49
<212> TYPE: DNA
<213> ORGANISM: Artificial Sequence
<220> FEATURE:

<223> OTHER INFORMATION: SYN24931 Primer Allel X

<400> SEQUENCE: 23
gaaggtgacc aagttcatgc tccattagat gagaaagcaa agagaacta        49

<210> SEQ ID NO 24
<211> LENGTH: 48
<212> TYPE: DNA
<213> ORGANISM: Artificial Sequence
<220> FEATURE:
<223> OTHER INFORMATION: SYN24931 Primer Allel Y

<400> SEQUENCE: 24
gaaggtcgga gtcaacggat tcattagatg agaaagcaaa gagaactg         48

<210> SEQ ID NO 25
<211> LENGTH: 25
<212> TYPE: DNA
<213> ORGANISM: Artificial Sequence
<220> FEATURE:
<223> OTHER INFORMATION: SYN24931 gemeinsamer Primer

<400> SEQUENCE: 25
attggtcgac atctcatgga ggctt                                  25

<210> SEQ ID NO 26
<211> LENGTH: 36
<212> TYPE: DNA
<213> ORGANISM: Artificial Sequence
<220> FEATURE:
<223> OTHER INFORMATION: PZE-108077560 Primer Allel X

<400> SEQUENCE: 26
gaaggtgacc aagttcatgc tgcagtggcc tgcgca                      36

<210> SEQ ID NO 27
<211> LENGTH: 39
<212> TYPE: DNA
<213> ORGANISM: Artificial Sequence
<220> FEATURE:
<223> OTHER INFORMATION: PZE-108077560 Primer Allel Y

<400> SEQUENCE: 27
gaaggtcgga gtcaacggat tgctgcagtg gcctgcgcg                   39

<210> SEQ ID NO 28
<211> LENGTH: 28
<212> TYPE: DNA
<213> ORGANISM: Artificial Sequence
<220> FEATURE:
<223> OTHER INFORMATION: PZE-108077560 gemeinsamer Primer

<400> SEQUENCE: 28
agataatgag tcatcaggct atcagcaa                               28

<210> SEQ ID NO 29
<211> LENGTH: 49
<212> TYPE: DNA
<213> ORGANISM: Artificial Sequence
<220> FEATURE:
<223> OTHER INFORMATION: PZE-108093423 Primer Allel X

<400> SEQUENCE: 29
gaaggtgacc aagttcatgc tgtaatccat tgtgaacata tcgctatca        49

```
<210> SEQ ID NO 30
<211> LENGTH: 47
<212> TYPE: DNA
<213> ORGANISM: Artificial Sequence
<220> FEATURE:
<223> OTHER INFORMATION: PZE-108093423 Primer Allel Y

<400> SEQUENCE: 30
gaaggtcgga gtcaacggat taatccattg tgaacatatc gctatcg          47

<210> SEQ ID NO 31
<211> LENGTH: 25
<212> TYPE: DNA
<213> ORGANISM: Artificial Sequence
<220> FEATURE:
<223> OTHER INFORMATION: PZE-108093423 gemeinsamer Primer

<400> SEQUENCE: 31
gaaacggttc tgctgcagtt tggta                                   25

<210> SEQ ID NO 32
<211> LENGTH: 47
<212> TYPE: DNA
<213> ORGANISM: Artificial Sequence
<220> FEATURE:
<223> OTHER INFORMATION: PZE-108093748 Primer Allel X

<400> SEQUENCE: 32
gaaggtgacc aagttcatgc tggatagagt tgcagctaat gcttcaa          47

<210> SEQ ID NO 33
<211> LENGTH: 46
<212> TYPE: DNA
<213> ORGANISM: Artificial Sequence
<220> FEATURE:
<223> OTHER INFORMATION: PZE-108093748 Primer Allel Y

<400> SEQUENCE: 33
gaaggtcgga gtcaacggat tgatagagtt gcagctaatg cttcag           46

<210> SEQ ID NO 34
<211> LENGTH: 28
<212> TYPE: DNA
<213> ORGANISM: Artificial Sequence
<220> FEATURE:
<223> OTHER INFORMATION: PZE-108093748 gemeinsamer Primer

<400> SEQUENCE: 34
cctgcgcttt gtaaataagt taggcaaa                                28

<210> SEQ ID NO 35
<211> LENGTH: 38
<212> TYPE: DNA
<213> ORGANISM: Artificial Sequence
<220> FEATURE:
<223> OTHER INFORMATION: PZE-108107671 Primer Allel X

<400> SEQUENCE: 35
gaaggtgacc aagttcatgc ttgcacctgc acacgccg                     38

<210> SEQ ID NO 36
<211> LENGTH: 40
<212> TYPE: DNA
<213> ORGANISM: Artificial Sequence
<220> FEATURE:
<223> OTHER INFORMATION: PZE-108107671 Primer Allel Y
```

<400> SEQUENCE: 36
gaaggtcgga gtcaacggat tcttgcacct gcacacgccc          40

<210> SEQ ID NO 37
<211> LENGTH: 21
<212> TYPE: DNA
<213> ORGANISM: Artificial Sequence
<220> FEATURE:
<223> OTHER INFORMATION: PZE-108107671 gemeinsamer Primer

<400> SEQUENCE: 37
gatgccaagg atcgggcgct t          21

<210> SEQ ID NO 38
<211> LENGTH: 47
<212> TYPE: DNA
<213> ORGANISM: Artificial Sequence
<220> FEATURE:
<223> OTHER INFORMATION: SYN4196 Primer Allel X

<400> SEQUENCE: 38
gaaggtgacc aagttcatgc tctgcactct ggaatatcta taacaga          47

<210> SEQ ID NO 39
<211> LENGTH: 47
<212> TYPE: DNA
<213> ORGANISM: Artificial Sequence
<220> FEATURE:
<223> OTHER INFORMATION: SYN4196 Primer Allel Y

<400> SEQUENCE: 39
gaaggtcgga gtcaacggat tctgcactct ggaatatcta taacagc          47

<210> SEQ ID NO 40
<211> LENGTH: 25
<212> TYPE: DNA
<213> ORGANISM: Artificial Sequence
<220> FEATURE:
<223> OTHER INFORMATION: SYN4196 gemeinsamer Primer

<400> SEQUENCE: 40
tggtttatac caggaaggga cgcat          25

<210> SEQ ID NO 41
<211> LENGTH: 41
<212> TYPE: DNA
<213> ORGANISM: Artificial Sequence
<220> FEATURE:
<223> OTHER INFORMATION: MA0004 Primer Allel X

<400> SEQUENCE: 41
gaaggtgacc aagttcatgc tgcctcgtcc gcacttcacg t          41

<210> SEQ ID NO 42
<211> LENGTH: 40
<212> TYPE: DNA
<213> ORGANISM: Artificial Sequence
<220> FEATURE:
<223> OTHER INFORMATION: MA0004 Primer Allel Y

<400> SEQUENCE: 42
gaaggtcgga gtcaacggat tcctcgtccg cacttcacgg          40

<210> SEQ ID NO 43
<211> LENGTH: 22

```
<212> TYPE: DNA
<213> ORGANISM: Artificial Sequence
<220> FEATURE:
<223> OTHER INFORMATION: MA0004 gemeinsamer Primer

<400> SEQUENCE: 43
gtgtcaacgc cggatacggg at                                              22

<210> SEQ ID NO 44
<211> LENGTH: 52
<212> TYPE: DNA
<213> ORGANISM: Artificial Sequence
<220> FEATURE:
<223> OTHER INFORMATION: MA0005 Primer Allel X

<400> SEQUENCE: 44
gaaggtgacc aagttcatgc tccaaaattt tagaatcaca aacagattta cg            52

<210> SEQ ID NO 45
<211> LENGTH: 52
<212> TYPE: DNA
<213> ORGANISM: Artificial Sequence
<220> FEATURE:
<223> OTHER INFORMATION: MA0005 Primer Allel Y

<400> SEQUENCE: 45
gaaggtcgga gtcaacggat tccaaaattt tagaatcaca aacagattta ct            52

<210> SEQ ID NO 46
<211> LENGTH: 30
<212> TYPE: DNA
<213> ORGANISM: Artificial Sequence
<220> FEATURE:
<223> OTHER INFORMATION: MA0005 gemeinsamer Primer

<400> SEQUENCE: 46
aaacgccagt atcaaggagt tattagtatt                                      30

<210> SEQ ID NO 47
<211> LENGTH: 49
<212> TYPE: DNA
<213> ORGANISM: Artificial Sequence
<220> FEATURE:
<223> OTHER INFORMATION: MA0006 Primer Allel X

<400> SEQUENCE: 47
gaaggtgacc aagttcatgc tgcacacaaa cacaaattat gtcaaactg                 49

<210> SEQ ID NO 48
<211> LENGTH: 50
<212> TYPE: DNA
<213> ORGANISM: Artificial Sequence
<220> FEATURE:
<223> OTHER INFORMATION: MA0006 Primer Allel Y

<400> SEQUENCE: 48
gaaggtcgga gtcaacggat tagcacacaa acacaaatta tgtcaaacta               50

<210> SEQ ID NO 49
<211> LENGTH: 29
<212> TYPE: DNA
<213> ORGANISM: Artificial Sequence
<220> FEATURE:
<223> OTHER INFORMATION: MA0006 gemeinsamer Primer

<400> SEQUENCE: 49
```

```
ggctgtctta cgatatacca gttttctta                                          29

<210> SEQ ID NO 50
<211> LENGTH: 43
<212> TYPE: DNA
<213> ORGANISM: Artificial Sequence
<220> FEATURE:
<223> OTHER INFORMATION: PZE-108097482 Primer Allel X

<400> SEQUENCE: 50
gaaggtgacc aagttcatgc tagtcgggga tgcatgccat tga                          43

<210> SEQ ID NO 51
<211> LENGTH: 42
<212> TYPE: DNA
<213> ORGANISM: Artificial Sequence
<220> FEATURE:
<223> OTHER INFORMATION: PZE-108097482 Primer Allel Y

<400> SEQUENCE: 51
gaaggtcgga gtcaacggat tgtcggggat gcatgccatt gc                           42

<210> SEQ ID NO 52
<211> LENGTH: 25
<212> TYPE: DNA
<213> ORGANISM: Artificial Sequence
<220> FEATURE:
<223> OTHER INFORMATION: PZE-108097482 gemeinsamer Primer

<400> SEQUENCE: 52
gactccagag agagacagaa aggaa                                              25

<210> SEQ ID NO 53
<211> LENGTH: 41
<212> TYPE: DNA
<213> ORGANISM: Artificial Sequence
<220> FEATURE:
<223> OTHER INFORMATION: MA0002 Primer Allel X

<400> SEQUENCE: 53
gaaggtgacc aagttcatgc tgcctcgtcc gcacttcacg t                            41

<210> SEQ ID NO 54
<211> LENGTH: 40
<212> TYPE: DNA
<213> ORGANISM: Artificial Sequence
<220> FEATURE:
<223> OTHER INFORMATION: MA0002 Primer Allel Y

<400> SEQUENCE: 54
gaaggtcgga gtcaacggat tcctcgtccg cacttcacgg                              40

<210> SEQ ID NO 55
<211> LENGTH: 22
<212> TYPE: DNA
<213> ORGANISM: Artificial Sequence
<220> FEATURE:
<223> OTHER INFORMATION: MA0002 gemeinsamer Primer

<400> SEQUENCE: 55
gtgtcaacgc cggatacggg at                                                 22

<210> SEQ ID NO 56
<211> LENGTH: 41
<212> TYPE: DNA
<213> ORGANISM: Artificial Sequence
```

```
<220> FEATURE:
<223> OTHER INFORMATION: MA0003 Primer Allel X

<400> SEQUENCE: 56
gaaggtgacc aagttcatgc tccgtgatgc gccttgccgt a                    41

<210> SEQ ID NO 57
<211> LENGTH: 40
<212> TYPE: DNA
<213> ORGANISM: Artificial Sequence
<220> FEATURE:
<223> OTHER INFORMATION: MA0003 Primer Allel Y

<400> SEQUENCE: 57
gaaggtcgga gtcaacggat tcgtgatgcg ccttgccgtc                      40

<210> SEQ ID NO 58
<211> LENGTH: 24
<212> TYPE: DNA
<213> ORGANISM: Artificial Sequence
<220> FEATURE:
<223> OTHER INFORMATION: MA0003 gemeinsamer Primer

<400> SEQUENCE: 58
gcacatcaat cgactcagcc ctat                                       24

<210> SEQ ID NO 59
<211> LENGTH: 48
<212> TYPE: DNA
<213> ORGANISM: Artificial Sequence
<220> FEATURE:
<223> OTHER INFORMATION: MA0007 Primer Allel X

<400> SEQUENCE: 59
gaaggtgacc aagttcatgc tgaaattatt ctcagcgagc atataacc             48

<210> SEQ ID NO 60
<211> LENGTH: 49
<212> TYPE: DNA
<213> ORGANISM: Artificial Sequence
<220> FEATURE:
<223> OTHER INFORMATION: MA0007 Primer Allel Y

<400> SEQUENCE: 60
gaaggtcgga gtcaacggat tggaaattat tctcagcgag catataact            49

<210> SEQ ID NO 61
<211> LENGTH: 24
<212> TYPE: DNA
<213> ORGANISM: Artificial Sequence
<220> FEATURE:
<223> OTHER INFORMATION: MA0007 gemeinsamer Primer

<400> SEQUENCE: 61
cgaacaggca grcccatatg cttt                                       24

<210> SEQ ID NO 62
<211> LENGTH: 48
<212> TYPE: DNA
<213> ORGANISM: Artificial Sequence
<220> FEATURE:
<223> OTHER INFORMATION: MA0008 Primer Allel X

<400> SEQUENCE: 62
gaaggtgacc aagttcatgc tggtaaaatg aagtaaaagc atatgggc             48
```

<210> SEQ ID NO 63
<211> LENGTH: 50
<212> TYPE: DNA
<213> ORGANISM: Artificial Sequence
<220> FEATURE:
<223> OTHER INFORMATION: MA0008 Primer Allel Y

<400> SEQUENCE: 63
gaaggtcgga gtcaacggat tgaggtaaaa tgaagtaaaa gcatatgggt    50

<210> SEQ ID NO 64
<211> LENGTH: 25
<212> TYPE: DNA
<213> ORGANISM: Artificial Sequence
<220> FEATURE:
<223> OTHER INFORMATION: MA0008 gemeinsamer Primer

<400> SEQUENCE: 64
tagacggagg gtgtacttat gcgaa    25

<210> SEQ ID NO 65
<211> LENGTH: 51
<212> TYPE: DNA
<213> ORGANISM: Artificial Sequence
<220> FEATURE:
<223> OTHER INFORMATION: MA0009 Primer Allel X

<400> SEQUENCE: 65
gaaggtgacc aagttcatgc tgtaacaaat ttgtgcttta tgtttctggt t    51

<210> SEQ ID NO 66
<211> LENGTH: 49
<212> TYPE: DNA
<213> ORGANISM: Artificial Sequence
<220> FEATURE:
<223> OTHER INFORMATION: MA0009 Primer Allel Y

<400> SEQUENCE: 66
gaaggtcgga gtcaacggat taacaaattt gtgctttatg tttctggtg    49

<210> SEQ ID NO 67
<211> LENGTH: 29
<212> TYPE: DNA
<213> ORGANISM: Artificial Sequence
<220> FEATURE:
<223> OTHER INFORMATION: MA0009 gemeinsamer Primer

<400> SEQUENCE: 67
gatttsagca agattaagct gattcacgt    29

<210> SEQ ID NO 68
<211> LENGTH: 47
<212> TYPE: DNA
<213> ORGANISM: Artificial Sequence
<220> FEATURE:
<223> OTHER INFORMATION: MA0010 Primer Allel X

<400> SEQUENCE: 68
gaaggtgacc aagttcatgc tgttggtaag agcctatagt caataca    47

<210> SEQ ID NO 69
<211> LENGTH: 47
<212> TYPE: DNA
<213> ORGANISM: Artificial Sequence
<220> FEATURE:
<223> OTHER INFORMATION: MA0010 Primer Allel Y

```
<400> SEQUENCE: 69
gaaggtcgga gtcaacggat tgttggtaag agcctatagt caatacc                47

<210> SEQ ID NO 70
<211> LENGTH: 30
<212> TYPE: DNA
<213> ORGANISM: Artificial Sequence
<220> FEATURE:
<223> OTHER INFORMATION: MA0010 gemeinsamer Primer

<400> SEQUENCE: 70
aattcatcay atgcttttct tctgctcttt                                   30

<210> SEQ ID NO 71
<211> LENGTH: 44
<212> TYPE: DNA
<213> ORGANISM: Artificial Sequence
<220> FEATURE:
<223> OTHER INFORMATION: MA0011 Primer Allel X

<400> SEQUENCE: 71
gaaggtgacc aagttcatgc tccttcctac agaagaacga gagc                   44

<210> SEQ ID NO 72
<211> LENGTH: 44
<212> TYPE: DNA
<213> ORGANISM: Artificial Sequence
<220> FEATURE:
<223> OTHER INFORMATION: MA0011 Primer Allel Y

<400> SEQUENCE: 72
gaaggtcgga gtcaacggat tccttcctac agaagaacga gagt                   44

<210> SEQ ID NO 73
<211> LENGTH: 25
<212> TYPE: DNA
<213> ORGANISM: Artificial Sequence
<220> FEATURE:
<223> OTHER INFORMATION: MA0011 gemeinsamer Primer

<400> SEQUENCE: 73
ttcacgtccg cgtaggtgta tcttt                                        25

<210> SEQ ID NO 74
<211> LENGTH: 47
<212> TYPE: DNA
<213> ORGANISM: Artificial Sequence
<220> FEATURE:
<223> OTHER INFORMATION: MA0012 Primer Allel X

<400> SEQUENCE: 74
gaaggtgacc aagttcatgc tatagacatc agacttgctg cttattg                47

<210> SEQ ID NO 75
<211> LENGTH: 49
<212> TYPE: DNA
<213> ORGANISM: Artificial Sequence
<220> FEATURE:
<223> OTHER INFORMATION: MA0012 Primer Allel Y

<400> SEQUENCE: 75
gaaggtcgga gtcaacggat tctatagaca tcagacttgc tgcttatta              49

<210> SEQ ID NO 76
```

```
<211> LENGTH: 25
<212> TYPE: DNA
<213> ORGANISM: Artificial Sequence
<220> FEATURE:
<223> OTHER INFORMATION: MA0012 gemeinsamer Primer

<400> SEQUENCE: 76
cccggaggtc tactcaaagc aattt                                          25

<210> SEQ ID NO 77
<211> LENGTH: 45
<212> TYPE: DNA
<213> ORGANISM: Artificial Sequence
<220> FEATURE:
<223> OTHER INFORMATION: MA0013 Primer Allel X

<400> SEQUENCE: 77
gaaggtgacc aagttcatgc tccttccgac aaatagcaca gatca                    45

<210> SEQ ID NO 78
<211> LENGTH: 44
<212> TYPE: DNA
<213> ORGANISM: Artificial Sequence
<220> FEATURE:
<223> OTHER INFORMATION: MA0013 Primer Allel Y

<400> SEQUENCE: 78
gaaggtcgga gtcaacggat tcttccgaca aatagcacag atcg                     44

<210> SEQ ID NO 79
<211> LENGTH: 25
<212> TYPE: DNA
<213> ORGANISM: Artificial Sequence
<220> FEATURE:
<223> OTHER INFORMATION: MA0013 gemeinsamer Primer

<400> SEQUENCE: 79
gacacggtgt gtgccagttt gtaat                                          25

<210> SEQ ID NO 80
<211> LENGTH: 47
<212> TYPE: DNA
<213> ORGANISM: Artificial Sequence
<220> FEATURE:
<223> OTHER INFORMATION: MA0014 Primer Allel X

<400> SEQUENCE: 80
gaaggtgacc aagttcatgc tcaacctctg acactattag cagtgat                  47

<210> SEQ ID NO 81
<211> LENGTH: 46
<212> TYPE: DNA
<213> ORGANISM: Artificial Sequence
<220> FEATURE:
<223> OTHER INFORMATION: MA0014 Primer Allel Y

<400> SEQUENCE: 81
gaaggtcgga gtcaacggat taacctctga cactattagc agtgac                   46

<210> SEQ ID NO 82
<211> LENGTH: 29
<212> TYPE: DNA
<213> ORGANISM: Artificial Sequence
<220> FEATURE:
<223> OTHER INFORMATION: MA0014 gemeinsamer Primer

<400> SEQUENCE: 82
```

```
tgttctgttt ctgattctaa ggtggtctt                                        29

<210> SEQ ID NO 83
<211> LENGTH: 44
<212> TYPE: DNA
<213> ORGANISM: Artificial Sequence
<220> FEATURE:
<223> OTHER INFORMATION: MA0015 Primer Allel X

<400> SEQUENCE: 83
gaaggtgacc aagttcatgc tacaggtatg ccttgctcat aagc                       44

<210> SEQ ID NO 84
<211> LENGTH: 45
<212> TYPE: DNA
<213> ORGANISM: Artificial Sequence
<220> FEATURE:
<223> OTHER INFORMATION: MA0015 Primer Allel Y

<400> SEQUENCE: 84
gaaggtcgga gtcaacggat tcacaggtat gccttgctca taaga                      45

<210> SEQ ID NO 85
<211> LENGTH: 26
<212> TYPE: DNA
<213> ORGANISM: Artificial Sequence
<220> FEATURE:
<223> OTHER INFORMATION: MA0015 gemeinsamer Primer

<400> SEQUENCE: 85
catarccact gttctaggct ggtgaa                                           26

<210> SEQ ID NO 86
<211> LENGTH: 43
<212> TYPE: DNA
<213> ORGANISM: Artificial Sequence
<220> FEATURE:
<223> OTHER INFORMATION: MA0016 Primer Allel X

<400> SEQUENCE: 86
gaaggtgacc aagttcatgc tcgagcaacc ggagataacc aca                        43

<210> SEQ ID NO 87
<211> LENGTH: 42
<212> TYPE: DNA
<213> ORGANISM: Artificial Sequence
<220> FEATURE:
<223> OTHER INFORMATION: MA0016 Primer Allel Y

<400> SEQUENCE: 87
gaaggtcgga gtcaacggat tgagcaaccg gagataacca cg                         42

<210> SEQ ID NO 88
<211> LENGTH: 30
<212> TYPE: DNA
<213> ORGANISM: Artificial Sequence
<220> FEATURE:
<223> OTHER INFORMATION: MA0016 gemeinsamer Primer

<400> SEQUENCE: 88
tttcggtaac ttgagacctc taattctttt                                       30

<210> SEQ ID NO 89
<211> LENGTH: 38
<212> TYPE: DNA
```

```
<213> ORGANISM: Artificial Sequence
<220> FEATURE:
<223> OTHER INFORMATION: MA0017 Primer Allel X

<400> SEQUENCE: 89
gaaggtgacc aagttcatgc tcccaaacac gtcgcacg                           38

<210> SEQ ID NO 90
<211> LENGTH: 43
<212> TYPE: DNA
<213> ORGANISM: Artificial Sequence
<220> FEATURE:
<223> OTHER INFORMATION: MA0017 Primer Allel Y

<400> SEQUENCE: 90
gaaggtcgga gtcaacggat tatgctccca aacacgtcgc aca                     43

<210> SEQ ID NO 91
<211> LENGTH: 23
<212> TYPE: DNA
<213> ORGANISM: Artificial Sequence
<220> FEATURE:
<223> OTHER INFORMATION: MA0017 gemeinsamer Primer

<400> SEQUENCE: 91
cgcccgtcac ctaacaacag caa                                            23

<210> SEQ ID NO 92
<211> LENGTH: 50
<212> TYPE: DNA
<213> ORGANISM: Artificial Sequence
<220> FEATURE:
<223> OTHER INFORMATION: MA0018 Primer Allel X

<400> SEQUENCE: 92
gaaggtgacc aagttcatgc tattctagag tatagatgtc taaacaaacc              50

<210> SEQ ID NO 93
<211> LENGTH: 47
<212> TYPE: DNA
<213> ORGANISM: Artificial Sequence
<220> FEATURE:
<223> OTHER INFORMATION: MA0018 Primer Allel Y

<400> SEQUENCE: 93
gaaggtcgga gtcaacggat tctagagtat agatgtctaa acaaact                 47

<210> SEQ ID NO 94
<211> LENGTH: 22
<212> TYPE: DNA
<213> ORGANISM: Artificial Sequence
<220> FEATURE:
<223> OTHER INFORMATION: MA0018 gemeinsamer Primer

<400> SEQUENCE: 94
cgacgggtga cgagtgacga tt                                             22

<210> SEQ ID NO 95
<211> LENGTH: 46
<212> TYPE: DNA
<213> ORGANISM: Artificial Sequence
<220> FEATURE:
<223> OTHER INFORMATION: MA0019 Primer Allel X

<400> SEQUENCE: 95
gaaggtgacc aagttcatgc tataaatatc tactcggcgc caatac                  46
```

<210> SEQ ID NO 96
<211> LENGTH: 46
<212> TYPE: DNA
<213> ORGANISM: Artificial Sequence
<220> FEATURE:
<223> OTHER INFORMATION: MA0019 Primer Allel Y

<400> SEQUENCE: 96
gaaggtcgga gtcaacggat tataaatatc tactcggcgc caatag          46

<210> SEQ ID NO 97
<211> LENGTH: 27
<212> TYPE: DNA
<213> ORGANISM: Artificial Sequence
<220> FEATURE:
<223> OTHER INFORMATION: MA0019 gemeinsamer Primer

<400> SEQUENCE: 97
ygagatctag gtgtcatctt ctagtca          27

<210> SEQ ID NO 98
<211> LENGTH: 42
<212> TYPE: DNA
<213> ORGANISM: Artificial Sequence
<220> FEATURE:
<223> OTHER INFORMATION: MA0020 Primer Allel X

<400> SEQUENCE: 98
gaaggtgacc aagttcatgc tttgccagca tctctctgct cc          42

<210> SEQ ID NO 99
<211> LENGTH: 46
<212> TYPE: DNA
<213> ORGANISM: Artificial Sequence
<220> FEATURE:
<223> OTHER INFORMATION: MA0020 Primer Allel Y

<400> SEQUENCE: 99
gaaggtcgga gtcaacggat taattttgcc agcatctctc tgctca          46

<210> SEQ ID NO 100
<211> LENGTH: 25
<212> TYPE: DNA
<213> ORGANISM: Artificial Sequence
<220> FEATURE:
<223> OTHER INFORMATION: MA0020 gemeinsamer Primer

<400> SEQUENCE: 100
gtgaatcgga gaccaaggat tgctt          25

<210> SEQ ID NO 101
<211> LENGTH: 45
<212> TYPE: DNA
<213> ORGANISM: Artificial Sequence
<220> FEATURE:
<223> OTHER INFORMATION: PZE-108095998 Primer Allel X

<400> SEQUENCE: 101
gaaggtgacc aagttcatgc ttcaaacaag caagaggagc agcat          45

<210> SEQ ID NO 102
<211> LENGTH: 44
<212> TYPE: DNA
<213> ORGANISM: Artificial Sequence
<220> FEATURE:

<223> OTHER INFORMATION: PZE-108095998 Primer Allel Y

<400> SEQUENCE: 102
gaaggtcgga gtcaacggat tcaaacaagc aagaggagca gcag                    44

<210> SEQ ID NO 103
<211> LENGTH: 25
<212> TYPE: DNA
<213> ORGANISM: Artificial Sequence
<220> FEATURE:
<223> OTHER INFORMATION: PZE-108095998 gemeinsamer Primer

<400> SEQUENCE: 103
ttgtctcggt tgttaggtcg ccaat                                         25

<210> SEQ ID NO 104
<211> LENGTH: 45
<212> TYPE: DNA
<213> ORGANISM: Artificial Sequence
<220> FEATURE:
<223> OTHER INFORMATION: PZE-108096011 Primer Allel X

<400> SEQUENCE: 104
gaaggtgacc aagttcatgc tccactaatg cagagatgga gacta                   45

<210> SEQ ID NO 105
<211> LENGTH: 44
<212> TYPE: DNA
<213> ORGANISM: Artificial Sequence
<220> FEATURE:
<223> OTHER INFORMATION: PZE-108096011 Primer Allel Y

<400> SEQUENCE: 105
gaaggtcgga gtcaacggat tcactaatgc agagatggag actg                    44

<210> SEQ ID NO 106
<211> LENGTH: 26
<212> TYPE: DNA
<213> ORGANISM: Artificial Sequence
<220> FEATURE:
<223> OTHER INFORMATION: PZE-108096011 gemeinsamer Primer

<400> SEQUENCE: 106
catttacaca ctttgcaagg gcccta                                        26

<210> SEQ ID NO 107
<211> LENGTH: 44
<212> TYPE: DNA
<213> ORGANISM: Artificial Sequence
<220> FEATURE:
<223> OTHER INFORMATION: PZE-108096791 Primer Allel X

<400> SEQUENCE: 107
gaaggtgacc aagttcatgc tagcacgaat cagcttccaa gagt                    44

<210> SEQ ID NO 108
<211> LENGTH: 43
<212> TYPE: DNA
<213> ORGANISM: Artificial Sequence
<220> FEATURE:
<223> OTHER INFORMATION: PZE-108096791 Primer Allel Y

<400> SEQUENCE: 108
gaaggtcgga gtcaacggat tgcacgaatc agcttccaag agc                     43

<210> SEQ ID NO 109
<211> LENGTH: 29
<212> TYPE: DNA
<213> ORGANISM: Artificial Sequence
<220> FEATURE:
<223> OTHER INFORMATION: PZE-108096791 gemeinsamer Primer

<400> SEQUENCE: 109
attcgaagtg cactgcattc tttgtcaaa                                    29

<210> SEQ ID NO 110
<211> LENGTH: 47
<212> TYPE: DNA
<213> ORGANISM: Artificial Sequence
<220> FEATURE:
<223> OTHER INFORMATION: PZE-108096791 Primer Allel X

<400> SEQUENCE: 110
gaaggtgacc aagttcatgc tgtcaaacat ataagagggc aaagtca                47

<210> SEQ ID NO 111
<211> LENGTH: 47
<212> TYPE: DNA
<213> ORGANISM: Artificial Sequence
<220> FEATURE:
<223> OTHER INFORMATION: PZE-108096791 Primer Allel Y

<400> SEQUENCE: 111
gaaggtcgga gtcaacggat tgtcaaacat ataagagggc aaagtcg                47

<210> SEQ ID NO 112
<211> LENGTH: 29
<212> TYPE: DNA
<213> ORGANISM: Artificial Sequence
<220> FEATURE:
<223> OTHER INFORMATION: PZE-108096791 gemeinsamer Primer

<400> SEQUENCE: 112
tgttccgttc tacattttga tgtacctct                                    29

<210> SEQ ID NO 113
<211> LENGTH: 20
<212> TYPE: DNA
<213> ORGANISM: Artificial Sequence
<220> FEATURE:
<223> OTHER INFORMATION: bnlg1782 forward Primer

<400> SEQUENCE: 113
cgatgctccg ctaggaatag                                              20

<210> SEQ ID NO 114
<211> LENGTH: 20
<212> TYPE: DNA
<213> ORGANISM: Artificial Sequence
<220> FEATURE:
<223> OTHER INFORMATION: bnlg1782 reverse Primer

<400> SEQUENCE: 114
tgtgttggaa attgacccaa                                              20

<210> SEQ ID NO 115
<211> LENGTH: 23
<212> TYPE: DNA
<213> ORGANISM: Artificial Sequence
<220> FEATURE:
<223> OTHER INFORMATION: umc1960 forward Primer -continued

```
<400> SEQUENCE: 115
ctgctggact acatggtgga ctt                                              23

<210> SEQ ID NO 116
<211> LENGTH: 21
<212> TYPE: DNA
<213> ORGANISM: Artificial Sequence
<220> FEATURE:
<223> OTHER INFORMATION: umc1960 reverse Primer

<400> SEQUENCE: 116
gagctgtagc accccaaaa c                                                 21

<210> SEQ ID NO 117
<211> LENGTH: 25
<212> TYPE: DNA
<213> ORGANISM: Artificial Sequence
<220> FEATURE:
<223> OTHER INFORMATION: bnlg240 forward Primer

<400> SEQUENCE: 117
aagaacagaa ggcattgata cataa                                            25

<210> SEQ ID NO 118
<211> LENGTH: 20
<212> TYPE: DNA
<213> ORGANISM: Artificial Sequence
<220> FEATURE:
<223> OTHER INFORMATION: bnlg240 reverse Primer

<400> SEQUENCE: 118
tgcaggtgta tgggcagcta                                                  20

<210> SEQ ID NO 119
<211> LENGTH: 24
<212> TYPE: DNA
<213> ORGANISM: Artificial Sequence
<220> FEATURE:
<223> OTHER INFORMATION: umc1121 forward Primer

<400> SEQUENCE: 119
aaaacgacat gtcatcgtct tcaa                                             24

<210> SEQ ID NO 120
<211> LENGTH: 24
<212> TYPE: DNA
<213> ORGANISM: Artificial Sequence
<220> FEATURE:
<223> OTHER INFORMATION: umc1121 forward Primer

<400> SEQUENCE: 120
ggggtcaggt acagggctag tagt                                             24

<210> SEQ ID NO 121
<211> LENGTH: 20
<212> TYPE: DNA
<213> ORGANISM: Artificial Sequence
<220> FEATURE:
<223> OTHER INFORMATION: bnlg1067 forward Primer

<400> SEQUENCE: 121
ggcttgcttt tgcttcactt                                                  20

<210> SEQ ID NO 122
<211> LENGTH: 20
```

-continued

```
<212> TYPE: DNA
<213> ORGANISM: Artificial Sequence
<220> FEATURE:
<223> OTHER INFORMATION: bnlg1067 reverse Primer

<400> SEQUENCE: 122
ctcatcccat tcgttccact                                              20

<210> SEQ ID NO 123
<211> LENGTH: 42
<212> TYPE: DNA
<213> ORGANISM: Artificial Sequence
<220> FEATURE:
<223> OTHER INFORMATION: umc1287 forward Primer

<400> SEQUENCE: 123
tgtaaaacga cggccagtat gggatgatca gtcgtttcag tc                     42

<210> SEQ ID NO 124
<211> LENGTH: 24
<212> TYPE: DNA
<213> ORGANISM: Artificial Sequence
<220> FEATURE:
<223> OTHER INFORMATION: umc1287 reverse Primer

<400> SEQUENCE: 124
aacgcacttc ttgtagctgt aggg                                         24

<210> SEQ ID NO 125
<211> LENGTH: 20
<212> TYPE: DNA
<213> ORGANISM: Artificial Sequence
<220> FEATURE:
<223> OTHER INFORMATION: 579ZMPM0_2F Primer

<400> SEQUENCE: 125
actcgcttgt ctgtgtcacg                                              20

<210> SEQ ID NO 126
<211> LENGTH: 21
<212> TYPE: DNA
<213> ORGANISM: Artificial Sequence
<220> FEATURE:
<223> OTHER INFORMATION: 579ZMPM0_2R Primer

<400> SEQUENCE: 126
cttgtcgatt ctccgatctc a                                            21

<210> SEQ ID NO 127
<211> LENGTH: 20
<212> TYPE: DNA
<213> ORGANISM: Artificial Sequence
<220> FEATURE:
<223> OTHER INFORMATION: 579ZMPM0_4F Primer

<400> SEQUENCE: 127
cttccagacc gacgtgagat                                              20

<210> SEQ ID NO 128
<211> LENGTH: 20
<212> TYPE: DNA
<213> ORGANISM: Artificial Sequence
<220> FEATURE:
<223> OTHER INFORMATION: 579ZMPM0_4R Primer

<400> SEQUENCE: 128
```

-continued aatactatgc aaggtcggcg                                              20

<210> SEQ ID NO 129
<211> LENGTH: 20
<212> TYPE: DNA
<213> ORGANISM: Artificial Sequence
<220> FEATURE:
<223> OTHER INFORMATION: 579ZMPM0_5F Primer

<400> SEQUENCE: 129
ggcattatta gctaggcgca                                              20

<210> SEQ ID NO 130
<211> LENGTH: 20
<212> TYPE: DNA
<213> ORGANISM: Artificial Sequence
<220> FEATURE:
<223> OTHER INFORMATION: 579ZMPM0_5R Primer

<400> SEQUENCE: 130
ttgggaaact caggttctgc                                              20

<210> SEQ ID NO 131
<211> LENGTH: 20
<212> TYPE: DNA
<213> ORGANISM: Artificial Sequence
<220> FEATURE:
<223> OTHER INFORMATION: 579ZMPM0_17F Primer

<400> SEQUENCE: 131
tgtaccccag ctacgacgtt                                              20

<210> SEQ ID NO 132
<211> LENGTH: 20
<212> TYPE: DNA
<213> ORGANISM: Artificial Sequence
<220> FEATURE:
<223> OTHER INFORMATION: 579ZMPM0_17R  Primer

<400> SEQUENCE: 132
aaccttcacg caaagaatcg                                              20

<210> SEQ ID NO 133
<211> LENGTH: 20
<212> TYPE: DNA
<213> ORGANISM: Artificial Sequence
<220> FEATURE:
<223> OTHER INFORMATION: 579ZMPM0_16F Primer

<400> SEQUENCE: 133
aaacatatgc gtgatcggct                                              20

<210> SEQ ID NO 134
<211> LENGTH: 20
<212> TYPE: DNA
<213> ORGANISM: Artificial Sequence
<220> FEATURE:
<223> OTHER INFORMATION: 579ZMPM0_16R Primer

<400> SEQUENCE: 134
atggctcgtt tcttcaggtg                                              20

<210> SEQ ID NO 135
<211> LENGTH: 22
<212> TYPE: DNA
<213> ORGANISM: Artificial Sequence

```
<220> FEATURE:
<223> OTHER INFORMATION: 579ZMPM0_25F Primer

<400> SEQUENCE: 135
ttggaccaaa cactatcgat cc                                              22

<210> SEQ ID NO 136
<211> LENGTH: 21
<212> TYPE: DNA
<213> ORGANISM: Artificial Sequence
<220> FEATURE:
<223> OTHER INFORMATION: 579ZMPM0_25R Primer

<400> SEQUENCE: 136
cgttggcaaa acctaggaat c                                               21

<210> SEQ ID NO 137
<211> LENGTH: 20
<212> TYPE: DNA
<213> ORGANISM: Artificial Sequence
<220> FEATURE:
<223> OTHER INFORMATION: 579ZMPM0_22F Primer

<400> SEQUENCE: 137
actggaactg caggaaggtg                                                 20

<210> SEQ ID NO 138
<211> LENGTH: 20
<212> TYPE: DNA
<213> ORGANISM: Artificial Sequence
<220> FEATURE:
<223> OTHER INFORMATION: 579ZMPM0_22R Primer

<400> SEQUENCE: 138
gacgtttaac cggcagtcag                                                 20

<210> SEQ ID NO 139
<211> LENGTH: 20
<212> TYPE: DNA
<213> ORGANISM: Artificial Sequence
<220> FEATURE:
<223> OTHER INFORMATION: 579ZMPM0_34F Primer

<400> SEQUENCE: 139
tgaattgcaa gcccacacta                                                 20

<210> SEQ ID NO 140
<211> LENGTH: 20
<212> TYPE: DNA
<213> ORGANISM: Artificial Sequence
<220> FEATURE:
<223> OTHER INFORMATION: 579ZMPM0_34R Primer

<400> SEQUENCE: 140
cctggtttgc tgctcttcat                                                 20

<210> SEQ ID NO 141
<211> LENGTH: 20
<212> TYPE: DNA
<213> ORGANISM: Artificial Sequence
<220> FEATURE:
<223> OTHER INFORMATION: 579ZMPM0_35F Primer

<400> SEQUENCE: 141
ccaaatgaac acgaacacca                                                 20
```

```
<210> SEQ ID NO 142
<211> LENGTH: 20
<212> TYPE: DNA
<213> ORGANISM: Artificial Sequence
<220> FEATURE:
<223> OTHER INFORMATION: 579ZMPM0_35R Primer

<400> SEQUENCE: 142
ggcgtggtga cttttttgtct                                              20

<210> SEQ ID NO 143
<211> LENGTH: 20
<212> TYPE: DNA
<213> ORGANISM: Artificial Sequence
<220> FEATURE:
<223> OTHER INFORMATION: 579ZMPM0_38F Primer

<400> SEQUENCE: 143
cccaagatga agatccgatg                                               20

<210> SEQ ID NO 144
<211> LENGTH: 20
<212> TYPE: DNA
<213> ORGANISM: Artificial Sequence
<220> FEATURE:
<223> OTHER INFORMATION: 579ZMPM0_38R Primer

<400> SEQUENCE: 144
caaaccaaag aactcgagcg                                               20

<210> SEQ ID NO 145
<211> LENGTH: 20
<212> TYPE: DNA
<213> ORGANISM: Artificial Sequence
<220> FEATURE:
<223> OTHER INFORMATION: 579ZMPM0_37F Primer

<400> SEQUENCE: 145
gtaatggggc agatgtttgg                                               20

<210> SEQ ID NO 146
<211> LENGTH: 20
<212> TYPE: DNA
<213> ORGANISM: Artificial Sequence
<220> FEATURE:
<223> OTHER INFORMATION: 579ZMPM0_37R Primer

<400> SEQUENCE: 146
gcgactcttc gctacacacc                                               20

<210> SEQ ID NO 147
<211> LENGTH: 24
<212> TYPE: DNA
<213> ORGANISM: Artificial Sequence
<220> FEATURE:
<223> OTHER INFORMATION: 579ZMPM0_41F Primer
<220> FEATURE:
<221> NAME/KEY: misc_feature
<222> LOCATION: (1)..(3)
<223> OTHER INFORMATION: n is a, c, g, or t

<400> SEQUENCE: 147 nnncccctgtt catgtaactt caat                                         24

<210> SEQ ID NO 148
<211> LENGTH: 20
```

```
<212> TYPE: DNA
<213> ORGANISM: Artificial Sequence
<220> FEATURE:
<223> OTHER INFORMATION: 579ZMPM0_41R Primer

<400> SEQUENCE: 148
tgcacacgat aaggacatgc                                              20

<210> SEQ ID NO 149
<211> LENGTH: 24
<212> TYPE: DNA
<213> ORGANISM: Artificial Sequence
<220> FEATURE:
<223> OTHER INFORMATION: 579ZMPM0_41F Primer
<220> FEATURE:
<221> NAME/KEY: misc_feature
<222> LOCATION: (1)..(3)
<223> OTHER INFORMATION: n is a, c, g, or t

<400> SEQUENCE: 149
nnnccctgtt catgtaactt caat                                         24

<210> SEQ ID NO 150
<211> LENGTH: 20
<212> TYPE: DNA
<213> ORGANISM: Artificial Sequence
<220> FEATURE:
<223> OTHER INFORMATION: 579ZMPM0_41R Primer

<400> SEQUENCE: 150
tgcacacgat aaggacatgc                                              20

<210> SEQ ID NO 151
<211> LENGTH: 20
<212> TYPE: DNA
<213> ORGANISM: Artificial Sequence
<220> FEATURE:
<223> OTHER INFORMATION: 579ZMPM0_46F Primer

<400> SEQUENCE: 151
tcaagagaac tctgggtggc                                              20

<210> SEQ ID NO 152
<211> LENGTH: 20
<212> TYPE: DNA
<213> ORGANISM: Artificial Sequence
<220> FEATURE:
<223> OTHER INFORMATION: 579ZMPM0_46r Primer

<400> SEQUENCE: 152
ggccaacaat gacgagagtc                                              20

<210> SEQ ID NO 153
<211> LENGTH: 20
<212> TYPE: DNA
<213> ORGANISM: Artificial Sequence
<220> FEATURE:
<223> OTHER INFORMATION: 579ZMPM0_180F Primer

<400> SEQUENCE: 153
gggagggttg ttctggtttt                                              20

<210> SEQ ID NO 154
<211> LENGTH: 20
<212> TYPE: DNA
<213> ORGANISM: Artificial Sequence
<220> FEATURE:
```

-continued

<223> OTHER INFORMATION: 579ZMPM0_180R2 Primer

<400> SEQUENCE: 154
ggtccttgtc aatgtcaccc                                        20

<210> SEQ ID NO 155
<211> LENGTH: 20
<212> TYPE: DNA
<213> ORGANISM: Artificial Sequence
<220> FEATURE:
<223> OTHER INFORMATION: 579ZMPM0_48F Primer

<400> SEQUENCE: 155
atggaccccc gttgttatct                                        20

<210> SEQ ID NO 156
<211> LENGTH: 20
<212> TYPE: DNA
<213> ORGANISM: Artificial Sequence
<220> FEATURE:
<223> OTHER INFORMATION: 579ZMPM0_48R Primer

<400> SEQUENCE: 156
gcctgcagac aaattcctgt                                        20

<210> SEQ ID NO 157
<211> LENGTH: 20
<212> TYPE: DNA
<213> ORGANISM: Artificial Sequence
<220> FEATURE:
<223> OTHER INFORMATION: 579ZMPM0_48F Primer

<400> SEQUENCE: 157
atggaccccc gttgttatct                                        20

<210> SEQ ID NO 158
<211> LENGTH: 20
<212> TYPE: DNA
<213> ORGANISM: Artificial Sequence
<220> FEATURE:
<223> OTHER INFORMATION: 579ZMPM0_48R Primer

<400> SEQUENCE: 158
gcctgcagac aaattcctgt                                        20

<210> SEQ ID NO 159
<211> LENGTH: 20
<212> TYPE: DNA
<213> ORGANISM: Artificial Sequence
<220> FEATURE:
<223> OTHER INFORMATION: 579ZMPM0_56F Primer

<400> SEQUENCE: 159
cctgtcatgg tgggaacaat                                        20

<210> SEQ ID NO 160
<211> LENGTH: 20
<212> TYPE: DNA
<213> ORGANISM: Artificial Sequence
<220> FEATURE:
<223> OTHER INFORMATION: 579ZMPM0_56R Primer

<400> SEQUENCE: 160
ctcatcagcg aagcgaaaaa                                        20

```
<210> SEQ ID NO 161
<211> LENGTH: 20
<212> TYPE: DNA
<213> ORGANISM: Artificial Sequence
<220> FEATURE:
<223> OTHER INFORMATION: 579ZMPM0_51F Primer

<400> SEQUENCE: 161
accctctcct tgctattggc                                               20

<210> SEQ ID NO 162
<211> LENGTH: 20
<212> TYPE: DNA
<213> ORGANISM: Artificial Sequence
<220> FEATURE:
<223> OTHER INFORMATION: 579ZMPM0_51R Primer

<400> SEQUENCE: 162
ctccagctct tcgttcgttc                                               20

<210> SEQ ID NO 163
<211> LENGTH: 20
<212> TYPE: DNA
<213> ORGANISM: Artificial Sequence
<220> FEATURE:
<223> OTHER INFORMATION: 579ZMPM0_199F Primer

<400> SEQUENCE: 163
gcaggctgga caaaagtgtt                                               20

<210> SEQ ID NO 164
<211> LENGTH: 20
<212> TYPE: DNA
<213> ORGANISM: Artificial Sequence
<220> FEATURE:
<223> OTHER INFORMATION: 579ZMPM0_199R Primer

<400> SEQUENCE: 164 ttcttttgc ggcctatctg                                                20

<210> SEQ ID NO 165
<211> LENGTH: 20
<212> TYPE: DNA
<213> ORGANISM: Artificial Sequence
<220> FEATURE:
<223> OTHER INFORMATION: 579ZMPM0_63F Primer

<400> SEQUENCE: 165
atttgcttgg cgtaatcctg                                               20

<210> SEQ ID NO 166
<211> LENGTH: 20
<212> TYPE: DNA
<213> ORGANISM: Artificial Sequence
<220> FEATURE:
<223> OTHER INFORMATION: 579ZMPM0_63R Primer

<400> SEQUENCE: 166
cagccgtgtt tttctttgct                                               20

<210> SEQ ID NO 167
<211> LENGTH: 20
<212> TYPE: DNA
<213> ORGANISM: Artificial Sequence
<220> FEATURE:
<223> OTHER INFORMATION: 579ZMPM0_208F Primer
```

<400> SEQUENCE: 167
cgcacggatc aagaagagtt                                          20

<210> SEQ ID NO 168
<211> LENGTH: 20
<212> TYPE: DNA
<213> ORGANISM: Artificial Sequence
<220> FEATURE:
<223> OTHER INFORMATION: 579ZMPM0_208R Primer

<400> SEQUENCE: 168
caatcgccat gcatactttg                                          20

<210> SEQ ID NO 169
<211> LENGTH: 22
<212> TYPE: DNA
<213> ORGANISM: Artificial Sequence
<220> FEATURE:
<223> OTHER INFORMATION: 579ZMPM0_206F Primer

<400> SEQUENCE: 169
atggtacaag tgtcgatccc tc                                       22

<210> SEQ ID NO 170
<211> LENGTH: 20
<212> TYPE: DNA
<213> ORGANISM: Artificial Sequence
<220> FEATURE:
<223> OTHER INFORMATION: 579ZMPM0_206R Primer

<400> SEQUENCE: 170
aatgaatcga tgtcgctggt                                          20

<210> SEQ ID NO 171
<211> LENGTH: 22
<212> TYPE: DNA
<213> ORGANISM: Artificial Sequence
<220> FEATURE:
<223> OTHER INFORMATION: 579ZMPM0_86F Primer

<400> SEQUENCE: 171
cacaactaaa gaggaaaccg ga                                       22

<210> SEQ ID NO 172
<211> LENGTH: 20
<212> TYPE: DNA
<213> ORGANISM: Artificial Sequence
<220> FEATURE:
<223> OTHER INFORMATION: 579ZMPM0_86R Primer

<400> SEQUENCE: 172
ggctgacggt ctagtcttcg                                          20

<210> SEQ ID NO 173
<211> LENGTH: 20
<212> TYPE: DNA
<213> ORGANISM: Artificial Sequence
<220> FEATURE:
<223> OTHER INFORMATION: 579ZMPM0_79F Primer

<400> SEQUENCE: 173
aaccaaatgg ggtcttagcc                                          20

<210> SEQ ID NO 174
<211> LENGTH: 20

```
<212> TYPE: DNA
<213> ORGANISM: Artificial Sequence
<220> FEATURE:
<223> OTHER INFORMATION: 579ZMPM0_79R Primer

<400> SEQUENCE: 174
atccgccact ggtcaaaata                                          20

<210> SEQ ID NO 175
<211> LENGTH: 20
<212> TYPE: DNA
<213> ORGANISM: Artificial Sequence
<220> FEATURE:
<223> OTHER INFORMATION: 579ZMPM0_278F Primer

<400> SEQUENCE: 175
catcgcaaca tcagcaacat                                          20

<210> SEQ ID NO 176
<211> LENGTH: 20
<212> TYPE: DNA
<213> ORGANISM: Artificial Sequence
<220> FEATURE:
<223> OTHER INFORMATION: 579ZMPM0_278R Primer

<400> SEQUENCE: 176
acgtttgttc ccttcatcca                                          20

<210> SEQ ID NO 177
<211> LENGTH: 20
<212> TYPE: DNA
<213> ORGANISM: Artificial Sequence
<220> FEATURE:
<223> OTHER INFORMATION: 579zmpm0_209F Primer

<400> SEQUENCE: 177
ctgtgcttct ggtgctgaaa                                          20

<210> SEQ ID NO 178
<211> LENGTH: 20
<212> TYPE: DNA
<213> ORGANISM: Artificial Sequence
<220> FEATURE:
<223> OTHER INFORMATION: 579zmpm0_209R Primer

<400> SEQUENCE: 178 cttteccgcc tgtaaatgaa                                          20

<210> SEQ ID NO 179
<211> LENGTH: 22
<212> TYPE: DNA
<213> ORGANISM: Artificial Sequence
<220> FEATURE:
<223> OTHER INFORMATION: 579zmpm0_86F Primer

<400> SEQUENCE: 179
cacaactaaa gaggaaaccg ga                                       22

<210> SEQ ID NO 180
<211> LENGTH: 22
<212> TYPE: DNA
<213> ORGANISM: Artificial Sequence
<220> FEATURE:
<223> OTHER INFORMATION: 579zmpm0_86F

<400> SEQUENCE: 180
```

```
cacaactaaa gaggaaaccg ga                                              22

<210> SEQ ID NO 181
<211> LENGTH: 20
<212> TYPE: DNA
<213> ORGANISM: Artificial Sequence
<220> FEATURE:
<223> OTHER INFORMATION: 579zmpm0_87F Primer

<400> SEQUENCE: 181 ctcacccccac cctaccctat                                                20

<210> SEQ ID NO 182
<211> LENGTH: 20
<212> TYPE: DNA
<213> ORGANISM: Artificial Sequence
<220> FEATURE:
<223> OTHER INFORMATION: 579zmpm0_87R Primer

<400> SEQUENCE: 182
ggggagctgt tgaaggaaat                                                 20

<210> SEQ ID NO 183
<211> LENGTH: 20
<212> TYPE: DNA
<213> ORGANISM: Artificial Sequence
<220> FEATURE:
<223> OTHER INFORMATION: 579zmpm0_91F Primer

<400> SEQUENCE: 183
acgtcgatct gcttgctacc                                                 20

<210> SEQ ID NO 184
<211> LENGTH: 20
<212> TYPE: DNA
<213> ORGANISM: Artificial Sequence
<220> FEATURE:
<223> OTHER INFORMATION: 579zmpm0_91R Primer

<400> SEQUENCE: 184
gagacctagc gatccaacga                                                 20

<210> SEQ ID NO 185
<211> LENGTH: 21
<212> TYPE: DNA
<213> ORGANISM: Artificial Sequence
<220> FEATURE:
<223> OTHER INFORMATION: 579zmpm0_216F Primer

<400> SEQUENCE: 185
ctccatagtg tttcggcctt t                                               21

<210> SEQ ID NO 186
<211> LENGTH: 20
<212> TYPE: DNA
<213> ORGANISM: Artificial Sequence
<220> FEATURE:
<223> OTHER INFORMATION: 579zmpm0_216R Primer

<400> SEQUENCE: 186
gccctcagga cttaccgact                                                 20

<210> SEQ ID NO 187
<211> LENGTH: 20
<212> TYPE: DNA
<213> ORGANISM: Artificial Sequence
```

```
<220> FEATURE:
<223> OTHER INFORMATION: 579ZMPM0_95F Primer

<400> SEQUENCE: 187
gtcactatac ggagacggcg                                               20

<210> SEQ ID NO 188
<211> LENGTH: 20
<212> TYPE: DNA
<213> ORGANISM: Artificial Sequence
<220> FEATURE:
<223> OTHER INFORMATION: 579ZMPM0_95R Primer

<400> SEQUENCE: 188
ctcggccttc aatttgtgat                                               20

<210> SEQ ID NO 189
<211> LENGTH: 20
<212> TYPE: DNA
<213> ORGANISM: Artificial Sequence
<220> FEATURE:
<223> OTHER INFORMATION: 579ZMPM0_99F Primer

<400> SEQUENCE: 189
agagcaacat gccttgaacc                                               20

<210> SEQ ID NO 190
<211> LENGTH: 20
<212> TYPE: DNA
<213> ORGANISM: Artificial Sequence
<220> FEATURE:
<223> OTHER INFORMATION: 579ZMPM0_99R Primer

<400> SEQUENCE: 190
gttttgatcc cgaagccttt                                               20

<210> SEQ ID NO 191
<211> LENGTH: 21
<212> TYPE: DNA
<213> ORGANISM: Artificial Sequence
<220> FEATURE:
<223> OTHER INFORMATION: 579ZMPM0_244F Primer

<400> SEQUENCE: 191
attcaatgga cacgcaacaa t                                             21

<210> SEQ ID NO 192
<211> LENGTH: 20
<212> TYPE: DNA
<213> ORGANISM: Artificial Sequence
<220> FEATURE:
<223> OTHER INFORMATION: 579ZMPM0_244R Primer

<400> SEQUENCE: 192
tgtggtgggg attttagtgg                                               20

<210> SEQ ID NO 193
<211> LENGTH: 20
<212> TYPE: DNA
<213> ORGANISM: Artificial Sequence
<220> FEATURE:
<223> OTHER INFORMATION: 579ZMPM0_241F Primer

<400> SEQUENCE: 193
cattcgaaaa tctggccact                                               20
```

<210> SEQ ID NO 194
<211> LENGTH: 20
<212> TYPE: DNA
<213> ORGANISM: Artificial Sequence
<220> FEATURE:
<223> OTHER INFORMATION: 579ZMPM0_241R Primer

<400> SEQUENCE: 194
gccaatggaa tggagaacag                                               20

<210> SEQ ID NO 195
<211> LENGTH: 20
<212> TYPE: DNA
<213> ORGANISM: Artificial Sequence
<220> FEATURE:
<223> OTHER INFORMATION: 579ZMPM0_109F Primer

<400> SEQUENCE: 195
gagcaaatca gatgcagcaa                                               20

<210> SEQ ID NO 196
<211> LENGTH: 20
<212> TYPE: DNA
<213> ORGANISM: Artificial Sequence
<220> FEATURE:
<223> OTHER INFORMATION: 579ZMPM0_109R Primer

<400> SEQUENCE: 196
tgatgatggt ctgttgccag                                               20

<210> SEQ ID NO 197
<211> LENGTH: 20
<212> TYPE: DNA
<213> ORGANISM: Artificial Sequence
<220> FEATURE:
<223> OTHER INFORMATION: 579ZMPM0_109F Primer

<400> SEQUENCE: 197
gagcaaatca gatgcagcaa                                               20

<210> SEQ ID NO 198
<211> LENGTH: 20
<212> TYPE: DNA
<213> ORGANISM: Artificial Sequence
<220> FEATURE:
<223> OTHER INFORMATION: 579ZMPM0_109R Primer

<400> SEQUENCE: 198
tgatgatggt ctgttgccag                                               20

<210> SEQ ID NO 199
<211> LENGTH: 20
<212> TYPE: DNA
<213> ORGANISM: Artificial Sequence
<220> FEATURE:
<223> OTHER INFORMATION: 579ZMPM0_247F Primer

<400> SEQUENCE: 199
tgcaaccata tgttgatggg                                               20

<210> SEQ ID NO 200
<211> LENGTH: 20
<212> TYPE: DNA
<213> ORGANISM: Artificial Sequence
<220> FEATURE:
<223> OTHER INFORMATION: 579ZMPM0_247R Primer

<400> SEQUENCE: 200
cagcttgaga caaacgctga                                              20

<210> SEQ ID NO 201
<211> LENGTH: 20
<212> TYPE: DNA
<213> ORGANISM: Artificial Sequence
<220> FEATURE:
<223> OTHER INFORMATION: 579ZMPM0_112F Primer

<400> SEQUENCE: 201
tgaaaaccct acctgaagcg                                              20

<210> SEQ ID NO 202
<211> LENGTH: 20
<212> TYPE: DNA
<213> ORGANISM: Artificial Sequence
<220> FEATURE:
<223> OTHER INFORMATION: 579ZMPM0_112R Primer

<400> SEQUENCE: 202
actgcactga tccggacttc                                              20

<210> SEQ ID NO 203
<211> LENGTH: 21
<212> TYPE: DNA
<213> ORGANISM: Artificial Sequence
<220> FEATURE:
<223> OTHER INFORMATION: 579ZMPM0_125F Primer

<400> SEQUENCE: 203
tcgaggctaa catggtctct g                                            21

<210> SEQ ID NO 204
<211> LENGTH: 21
<212> TYPE: DNA
<213> ORGANISM: Artificial Sequence
<220> FEATURE:
<223> OTHER INFORMATION: 579ZMPM0_125R

<400> SEQUENCE: 204
catacacttc atgtcgtccc g                                            21

<210> SEQ ID NO 205
<211> LENGTH: 20
<212> TYPE: DNA
<213> ORGANISM: Artificial Sequence
<220> FEATURE:
<223> OTHER INFORMATION: 579ZMPM0_253F Primer

<400> SEQUENCE: 205
ggccgggacg tactagtgta                                              20

<210> SEQ ID NO 206
<211> LENGTH: 20
<212> TYPE: DNA
<213> ORGANISM: Artificial Sequence
<220> FEATURE:
<223> OTHER INFORMATION: 579ZMPM0_253R Primer

<400> SEQUENCE: 206
tggttgtcat catttggcac                                              20

<210> SEQ ID NO 207

```
<211> LENGTH: 21
<212> TYPE: DNA
<213> ORGANISM: Artificial Sequence
<220> FEATURE:
<223> OTHER INFORMATION: 579ZMPM0_125F Primer

<400> SEQUENCE: 207
tcgaggctaa catggtctct g                                              21

<210> SEQ ID NO 208
<211> LENGTH: 21
<212> TYPE: DNA
<213> ORGANISM: Artificial Sequence
<220> FEATURE:
<223> OTHER INFORMATION: 579ZMPM0_125R Primer

<400> SEQUENCE: 208
catacacttc atgtcgtccc g                                              21

<210> SEQ ID NO 209
<211> LENGTH: 20
<212> TYPE: DNA
<213> ORGANISM: Artificial Sequence
<220> FEATURE:
<223> OTHER INFORMATION: 579ZMPM0_128F Primer

<400> SEQUENCE: 209
gctcaaggcg atacatgctt                                                20

<210> SEQ ID NO 210
<211> LENGTH: 20
<212> TYPE: DNA
<213> ORGANISM: Artificial Sequence
<220> FEATURE:
<223> OTHER INFORMATION: 579ZMPM0_128F

<400> SEQUENCE: 210
gctcaaggcg atacatgctt                                                20

<210> SEQ ID NO 211
<211> LENGTH: 16
<212> TYPE: DNA
<213> ORGANISM: Artificial Sequence
<220> FEATURE:
<223> OTHER INFORMATION: 579ZMPM0_136F Primer

<400> SEQUENCE: 211
ggcttgactg taatgg                                                    16

<210> SEQ ID NO 212
<211> LENGTH: 20
<212> TYPE: DNA
<213> ORGANISM: Artificial Sequence
<220> FEATURE:
<223> OTHER INFORMATION: 579ZMPM0_136R Primer

<400> SEQUENCE: 212
tttctgctca cacttcggtg                                                20

<210> SEQ ID NO 213
<211> LENGTH: 25
<212> TYPE: DNA
<213> ORGANISM: Artificial Sequence
<220> FEATURE:
<223> OTHER INFORMATION: 579ZMPM0_131F Primer

<400> SEQUENCE: 213
```
tcaagcaaac gagactcttc ttgta                                         25

<210> SEQ ID NO 214
<211> LENGTH: 20
<212> TYPE: DNA
<213> ORGANISM: Artificial Sequence
<220> FEATURE:
<223> OTHER INFORMATION: 579ZMPM0_131R Primer

<400> SEQUENCE: 214
tagccatgga cagatcgaca                                               20

<210> SEQ ID NO 215
<211> LENGTH: 20
<212> TYPE: DNA
<213> ORGANISM: Artificial Sequence
<220> FEATURE:
<223> OTHER INFORMATION: 579ZMPM0_137F Primer

<400> SEQUENCE: 215
cggaccttgt actccgtcac                                               20

<210> SEQ ID NO 216
<211> LENGTH: 20
<212> TYPE: DNA
<213> ORGANISM: Artificial Sequence
<220> FEATURE:
<223> OTHER INFORMATION: 579ZMPM0_137R Primer

<400> SEQUENCE: 216
agaatgtgga ggctacggtg                                               20

<210> SEQ ID NO 217
<211> LENGTH: 20
<212> TYPE: DNA
<213> ORGANISM: Artificial Sequence
<220> FEATURE:
<223> OTHER INFORMATION: 579ZMPM0_138F Primer

<400> SEQUENCE: 217
tgaaatttag gacttgcccg                                               20

<210> SEQ ID NO 218
<211> LENGTH: 20
<212> TYPE: DNA
<213> ORGANISM: Artificial Sequence
<220> FEATURE:
<223> OTHER INFORMATION: 579ZMPM0_138R Primer

<400> SEQUENCE: 218
acatctgaac accgcattga                                               20

<210> SEQ ID NO 219
<211> LENGTH: 20
<212> TYPE: DNA
<213> ORGANISM: Artificial Sequence
<220> FEATURE:
<223> OTHER INFORMATION: 579ZMPM0_147F Primer

<400> SEQUENCE: 219
cttgtggtcc cactccactt                                               20

<210> SEQ ID NO 220
<211> LENGTH: 20
<212> TYPE: DNA

```
<213> ORGANISM: Artificial Sequence
<220> FEATURE:
<223> OTHER INFORMATION: 579ZMPM0_147R Primer

<400> SEQUENCE: 220
ttactttcca tggcctccaa                                               20

<210> SEQ ID NO 221
<211> LENGTH: 20
<212> TYPE: DNA
<213> ORGANISM: Artificial Sequence
<220> FEATURE:
<223> OTHER INFORMATION: 579ZMPM0_145F Primer

<400> SEQUENCE: 221
tgtgctcggg tattgacgta                                               20

<210> SEQ ID NO 222
<211> LENGTH: 20
<212> TYPE: DNA
<213> ORGANISM: Artificial Sequence
<220> FEATURE:
<223> OTHER INFORMATION: 579ZMPM0_145R Primer

<400> SEQUENCE: 222
ccgtcaactt cctcccctat                                               20

<210> SEQ ID NO 223
<211> LENGTH: 20
<212> TYPE: DNA
<213> ORGANISM: Artificial Sequence
<220> FEATURE:
<223> OTHER INFORMATION: 579ZMPM0_262F Primer

<400> SEQUENCE: 223
ttgctggctt gttatcctcc                                               20

<210> SEQ ID NO 224
<211> LENGTH: 20
<212> TYPE: DNA
<213> ORGANISM: Artificial Sequence
<220> FEATURE:
<223> OTHER INFORMATION: 579ZMPM0_262R Primer

<400> SEQUENCE: 224
ccctgtcgtt caaggaaaaa                                               20

<210> SEQ ID NO 225
<211> LENGTH: 20
<212> TYPE: DNA
<213> ORGANISM: Artificial Sequence
<220> FEATURE:
<223> OTHER INFORMATION: 579ZMPM0_161F Primer

<400> SEQUENCE: 225
taggtaacag aattgcgggc                                               20

<210> SEQ ID NO 226
<211> LENGTH: 20
<212> TYPE: DNA
<213> ORGANISM: Artificial Sequence
<220> FEATURE:
<223> OTHER INFORMATION: 579ZMPM0_161R Primer

<400> SEQUENCE: 226
tttctaaggc atgggagtgc                                               20
```

<210> SEQ ID NO 227
<211> LENGTH: 20
<212> TYPE: DNA
<213> ORGANISM: Artificial Sequence
<220> FEATURE:
<223> OTHER INFORMATION: 579ZMPM0_265F Primer

<400> SEQUENCE: 227
catttcatgg catatgagcg                                              20

<210> SEQ ID NO 228
<211> LENGTH: 20
<212> TYPE: DNA
<213> ORGANISM: Artificial Sequence
<220> FEATURE:
<223> OTHER INFORMATION: 579ZMPM0_265R Primer

<400> SEQUENCE: 228
ctaaaggccc tgttcccagt                                              20

<210> SEQ ID NO 229
<211> LENGTH: 20
<212> TYPE: DNA
<213> ORGANISM: Artificial Sequence
<220> FEATURE:
<223> OTHER INFORMATION: ZNF1_GH034_F_Primer

<400> SEQUENCE: 229
tggttggtgt cgaagctgag                                              20

<210> SEQ ID NO 230
<211> LENGTH: 20
<212> TYPE: DNA
<213> ORGANISM: Artificial Sequence
<220> FEATURE:
<223> OTHER INFORMATION: ZNF1_GH033_R_Primer

<400> SEQUENCE: 230
atttatcccg gcctttgcat                                              20

<210> SEQ ID NO 231
<211> LENGTH: 22
<212> TYPE: DNA
<213> ORGANISM: Artificial Sequence
<220> FEATURE:
<223> OTHER INFORMATION: HYD_GH039_F_Primer

<400> SEQUENCE: 231
gatctacagg gaagcccact ga                                           22

<210> SEQ ID NO 232
<211> LENGTH: 25
<212> TYPE: DNA
<213> ORGANISM: Artificial Sequence
<220> FEATURE:
<223> OTHER INFORMATION: HYD_GH040_R_Primer

<400> SEQUENCE: 232
tttttccttg aggcagttat atgct                                        25

<210> SEQ ID NO 233
<211> LENGTH: 17
<212> TYPE: DNA
<213> ORGANISM: Artificial Sequence
<220> FEATURE:

<223> OTHER INFORMATION: RLK4_GH220_F_Primer

<400> SEQUENCE: 233
ttgtgcagcg gagggaa                                                        17

<210> SEQ ID NO 234
<211> LENGTH: 19
<212> TYPE: DNA
<213> ORGANISM: Artificial Sequence
<220> FEATURE:
<223> OTHER INFORMATION: RLK4_GH221_R_Primer

<400> SEQUENCE: 234
ccagggcacc agcaagaat                                                      19

<210> SEQ ID NO 235
<211> LENGTH: 19
<212> TYPE: DNA
<213> ORGANISM: Artificial Sequence
<220> FEATURE:
<223> OTHER INFORMATION: EXT1_GH168_F_Primer

<400> SEQUENCE: 235
cgactacaag acgcgtacc                                                      19

<210> SEQ ID NO 236
<211> LENGTH: 19
<212> TYPE: DNA
<213> ORGANISM: Artificial Sequence
<220> FEATURE:
<223> OTHER INFORMATION: EXT1_GH170_R_Primer

<400> SEQUENCE: 236
ggtgtcgatg gtgaggttc                                                      19

<210> SEQ ID NO 237
<211> LENGTH: 20
<212> TYPE: DNA
<213> ORGANISM: Artificial Sequence
<220> FEATURE:
<223> OTHER INFORMATION: RLK1_GH138_F_Primer

<400> SEQUENCE: 237
tattgttggt gctgttgccg                                                     20

<210> SEQ ID NO 238
<211> LENGTH: 20
<212> TYPE: DNA
<213> ORGANISM: Artificial Sequence
<220> FEATURE:
<223> OTHER INFORMATION: RLK1_GH139_R_Primer

<400> SEQUENCE: 238
ggactcaatc cttgtccctg                                                     20

<210> SEQ ID NO 239
<211> LENGTH: 20
<212> TYPE: DNA
<213> ORGANISM: Artificial Sequence
<220> FEATURE:
<223> OTHER INFORMATION: RET1_GH055_F_Primer

<400> SEQUENCE: 239
cgctcgtttg ccagatagcc                                                     20

```
<210> SEQ ID NO 240
<211> LENGTH: 20
<212> TYPE: DNA
<213> ORGANISM: Artificial Sequence
<220> FEATURE:
<223> OTHER INFORMATION: RET1_GH056_R_Primer

<400> SEQUENCE: 240
cacggtgtgt gccagtttgt                                                    20

<210> SEQ ID NO 241
<211> LENGTH: 42
<212> TYPE: DNA
<213> ORGANISM: Artificial Sequence
<220> FEATURE:
<223> OTHER INFORMATION: MA0021 Primer Allel X

<400> SEQUENCE: 241
gaaggtgacc aagttcatgc tgagctcatc tcgtccaagc cc                            42

<210> SEQ ID NO 242
<211> LENGTH: 42
<212> TYPE: DNA
<213> ORGANISM: Artificial Sequence
<220> FEATURE:
<223> OTHER INFORMATION: MA0021 Primer Allel Y

<400> SEQUENCE: 242
gaaggtcgga gtcaacggat tgagctcatc tcgtccaagc cg                            42

<210> SEQ ID NO 243
<211> LENGTH: 19
<212> TYPE: DNA
<213> ORGANISM: Artificial Sequence
<220> FEATURE:
<223> OTHER INFORMATION: MA0021 gemeinsamer Primer

<400> SEQUENCE: 243
cgctgcggtg ccgggtgat                                                     19

<210> SEQ ID NO 244
<211> LENGTH: 47
<212> TYPE: DNA
<213> ORGANISM: Artificial Sequence
<220> FEATURE:
<223> OTHER INFORMATION: MA0022 Primer Allel X

<400> SEQUENCE: 244
gaaggtgacc aagttcatgc tcaccaacac aatagtcgtc caaatgt                       47

<210> SEQ ID NO 245
<211> LENGTH: 46
<212> TYPE: DNA
<213> ORGANISM: Artificial Sequence
<220> FEATURE:
<223> OTHER INFORMATION: MA0022 Primer Allel Y

<400> SEQUENCE: 245
gaaggtcgga gtcaacggat taccaacaca atagtcgtcc aaatgc                        46

<210> SEQ ID NO 246
<211> LENGTH: 25
<212> TYPE: DNA
<213> ORGANISM: Artificial Sequence
<220> FEATURE:
<223> OTHER INFORMATION: MA0022 gemeinsamer Primer
```

```
<400> SEQUENCE: 246
cagccaatat ttccctcagt ggctt                                            25

<210> SEQ ID NO 247
<211> LENGTH: 24
<212> TYPE: DNA
<213> ORGANISM: Artificial Sequence
<220> FEATURE:
<223> OTHER INFORMATION: MA04916-6f Primer

<400> SEQUENCE: 247
tgtttcagga atcacgcaac tgga                                             24

<210> SEQ ID NO 248
<211> LENGTH: 22
<212> TYPE: DNA
<213> ORGANISM: Artificial Sequence
<220> FEATURE:
<223> OTHER INFORMATION: MA04916-6r Primer

<400> SEQUENCE: 248
gcaccacgcc atgaccaaca tc                                               22

<210> SEQ ID NO 249
<211> LENGTH: 22
<212> TYPE: DNA
<213> ORGANISM: Artificial Sequence
<220> FEATURE:
<223> OTHER INFORMATION: TG10013-10.f Primer

<400> SEQUENCE: 249
cttcctacag aagaacgaga gt                                               22

<210> SEQ ID NO 250
<211> LENGTH: 21
<212> TYPE: DNA
<213> ORGANISM: Artificial Sequence
<220> FEATURE:
<223> OTHER INFORMATION: TG10013-11.r Primer

<400> SEQUENCE: 250
ttcctcacga gctctgtggt c                                                21
```